United States Patent [19]
Okamoto

[11] Patent Number: 5,973,785
[45] Date of Patent: Oct. 26, 1999

[54] METHOD OF FORMING LIGHT BEAM, APPARATUS THEREFOR, METHOD OF MEASURING SIZES USING THE SAME, METHOD OF INSPECTING APPEARANCE, METHOD OF MEASURING HEIGHT, METHOD OF EXPOSURE, AND METHOD OF FABRICATING SEMICONDUCTOR INTEGRATED CIRCUITS

[75] Inventor: Yoshihiko Okamoto, Ohme, Japan

[73] Assignee: Hitachi, Ltd., Tokyo, Japan

[21] Appl. No.: 08/568,419

[22] Filed: Dec. 6, 1995

Related U.S. Application Data

[62] Division of application No. 08/218,233, Mar. 28, 1994, Pat. No. 5,502,001, which is a continuation of application No. 07/810,374, Dec. 19, 1991, abandoned.

[30] Foreign Application Priority Data

| Dec. 19, 1990 | [JP] | Japan | 2-403662 |
| Mar. 11, 1991 | [JP] | Japan | 3-44712 |
| Apr. 18, 1991 | [JP] | Japan | 3-86461 |
| Apr. 18, 1991 | [JP] | Japan | 3-86462 |
| Oct. 24, 1991 | [JP] | Japan | 3-276011 |

[51] Int. Cl.[6] .................................................. G01B 9/02
[52] U.S. Cl. ........................ 356/354; 356/351; 356/401
[58] Field of Search .................................. 356/345, 354, 356/357, 351, 401

[56] References Cited

U.S. PATENT DOCUMENTS

| 4,511,220 | 4/1985 | Scully ........................................ 372/27 |
| 4,714,348 | 12/1987 | Makosch ................................. 356/351 |
| 4,791,650 | 12/1988 | Tatsuno et al. ........................... 372/50 |
| 4,866,730 | 9/1989 | Szatmari et al. ......................... 372/101 |
| 5,048,029 | 9/1991 | Skupsky et al. ......................... 372/106 |
| 5,148,442 | 9/1992 | O'Neil et al. ............................ 372/101 |
| 5,298,365 | 3/1994 | Okamoto et al. ........................ 430/311 |

FOREIGN PATENT DOCUMENTS

| 0201306 | 12/1986 | European Pat. Off. . |
| 0210397 | 2/1987 | European Pat. Off. . |
| 0312652 | 4/1989 | European Pat. Off. . |
| 62-59296 | 3/1987 | Japan . |
| 62-67514 | 3/1987 | Japan . |
| 2-140743 | 5/1990 | Japan . |
| 2182168 | 5/1987 | United Kingdom . |

OTHER PUBLICATIONS

F. Jenkins et al., *Fundamentals of Optics*, fourth edition, McGraw–Hill, New York, 1976, pp. 270–285.

J. Raffel et al., "Laser Programmed Vias for Restructurable VLSI", *International Electron Devices Meeting*, Dec. 1980, pp. 132–135.

*Primary Examiner*—Robert H. Kim
*Attorney, Agent, or Firm*—Antonelli, Terry, Stout & Kraus, LLP

[57] ABSTRACT

Technology for forming a fine light beam having a size smaller than the theoretical limit determined by the wavelength of light and characteristics of an objective lens. A beam distribution shifter having two light transmission regions is disposed between a source of light and an objective lens, a phase shifter is provided on one of the two light transmission regions to divide the light passing through the beam distribution shifter into two light fluxes having phases opposite to each other, and the two light fluxes are focused through the objective lens to form a fine light beam having a size smaller than the theoretical limit determined by the wavelength of the light and characteristics of the objective lens due to destructive interference between the two light fluxes.

22 Claims, 41 Drawing Sheets

METHOD OF FORMING LIGHT BEAM, APPARATUS THEREFOR, METHOD OF MEASURING SIZES USING THE SAME, METHOD OF INSPECTING APPEARANCE, METHOD OF MEASURING HEIGHT, METHOD OF EXPOSURE, AND METHOD OF FABRICATING SEMICONDUCTOR INTEGRATED CIRCUITS

CROSS-REFERENCES TO RELATED APPLICATIONS

This is a divisional of application Ser. No. 08/218,233 filed on Mar. 28, 1994, now U.S. Pat. No. 5,502,001, which is a continuation of application Ser. No. 07/810,374 filed on Dec. 19, 1991, now abandoned.

BACKGROUND OF THE INVENTION

The present invention relates to technology of forming a fine light beam, such as technology that can be effectively adapted for enhancing the data recording density of an optical disk or an optomagnetic disk, enhancing the resolution of an optical microscope apparatus, enhancing the precision of measurement at the time of measuring the height and size of the surface of a sample, enhancing the precision of inspection at the time of inspecting the presence of foreign matter or defects on the surface of the sample, enhancing the precision of transferring fine patterns in an electron beam drawing device or an optical exposure device, and for enhancing the precision of machining at the time of finely machining the surfaces of semiconductor wafers or semiconductor chips.

In an optical apparatus such as an optical disk apparatus or an optical microscope apparatus, a system has in many cases been employed in which light emitted from a source of light is transformed into a parallel beam through a collimator lens and is focused by an objective lens in order to form a light beam.

In this case, if it is attempted to make very small the spot diameter of the light beam focused by the objective lens, there is a limitation due to the diffraction phenomenon caused by the wavelength of light and the numerical aperture of the objective lens as is widely known.

The diameter (Wo) of a light beam that can be focused by an objective lens is determined according to the following equation:

$$2Wo = k\lambda/NA$$

where

NA is the numerical aperture of the objective lens, and $\lambda$ is the wavelength of light, as described in, for example, "Optical Fiber Application Technology", Nikkei Gijutsu Tosho Co., Dec. 10, 1986, pp. 431–435. Furthermore, the symbol k is a constant that is determined by the superposition condition of the diameter of the objective lens and the distribution of intensity of the light beam, and has the following value:

k=0.5 (when the half-width of the light beam is equal to the diameter of the lens), or k=0.8 (when the $e^{-2}$ intensity width of the light beam is equal to the diameter of the lens).

As described above, the lower limit of the spot diameter of the light beam focused by the objective lens is determined depending upon the wavelength of the light, characteristics of the objective lens, and superposition of the intensity distribution of the light beam.

It is therefore impossible to form a light beam having a diameter smaller than the above limit value, placing a limitation on enhancing the recording density of the optical disk apparatus and on enhancing the resolution of the optical microscope apparatus.

Technology that utilizes a fine light beam includes exposure technology of transferring a pattern of an integrated circuit onto a semiconductor wafer and technology of measuring the height and size of the surface of a sample or of inspecting the appearance of the surface of the sample in addition to the aforementioned optical disk device and the optical microscope apparatus.

In the step (wafer process) of manufacturing a semiconductor integrated circuit device, for example, a pattern of an integrated circuit formed on a photomask (reticle) is transferred onto a photoresist on a semiconductor wafer to form a resist pattern, and a thin film is removed by etching using the resist pattern as a mask or impurity ions are implanted into the semiconductor substrate, in order to form a desired LSI.

In this case, the dimensional precision of the pattern of the integrated circuit formed on the photomask is a factor that greatly affects the yield and reliability of LSIs.

Technology of measuring the size by using a laser beam has heretofore been put into practical use in the step of inspecting the pattern of the integrated circuit formed on the photomask. This is a method of measuring the size of a pattern by irradiating the pattern on the photomask with a laser beam to effect the scanning in the direction of measurement of the size and by detecting a peak position of scattered light or a position at which the reflection factor changes.

In this case, for example, the laser beam is slightly vibrated in the direction of measurement of the size, and the position of scattered light or reflected light is detected in synchronism with this slight vibration in order to improve the precision of measurement.

In the above-mentioned technology of measuring the size using a laser beam, however, there is a problem that it is no more possible to sufficiently focus the beam due to the limitation caused by the wavelength of the light and the numerical aperture of the objective lens when the size of the integrated circuit pattern formed on the photomask becomes nearly as small as the wavelength of the light although the laser beam is focused on the photomask using the objective lens. Therefore, the peak position of the scattered light and the position where the reflection factor changes are broadened, deteriorating the precision of measuring the size.

In the step of inspecting the integrated circuit pattern formed on the semiconductor wafer, furthermore, height-measuring technology has been put into practical use according to which the surface of the wafer is irradiated with a light beam obliquely, and a relative position of the reflected light is measured using an optical sensor such as a CCD (charge-coupled device).

In this case, the light from, for example, a light-emitting diode is focused and is permitted to fall on the surface of the wafer and the reflected light is permitted to be incident on the light detector via an oscillation mirror, and a detection signal obtained by the light detector is detected in synchronism using a modulation signal for driving the oscillation mirror as a reference signal, in an attempt to enhance the precision of measurement.

Even in the above height-measuring technology, however, there is a problem that it becomes no more possible to sufficiently focus the diameter of the light beam as the size of the integrated circuit pattern becomes fine due to the aforementioned limitation caused by the wavelength of the light and the numerical aperture of the object lens. Namely, the spot becomes blurred although the light reflected by the surface of the wafer is focused on the sensor, and the precision of measuring the height is deteriorated.

As a method of inspecting defects and foreign matter on the surfaces of semiconductor wafers and photomasks, furthermore, there has been known appearance inspection technology such that the surfaces thereof are irradiated with a laser beam to detect the light scattered or reflected by defects or foreign matter.

This is the technology in which the surface of a sample (wafer or photomask) is irradiated with a laser beam from a horizontal direction and the light scattered by foreign matter (or a defect) is detected by a detector such as a photomultiplier disposed above the sample.

In this case, a polarizing plate is used to separate the laser beam into two polarization beams whose polarized planes are perpendicular to each other, and the light scattered by the edges of the true pattern formed on the sample and the light scattered by foreign matter (or a defect) are separated from each other, in order to improve the precision of detection.

However, even this appearance inspection technology becomes no more capable of sufficiently focusing the beam diameter due to the limitation caused by the wavelength of the light and the numerical aperture of the objective lens as the size of the integrated circuit pattern formed on the semiconductor wafer or the photomask becomes fine and the size of the defect or foreign matter to be detected becomes fine correspondingly. Therefore, a peak position of the scattered light or a position at which the reflection factor changes is broadened, deteriorating the precision for detecting defects and foreign matter.

There has further been known defect remedy technology which corrects the wiring pattern on the semiconductor wafer using a fine laser beam. Even in this case, however, a limitation is imposed on decreasing the size of the laser beam due to the aforementioned reasons, and the precision of machining the wiring is deteriorated as the size of the wiring pattern becomes fine.

BRIEF SUMMARY OF THE INVENTION

As described above, the lower limit of the spot diameter of a light beam focused by the objective lens is determined by the wavelength of the light, characteristics of the objective lens, and superposition of the intensity distribution of the light beam.

It has therefore been considered impossible to form a light beam having a diameter smaller than the above lower limit, causing problems in various fields of art which utilize fine light beams.

An object of the present invention is to provide technology which is capable of forming a very fine light beam overcoming the limitation caused by the wavelength of the light and characteristics of the objective lens.

Another object of the present invention is to provide technology which is capable of enhancing the recording density of optical disk devices and optomagnetic disk devices.

A further object of the present invention is to provide technology which is capable of enhancing the resolution of an optical microscope apparatus.

A still further object of the present invention is to provide technology which is capable of enhancing the precision of measuring the size of a pattern formed on the surface of a sample.

A still further object of the present invention is to provide technology which is capable of enhancing the precision of measuring the height of the surface of a sample.

A yet further object of the present invention is to provide technology which is capable of enhancing the precision of detecting foreign matter and defects on the surface of a sample.

A further object of the present invention is to provide technology which is capable of enhancing the precision of transferring a fine pattern formed on a photomask.

Another object of the present invention is to provide technology which is capable of enhancing the machining precision when the surface of a semiconductor substrate is to be finely machined using a light beam.

The above-mentioned and other objects as well as novel features of the present invention will become obvious from the description of the specification and the accompanying drawings.

Briefly described below is a representative example of the inventions disclosed in this application.

The outline of one of the inventions is a method of forming a light beam by focusing the light emitted from a source of light through an objective lens, wherein the light is divided into two fluxes of light, the phase of one flux of light is inverted, and the two fluxes of light are then combined together.

A decrease in the precision of a pattern is causing a serious problem in a photolithography process in which an integrated circuit pattern formed on a photomask is transferred onto a semiconductor wafer by using light such as an i-line (wavelength 365 nm) because semiconductor integrated circuits have been fabricated in increasingly finer sizes and the design rules for circuit elements and wiring have been on the order of submicrons.

That is, when a pattern having a pair of light transmission regions $P_1$, $P_2$ and a light blocking region N on a photomask (M) shown in FIG. 59 is transferred onto a wafer, the phases of two light fluxes just after they have transmitted through the light transmission regions $P_1$ and $P_2$ are in phase with each other as shown in FIG. 60 when the light emitted from the source of light is in phase.

As shown in FIG. 61, therefore, these two light fluxes interfere with each other to cause their intensities to become intense in a portion that should have been the light blocking region on the wafer, whereby the projected image of the pattern lowers the contrast on the wafer as shown in FIG. 62 and the depth of focus becomes shallow. Therefore, the precision of transfer greatly decreases as the size of the pattern approaches the order of submicrons which is nearly equal to the wavelength of the source of the light.

As a means for solving such problems, phase-shifting technology is now drawing attention according to which the phase of light passing through the photomask is inverted in order to prevent the contrast of the projected image from decreasing.

For instance, Japanese Patent Publication No. 62-59296 discloses phase-shifting technology in which a transparent film (phase shifter) is formed on one of a pair of light transmission regions between which a light blocking region is sandwiched on the photomask, and the phases of the two light fluxes that have passed through the pair of light transmission regions are rendered opposite to each other in order to weaken the intensity of the two light fluxes that interfere with each other at a portion which should have been the light region on the wafer.

When a pattern having a pair of light transmission regions $P_1$, $P_2$ and a light blocking region N on the photomask (M) as shown in FIG. 63 is transferred onto the wafer by the above-mentioned phase-shifting technology, a phase shifter 8 being a transparent film having a predetermined refractive index is formed on either one of the light transmission regions $P_1$, $P_2$, the thickness of the phase shifter 8 being so adjusted that the two light fluxes just after having passed through the light transmission regions $P_1$ and $P_2$ have opposite phases to each other (see FIG. 64).

By so doing, the above two light fluxes interfere with each other and are weakened in the light blocking region N on the wafer (see FIG. 65). Therefore, the contrast of the projected image of a pattern is improved (see FIG. 66), enabling the resolution and the depth of focus to be improved, and a fine pattern is transferred maintaining a good precision.

Japanese Patent Laid-Open No. 62-67514 discloses phase-shifting technology by which a second very small light transmission region is provided to surround a first light transmission region on a photomask, a phase shifter is formed on either one of these light transmission regions, and the phases of light fluxes that have passed through these two light transmission regions are rendered to be opposite to each other in order to prevent the amplitude of light that has passed through the first light transmission region from spreading in the lateral direction.

Moreover, Japanese Patent Laid-Open No. 2-140743 discloses phase-shifting technology wherein a phase shifter is formed on a portion in the light transmission region, and phases of the two light fluxes that have passed through a portion where the phase shifter exists and a portion without a phase shifter are rendered to be opposite to each other, in order to emphasize the boundary of the phase shifter.

The above technology is related to the art of transferring an integrated circuit pattern formed on the photomask, which, however, can also be applied to forming a fine light beam.

That is, by the above-mentioned phase-shifting technology, the phases of the two light fluxes are rendered to be opposite to each other, and the two light fluxes are focused through an objective lens and are permitted to fall on the surface of a sample. Since the phases of the two light fluxes are opposite to each other, the resulting light beam falling on the sample has a central portion that is suppressed from spreading because of the interference with the periphery of the beam.

It is therefore possible to form a light beam having a diameter which is substantially smaller than a limit value determined by the wavelength of the light or characteristics of the objective lens by suppressing the effect of the beam periphery by, for example, weakening the intensity of light of the periphery to be smaller than the intensity of light of the central portion, so that the trace of irradiation by the central portion of the beam is left on the sample that is irradiated with the light beam.

DETAILED DESCRIPTION OF THE INVENTION

Embodiment 1

Figure 1:
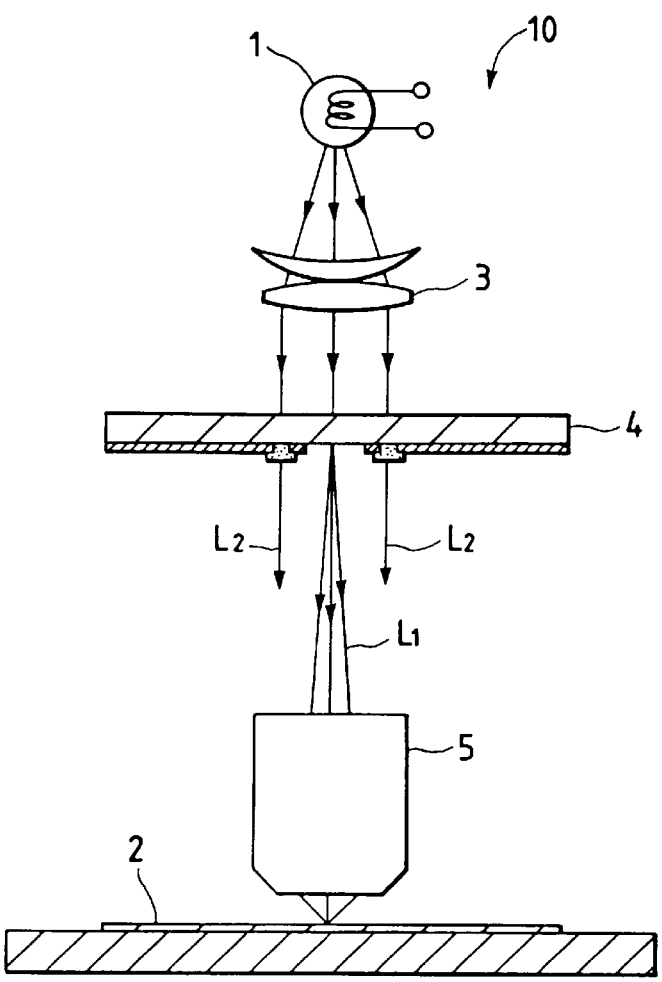
FIG. 1 is a diagram illustrating the structure of an optical system in a light beam-forming apparatus of an embodiment of the present invention.

FIG. 1 shows an optical system of a light beam-forming apparatus 10 according to an embodiment of the present invention.

A condenser lens (or collimator lens) 3, a beam distribution shifter 4 and an objective lens 5 are arranged on an optical path that links a source 1 of light and a sample 2 together. The condenser lens 3 converts the light emitted from the source 1 of light into a parallel beam which falls on the beam distribution shifter 4 to form Koehler illumination.

The beam distribution shifter 4 divides the parallel beam into a light flux $L_1$ that passes through the central portion thereof and a light flux $L_2$ that passes through the peripheral portion, and renders the phases of these two light fluxes $L_1$ and $L_2$ to be opposite to each other. The objective lens 5 focuses the two light fluxes $L_1$ and $L_2$ that have passed through the beam distribution shifter 4 to form a light beam which falls on the surface of the sample 2.

The beam distribution shifter 4 is disposed on the object image plane of the objective lens 5, and the sample is disposed on the image-forming plane of the objective lens 5, so that the projected image of the beam distribution shifter 4 is formed as a fine light beam on the surface of the sample 2.

Figure 2:
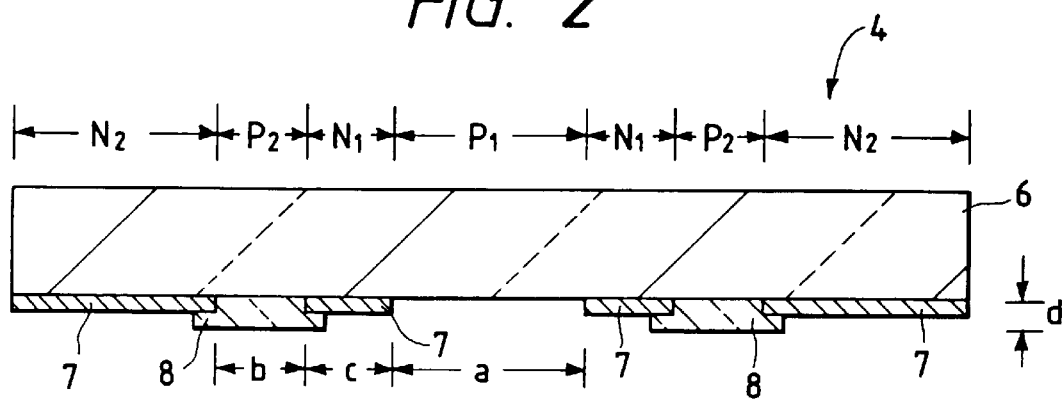
FIG. 2 is a sectional view illustrating the constitution of a beam distribution shifter provided in the light beam-forming apparatus.

FIG. 2 shows an example of constitution of the beam distribution shifter 4 which is constituted by providing light transmission regions $P_1$, $P_2$ and light blocking regions $N_1$, $N_2$ on one surface of a transparent glass substrate 6 made of, for example, synthetic quartz having a refractive index of 1.47.

The light blocking regions $N_1$, $N_2$ are constituted by a light blocking film 7 such as a thin metal film deposited on one surface of a glass substrate 6. The light transmission regions $P_1$ and $P_2$ comprise a light transmission region $P_1$ of a large diameter arranged at the central portion of the glass substrate 6 and a light transmission region $P_2$ of a small width arranged at a periphery thereof.

The light flux $L_1$ of a large intensity that has passed through the light transmission region $P_1$ of the large diameter is incident on the central portion of the objective lens 5, and the light flux $L_2$ of a small intensity that has passed through the light transmission region $P_2$ of the small width is incident on the peripheral portion of the objective lens 5.

Figure 3:
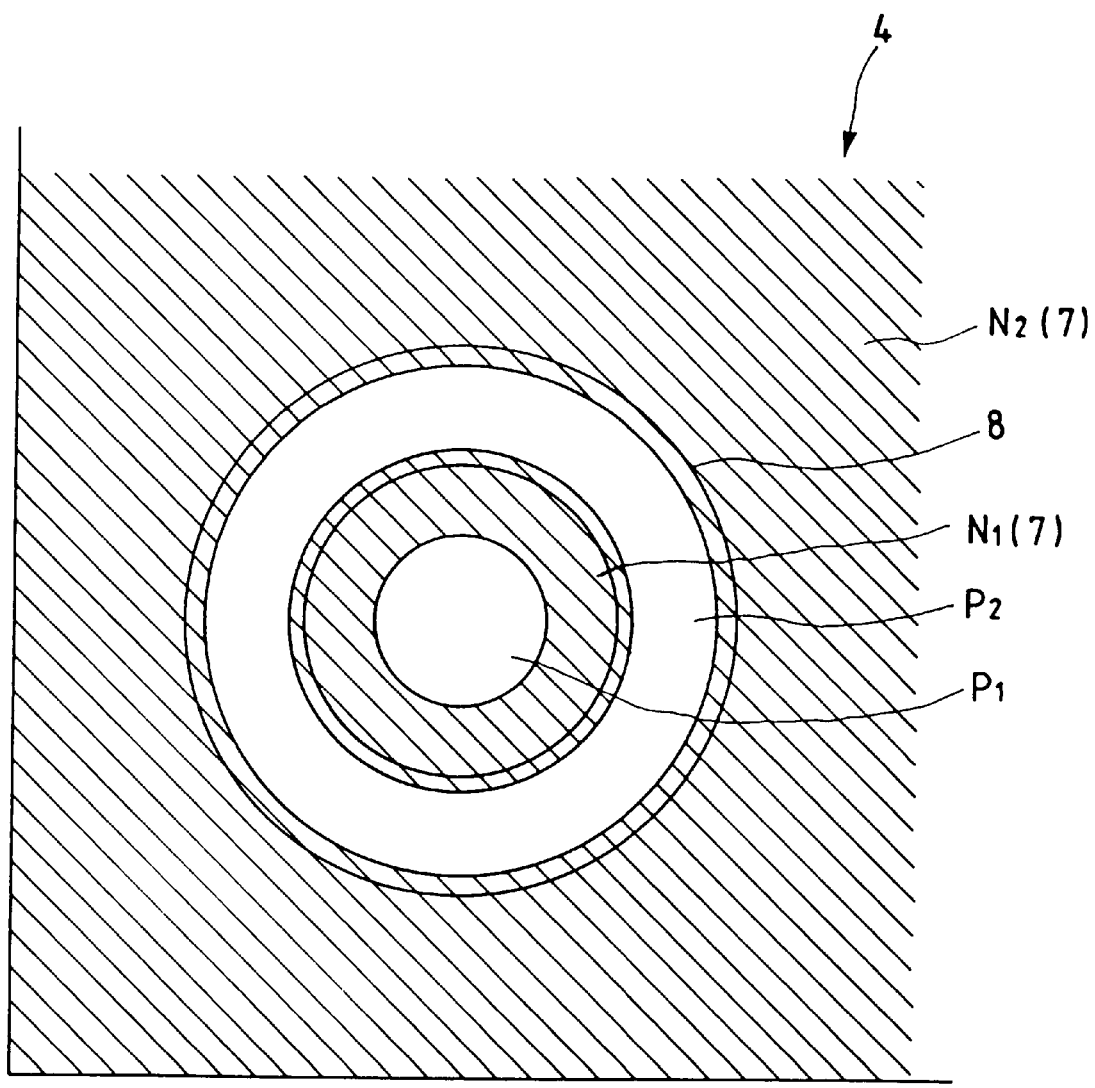
FIG. 3 is a plan view showing the structure of the beam distribution shifter provided in the light beam-forming apparatus.

The light transmission regions $P_1$, $P_2$ and the light blocking region $N_1$ sandwiched by them have spot-like patterns as shown in, for example, FIG. 3, and the machining sizes of these regions are set to be smaller than the values of a product of limit sizes of spots of light beams multiplied by the magnification (M) of the objective lens 5.

That is, the diameter (a) of the light transmission region $P_1$, the width (b) of the light transmission region $P_2$ and the width (c) of the light blocking region $N_1$ are, for example, about $a \approx 0.2 \ \mu m \times M$, $b \leq 0.2 \ \mu m \times M$, $c \approx 0.1 \ \mu m \times M$.

A phase shifter 8 composed of a thin transparent film is provided on the surface of one ($P_2$) of the above light transmission regions $P_1$, $P_2$ so that the light flux $L_1$ that has passed through the light transmission region $P_1$ and the light flux $L_2$ that has passed through the light transmission region $P_2$ will have opposite phases to each other.

In order to render the phases of the light fluxes $L_1$, $L_2$ that have passed through the light transmission regions $P_1$, $P_2$ to be opposite to each other, the thickness (d) of the thin film material constituting the phase shifter 8 is set to substantially satisfy the following relationship:

$$d = \lambda/2(n-1)$$

where n denotes the refractive index of the thin film material, and $\lambda$ denotes the wavelength of the light.

When, for instance, $n = 1.5$ and $\lambda = 458$ nm, d is set to be about 458 nm.

To form the beam distribution shifter 4, first, the light blocking film 7 comprising a thin metal film such as chromium is deposited by sputtering on the whole surface of the glass substrate 6 and is then patterned by the electron ray lithography technology thereby to form light blocking regions $N_1$, $N_2$ and light transmission regions $P_1$, $P_2$.

Next, the whole surface of the glass substrate 6 is spin-coated with a transparent thin film such as a spin on glass (SOG), and this thin film is patterned by the optical lithography technology thereby to form a phase shifter 8 on the surface of the light transmission region $P_2$.

The size and position of the beam distribution shifter 4 vary to some extent depending upon the purpose of use of the light beam to be formed. For instance, when a photoresist applied to the surface of the sample 2 is to be spot-exposed, an operation to increase the focus margin in the direction of height of the sample 2 becomes necessary.

The process in which the projected image of the beam distribution shifter 4 is formed as a fine light beam on the surface of the sample 2 corresponds mathematically to a process in which a distribution function of light intensity having an amplitude and a phase determined by the beam distribution shifter 4 is Fourier-transformed to find a convolution relative to the pupil function of the objective lens 5, and is further inverse Fourier-transformed. The calculation based on this method makes it possible to find a distribution of light intensities on the sample 2.

Increasing the focus margin in the direction of height of the sample 2 corresponds to shifting the above calculation toward the direction of the optical axis to overlap it. Comparison of the calculated result with the calculated result of only the light transmission region $P_1$ at the central portion of the beam distribution shifter 4 indicates that it is equivalent to providing the phase shifter 8 that has a phase and light intensity on the object image plane of the objective lens 5 or is equivalent to imparting a distribution of transmission factors onto the pupil surface of the objective lens 5.

The phase shifter 8 having the former phase and light intensity can be determined by Fourier-transforming the function of light distribution through the light transmission region $P_1$ at the central portion of the beam distribution shifter 4, multiplying it by the cosine of a phase difference obtained by subtracting the change of phase caused by a motion of the image-forming plane from the phase difference of the two images shifted toward the optical axis to find a convolution relative to the pupil function of the objective lens 5, and subjecting it to the inverse Fourier transformation.

The above phase difference is determined by a ratio of the wavelength of the source 1 of light to the numerical aperture of the objective lens 5, and by the distance of movement in the direction of the optical axis. The phase shifter 8 determined by the above system is the one such that the light transmission factor and the phase have functional distributions.

If discretely approximated to simplify the formation of the beam distribution shifter 4, the structure will become similar to the above-mentioned one, and the size and the position can be optimized in correspondence with the source of light and characteristics of the objective lens.

It is also possible to increase the focus margin in the direction of the optical axis by imparting a transmission factor distribution to the pupil surface of the objective lens 5, resulting, however, in a decrease in the intensity of the formed light beam and the efficiency.

Figure 4:
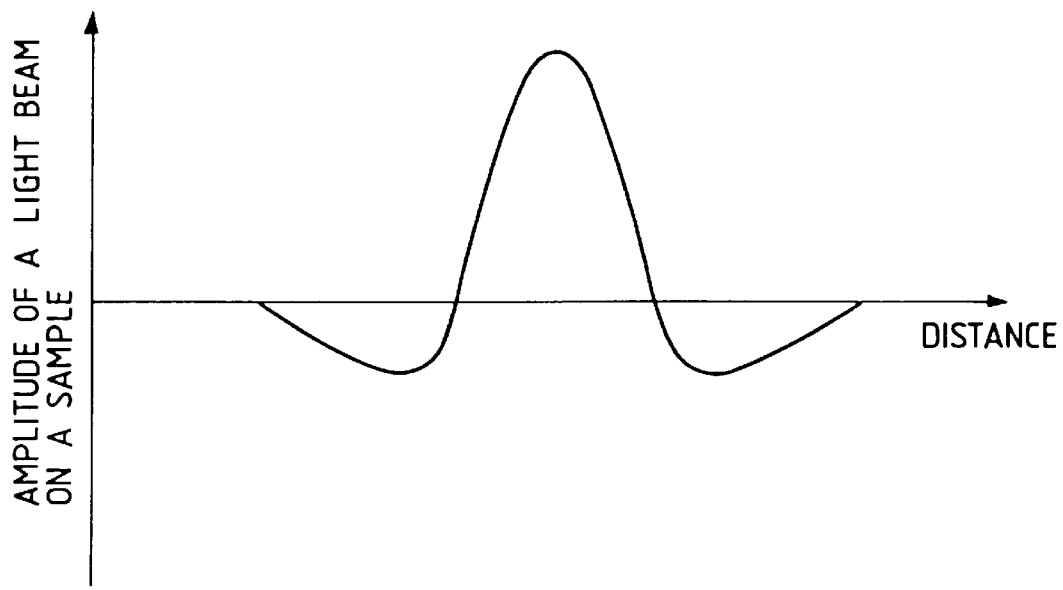
FIG. 4 is a diagram showing the amplitude of a light beam on a sample.

The two light fluxes $L_1$ and $L_2$ that have passed through the light transmission regions $P_1$ and $P_2$ of the beam distribution shifter 4 have opposite phases relative to each other, the light flux $L_1$ at the central portion having an intensity greater than that of the light flux $L_2$ at the periphery. Therefore, the light beam obtained by combining the two light fluxes $L_1$ and $L_2$ has an amplitude on the sample 2 as shown in FIG. 4. That is, the light beam on the sample 2 has a central portion which is prevented from spreading because of interference with the peripheral portion.

Figure 5:
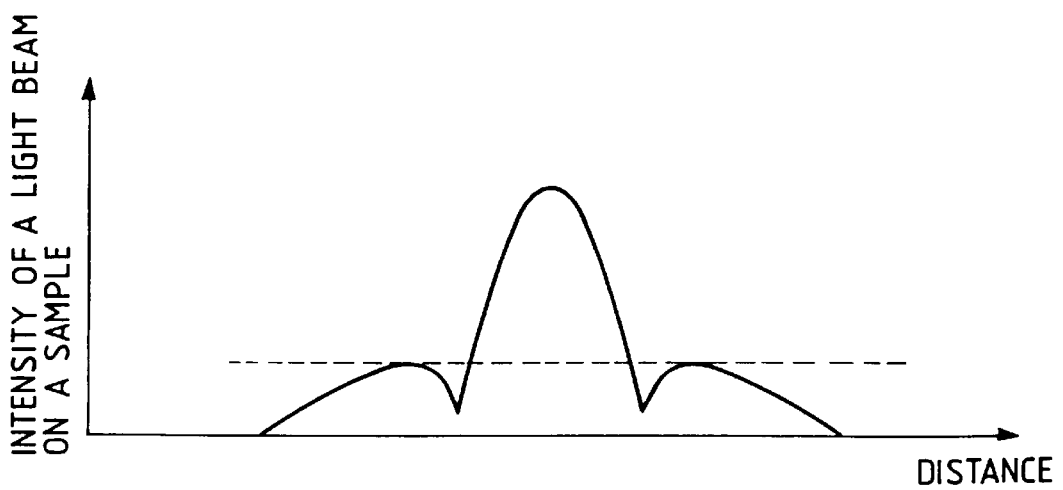
FIG. 5 is a diagram showing the intensity of a light beam on the sample.

Therefore, the width (b) of the light transmission region $P_2$ of the beam distribution shifter 4 is set to be much smaller than the diameter (a) of the light transmission region $P_2$ to eliminate the effect of the beam periphery. Then, as shown in FIG. 5, the diameter of the light beam falling on the surface of the sample 2 becomes virtually smaller than a limit value that is determined by the wavelength of the light and characteristics of the objective lens 5.

According to the method of forming a light beam of this embodiment in which the light emitted from the source 1 of light is divided into two light fluxes $L_1$ and $L_2$ having different intensities and opposite polarities relative to each other through the beam distribution shifter 4 and then the two light fluxes $L_1$, $L_2$ are combined through the objective lens 5 and are projected as a spot-like light beam onto the surface of the sample 2, it is possible to form a light beam having a diameter smaller than a conventional one even when the wavelength of the light emitted from the source 1 of light and characteristics of the objective lens 5 are the same as those of the prior art.

Figure 6:
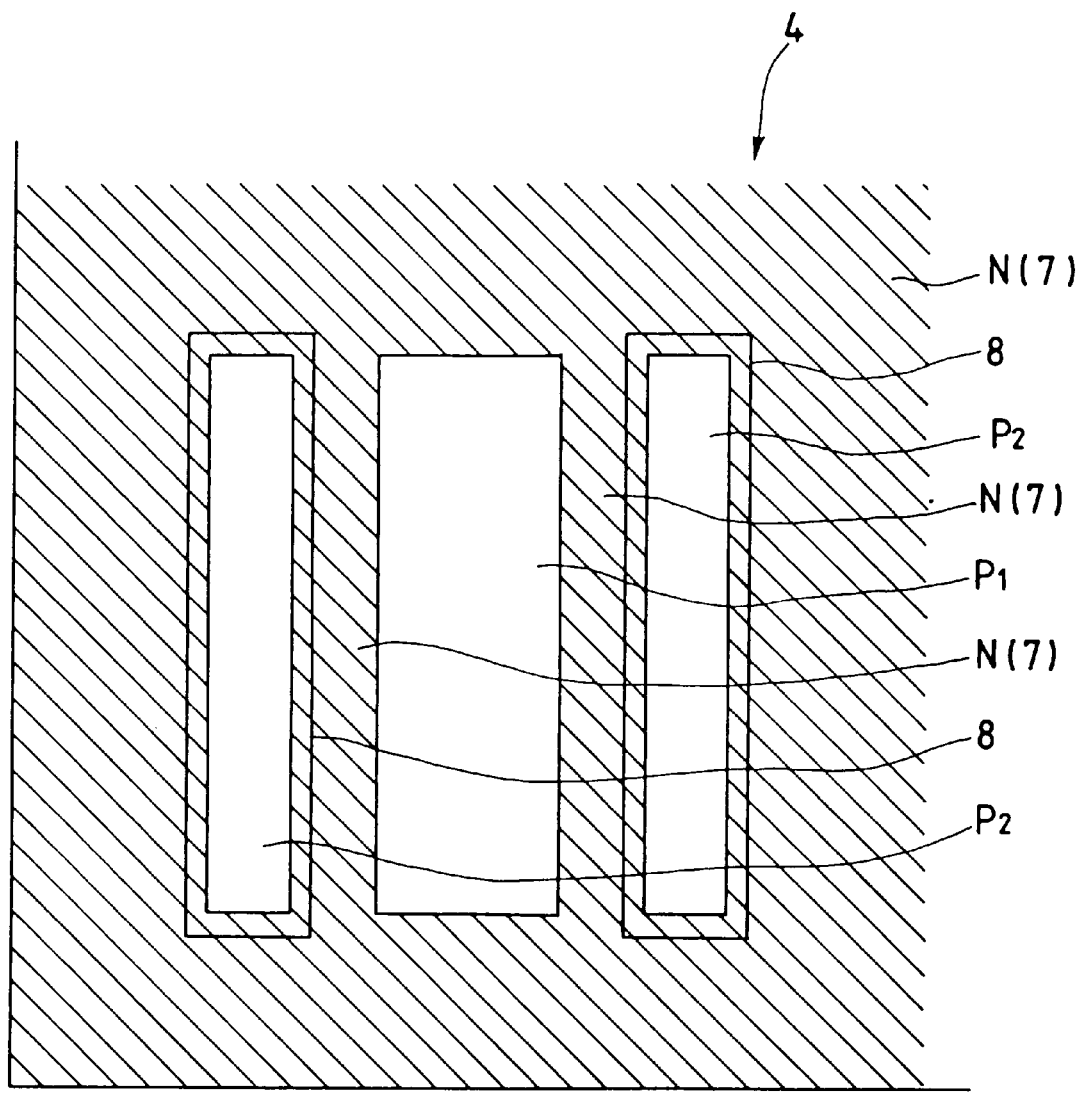
FIG. 6 is a plan view illustrating another structure of the beam distribution shifter.

Here, the patterns of the light transmission region $P_1$, $P_2$ (and light blocking region $N_1$) are not limited to the spot-like ones but may have slit-like patterns as shown in, for example, FIG. 6. In this case, a fine light beam with slit-like patterns can be formed on the sample 2.

Figure 7:
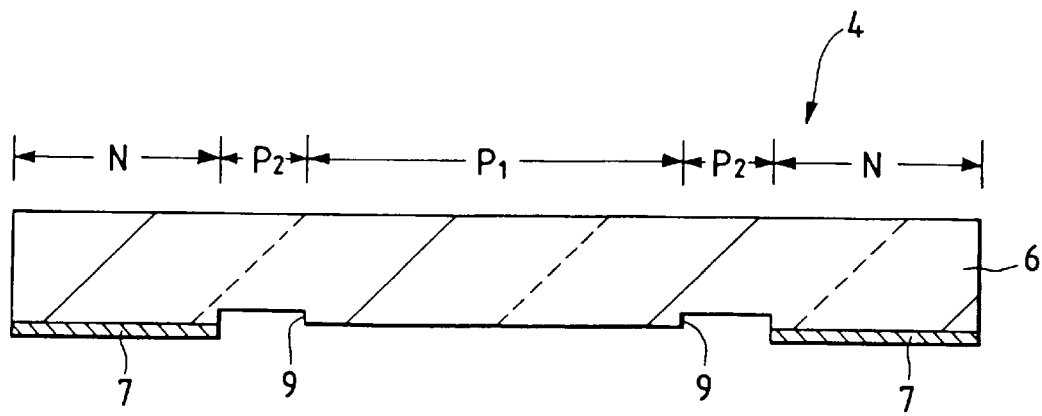
FIG. 7 is a sectional view showing another structure of the beam distribution shifter.
Figure 8:
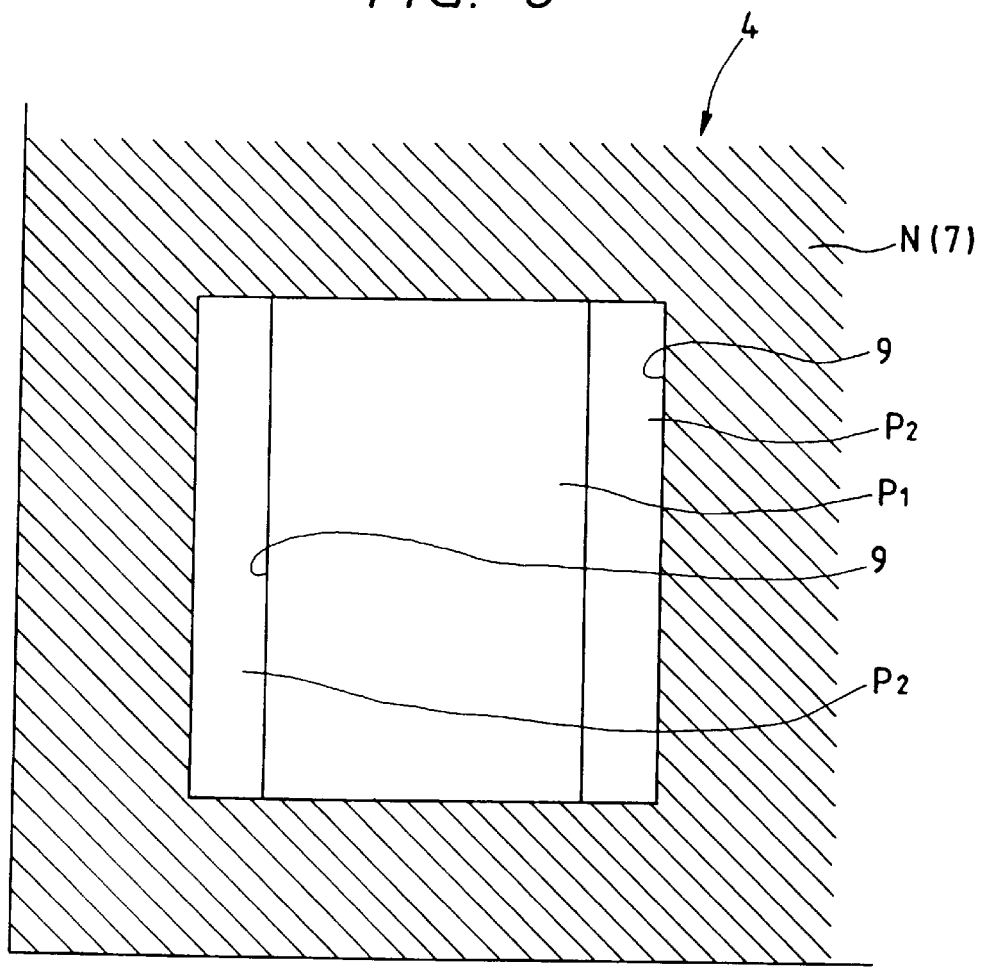
FIG. 8 is a plan view showing the structure of the beam distribution shifter in FIG. 7.

Though the above-mentioned beam distribution shifter 4 has the phase shifter 8 formed on one of the light transmission regions $P_1$ and $P_2$, it is also allowable to form a groove 9 in the light transmission region $P_2$ of the glass substrate 6 as shown in, for example, FIGS. 7 and 8, so that the light flux $L_2$ passing through the groove 9 (light transmission region $P_2$) and the light flux $L_1$ passing through the remaining light transmission region $P_1$ will have phases opposite to each other.

In this case, the depth (d) of the groove 9 must be so set as to substantially satisfy the following relationship:

$$d=\lambda/2(n-1)$$

where n denotes the refractive index of the glass substrate 6, and λ denotes the wavelength of the light.

The above groove 9 can be formed by sputtering using an ion beam or by lithography technology (etching). When the groove 9 is to be formed by sputtering using an ion beam, it is preferable that the surface to be treated of the glass substrate is flattened by plasma treatment using a $CF_4$ gas or a like gas in order to prevent the transmission factor of light from decreasing.

In the foregoing description, the intensity of light flux $L_2$ of the periphery is set to be smaller than the intensity of light flux $L_1$ at the central portion by setting the width of light transmission region $P_2$ in the periphery of the beam distribution shifter 4 to be smaller than the diameter of light transmission region $P_1$ in the central portion. However, the intensity of light flux $L_2$ in the periphery may be decreased by providing a light intensity conversion means between the beam distribution shifter 4 and the objective lens 5. In this case, the diameter of the light transmission region $P_1$ at the central portion may be the same as the width of the light transmission region $P_2$ in the periphery.

In the foregoing description, the two light fluxes $L_1$ and $L_2$ that have passed through the beam distribution shifter 4 are combined together through the objective lens 5 to form a single light beam. It is, however, also possible to form a plurality of light beams. Constitution of the beam distribution shifter 4 for forming a plurality of light beams will be described later in detail.

Figure 9:
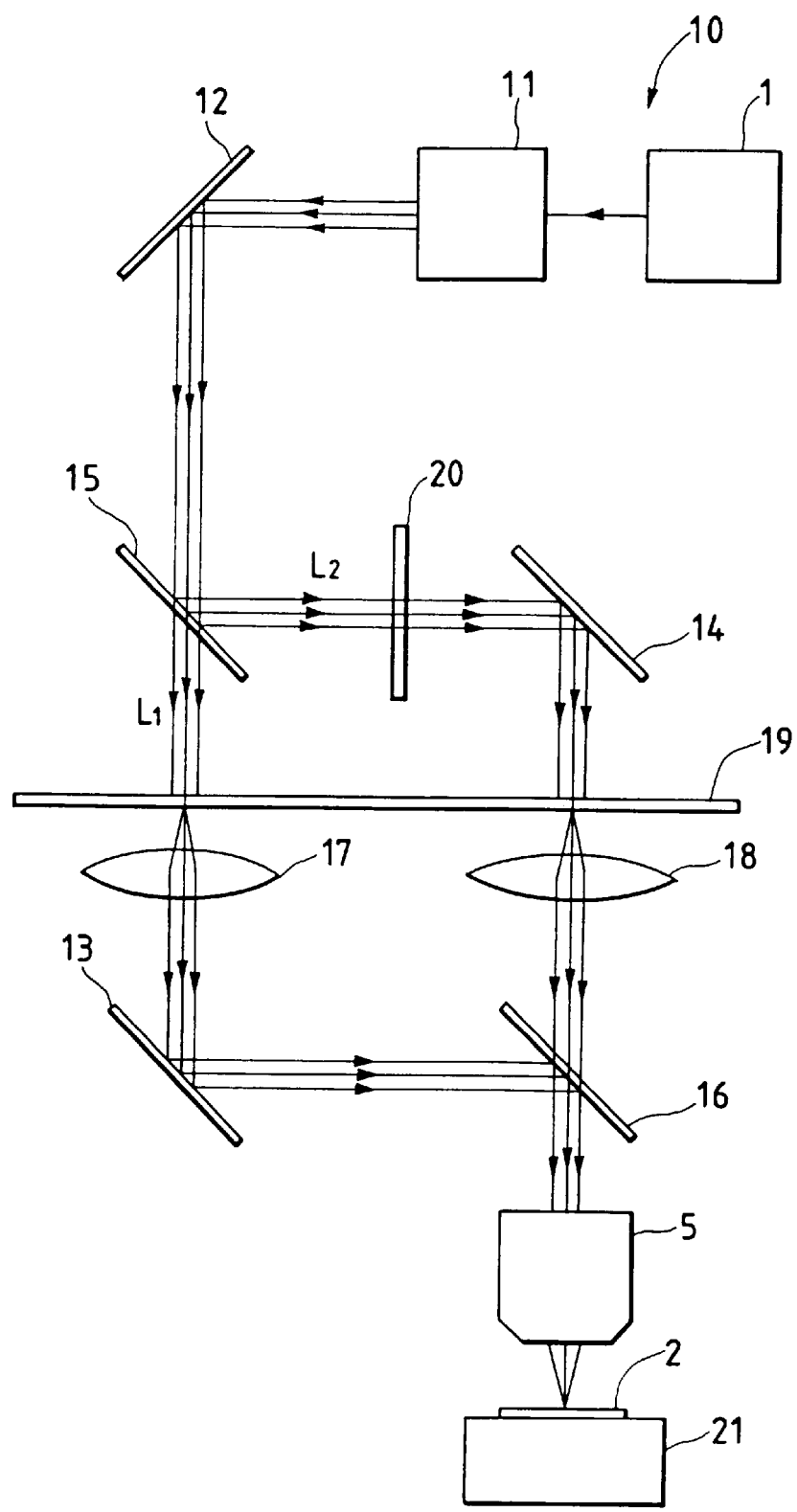
FIG. 9 is a diagram illustrating the structure of the optical system in the light beam-forming apparatus of another embodiment of the present invention.

FIG. 9 shows another optical system of the light beam-forming apparatus 10 of this embodiment.

A beam expander 11, mirrors 12, 13, 14, half-mirrors (or beam splitters) 15, 16, lenses 17, 18 and an objective lens 5 are arranged on an optical path that links the source 1 of light of the optical system to the sample 2. Furthermore, a photomask 19 is located in an alignment system (not shown) of the optical system.

Figure 10:
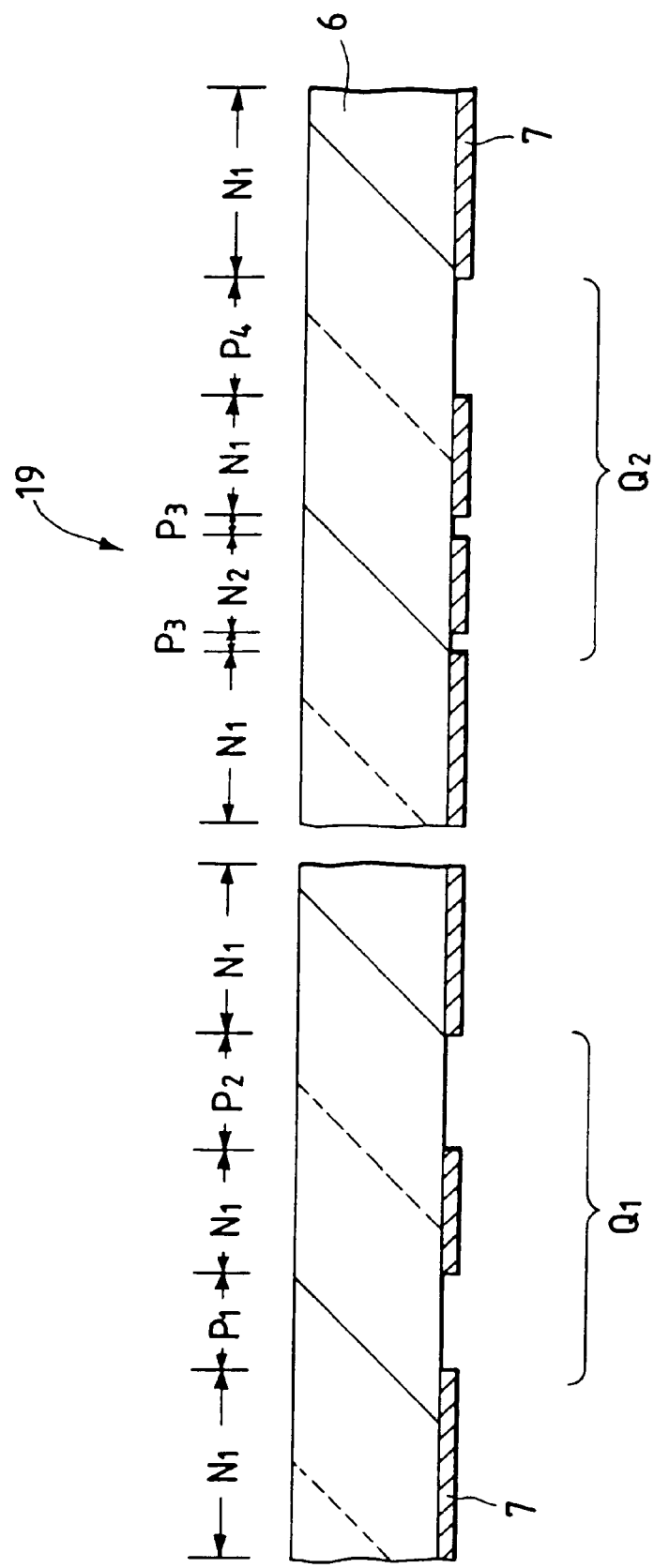
FIG. 10 is a sectional view illustrating major portions in the structure of a photomask provided for the light beam-forming apparatus.

FIG. 10 is a sectional view showing major portions of the photomask 19.

For instance, two patterns $Q_1$ and $Q_2$ are formed on a surface of the photomask 19 which comprises a glass substrate 6 such as of transparent synthetic quartz. The pattern $Q_1$ includes the light transmission regions $P_1$, $P_2$ and the light blocking region $N_1$, and the pattern $Q_2$ includes the light transmission regions $P_3$, $P_4$ and the light blocking regions $N_1$, $N_2$.

The light blocking regions $N_1$ and $N_2$ are constituted by the light blocking film 7 of a thin metal film such as of chromium. The above pair of patterns $Q_1$ and $Q_2$ are arranged at predetermined portions a predetermined distance apart.

Figure 11:
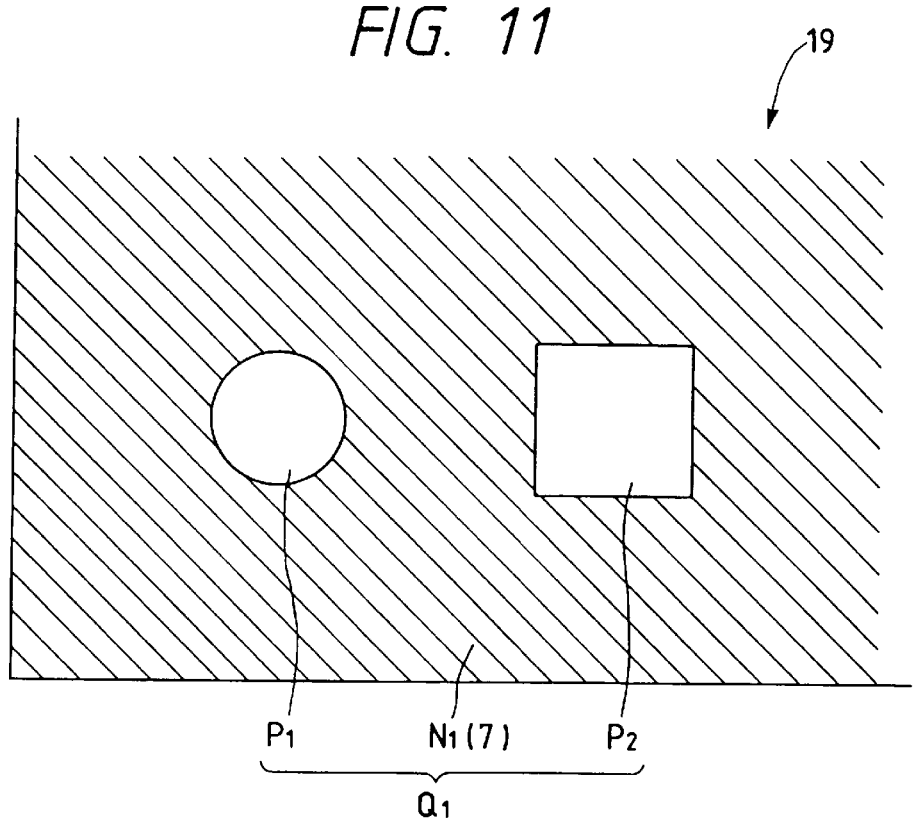
FIG. 11 is a plan view showing a first pattern formed on the photomask.
Figure 12:
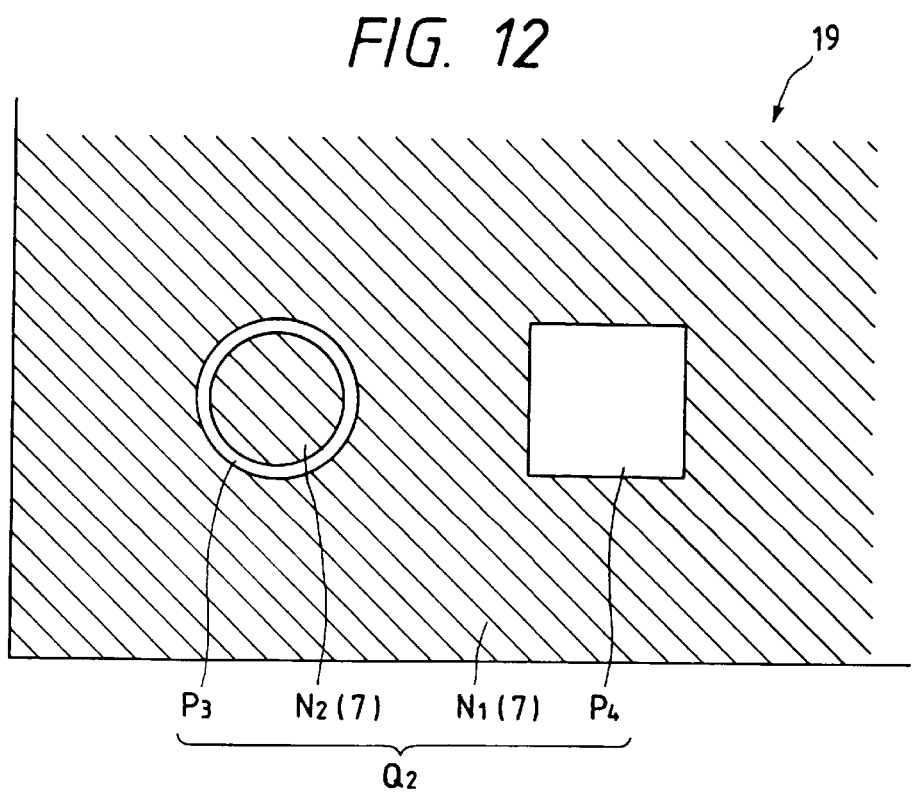
FIG. 12 is a plan view showing a second pattern formed on the photomask.

FIG. 11 is a plan view of the above pattern $Q_1$ and FIG. 12 is a plan view of the pattern $Q_2$.

As shown in these drawings, the light transmission region $P_3$ of the pattern $Q_2$ has a diameter greater than that of the light transmission region $P_1$ of the pattern $Q_1$ and contains therein the light blocking region $N_2$ of a size nearly the same as that of the light transmission region $P_1$.

Furthermore, the light transmission region $P_2$ in the pattern $Q_1$ and the light transmission region $P_4$ in the pattern $Q_2$ have the same shape and size. Moreover, the distance from the center of light transmission region $P_1$ of the pattern $Q_1$ to the center of light transmission region $P_2$ is the same as the distance from the center of light blocking region $N_2$ of the pattern $Q_2$ to the center of light transmission region $P_4$. The pair of light transmission regions $P_2$ and $P_4$ are used as positioning marks for registering the light transmission region $P_1$ with the light transmission region $P_3$ with high precision.

Described below is how to form a light beam using the light beam-forming apparatus 10 equipped with the above optical system.

Referring to FIG. 9, the light emitted from the source 1 of light is expanded through the beam expander 11, reflected by the mirror 12 in a direction perpendicular to the main surface of the photomask 19, and is then divided into two light fluxes $L_1$ and $L_2$ by the half-mirror 15.

One ($L_1$) of the two light fluxes $L_1$ and $L_2$ travels straight to fall on a predetermined portion of the photomask 19. The other light flux $L_2$ travels in a direction perpendicular to the light flux $L_1$, is inverted in phase by 180 degrees by a phase-shifting means 20 disposed on the optical path, is reflected by the mirror 14 in a direction perpendicular to the main surface of the photomask 19, and falls on another portion of the photomask 19.

In this case, the photomask 19 is so positioned that one ($L_1$) of the two light fluxes $L_1$ and $L_2$ is incident on the pattern $Q_1$ formed on the photomask 19 and the other flux ($L_2$) is incident on the pattern $Q_2$.

The phase-shifting means 20 disposed on the optical path of light flux $L_2$ has an electrooptical element consisting of a crystal of the tetragonal system of, for example, potassium dihydrogenphosphate which, when an electric field is applied thereto, exhibits a refractive index that changes in proportion to the electric field due to the Pockels effect. That is, by applying a suitable electric field to the electrooptical element, the phase of the light $L_2$ that has passed through the phase-shifting means 20 can be inverted by 180 degrees.

As the electrooptical element in the phase-shifting means 20, there can be used a uniaxial 3m crystal (trigonal system) such as $LiTaO_3$ or $LiNbO_3$ in addition to the above potassium dihydrogenphosphate. When an electric field is applied in a direction at right angles to the incident light, these crystals change the phase of light.

The light flux $L_1$ that has passed through the light transmission regions $P_1$, $P_2$ of pattern $Q_1$ formed on the photomask 19 and the light flux $L_2$ that has passed through the light transmission regions $P_3$, $P_4$ pass through the lenses 17 and 18, are combined by the mirror 13 and half-mirror 16, further pass through the objective lens 5, and are formed into a fine spot-like light beam to fall on the surface of the sample 2 positioned on an XY table 21.

When the photomask 19 is correctly positioned and the phase difference is correctly adjusted between the two light fluxes $L_1$ and $L_2$, the light flux $L_1$ that has passed through the light transmission region $P_2$ of the photomask 19 and the light flux $L_2$ that has passed through the light transmission region $P_4$ are combined and then interfere with each other so as to be completely extinguished. Therefore, the projected images of the light transmission regions $P_2$ and $P_4$ are not formed on the surface of the sample 2.

That is, by detecting the presence of projected images of light transmission regions $P_2$, $P_4$ (positioning marks) on the sample 2, it is possible to easily determine whether the photomask 19 is correctly positioned and whether the phase difference between the two light fluxes $L_1$ and $L_2$ is correctly adjusted.

Figure 13:
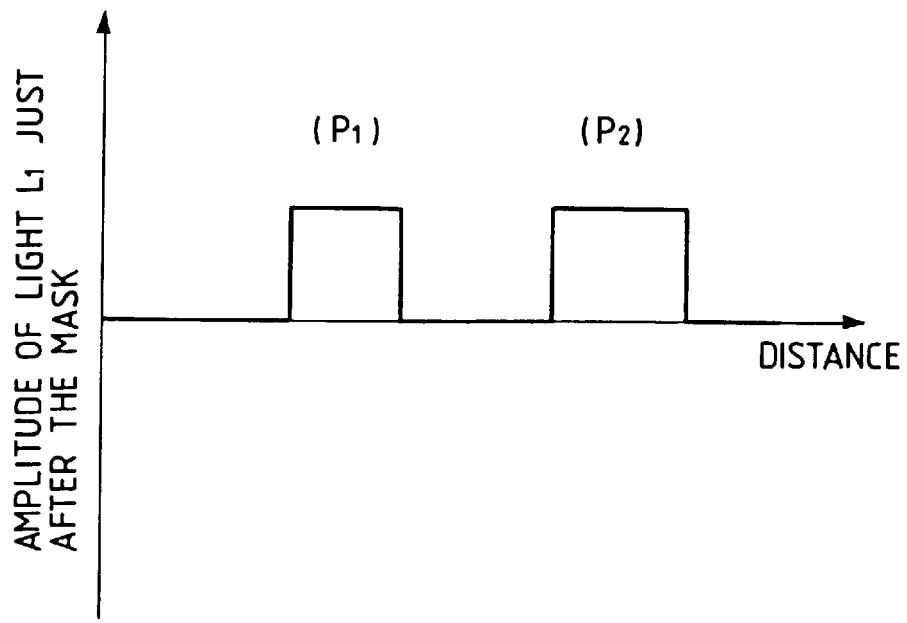
FIG. 13 is a diagram showing the amplitude of light just after having passed through the first pattern.
Figure 14:
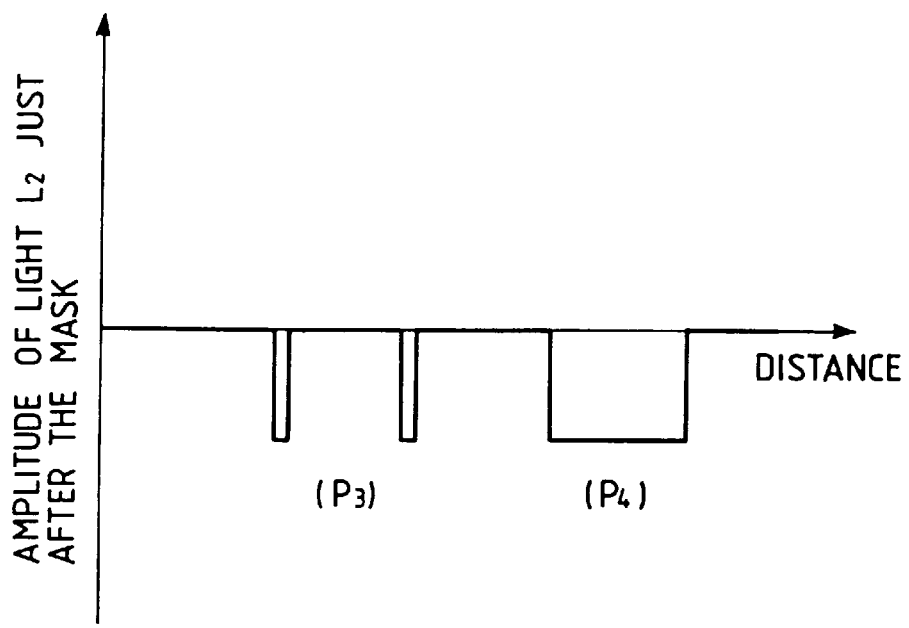
FIG. 14 is a diagram showing the amplitude of light just after having passed through the second pattern.

FIG. 13 shows the amplitude of the light flux $L_1$ just after it has passed through the light transmission regions $P_1$, $P_2$ of the pattern $Q_1$ formed on the photomask 19, and FIG. 14 shows the amplitude of the light flux $L_2$ just after it has passed through the light transmission regions $P_3$, $P_4$ of the pattern $Q_2$.

As mentioned earlier, the light transmission region $P_3$ has a diameter greater than that of the light transmission region $P_1$ and contains therein the light blocking region $N_2$ of nearly the same size as the light transmission region $P_1$. Moreover, the light flux $L_1$ that has passed through the light transmission region $P_2$ and the light flux $L_2$ that has passed through the light transmission region $P_4$ interfere with each other after they are combined so as to be completely extinguished.

Figure 15:
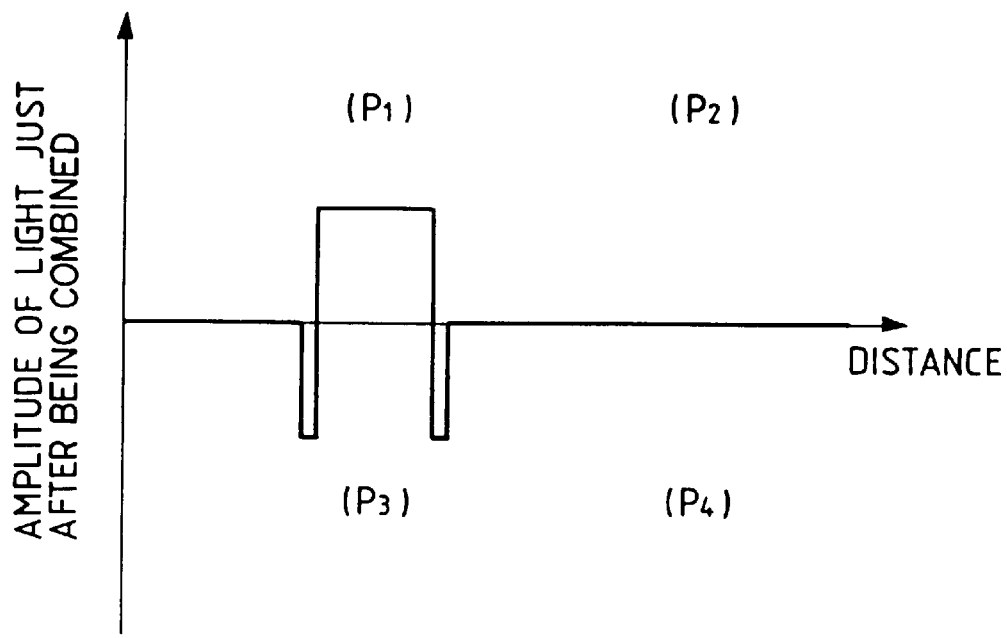
FIG. 15 is a diagram showing the amplitude of light just after being combined.
Figure 16:
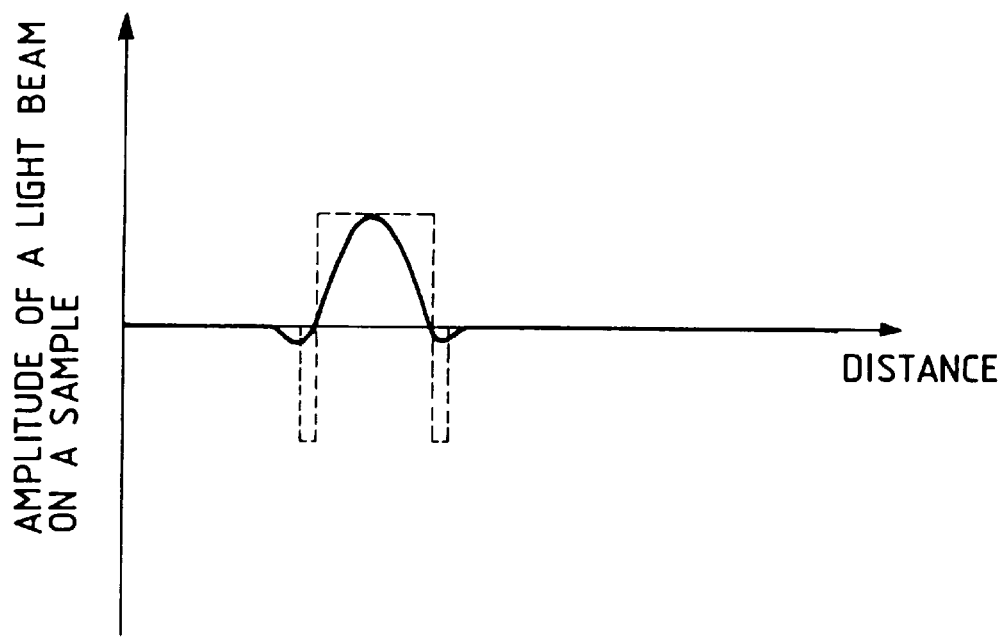
FIG. 16 is a diagram showing the amplitude of a light beam on a sample.

Therefore, the amplitude of the light beam just after light fluxes $L_1$ and $L_2$ are combined becomes as shown in FIG. 15, and the amplitude of the light beam projected onto the surface of the sample 3 becomes as shown in FIG. 16. That is, the light beam on the surface of the sample 2 has an amplitude whose central portion is prevented from spreading because of the interference with the periphery thereof.

Figure 17:
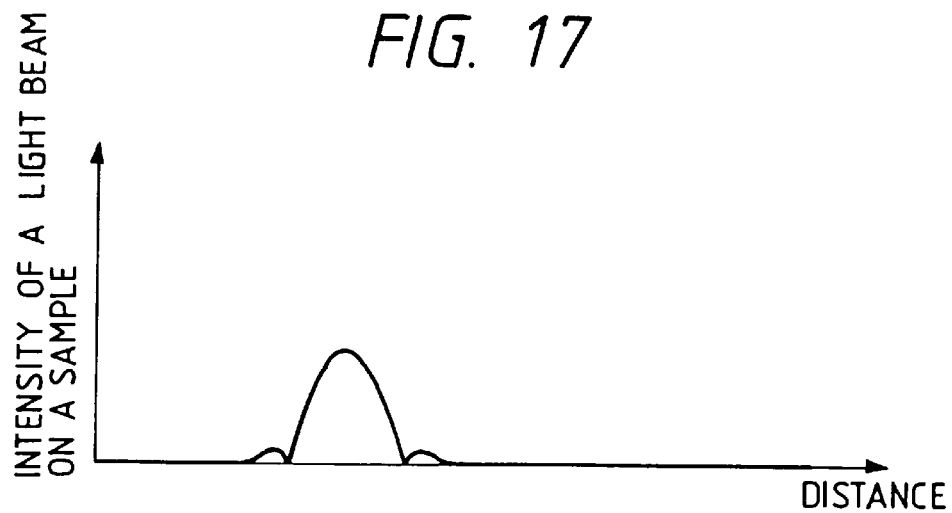
FIG. 17 is a diagram showing the intensity of a light beam on the sample.

Therefore, by setting the difference between the diameters of the pair of light transmission regions $P_1$ and $P_3$ to eliminate the effect of the beam periphery, the diameter of the light beam falling on the surface of the sample 2 can be set to be substantially smaller than the limit value determined by the wavelength of the light and characteristics of the objective lens 5 as shown in FIG. 17.

That is, it is possible to form a light beam having a diameter which is smaller than that of a conventional light beams even when the wavelength of the light emitted from the source 1 of light and characteristics of the objective lens 5 are the same as those of the prior art.

In the foregoing description, the phase-shifting means 20 is disposed on one optical path ($L_2$) of the two light fluxes $L_1$ and $L_2$ divided by the half-mirror 15 in order to render the phases of the two light fluxes $L_1$ and $L_2$ to be opposite to each other. It is, however, also allowable to provide an optical path length varying means on either optical path of the two light fluxes $L_1$, $L_2$ divided by the half-mirror 15.

Though the above description deals with forming a spot-like light beam, it is further possible to form light beams of a slit-like shape or any other shape by changing the patterns of the pair of light transmission regions $P_1$, $P_3$ on the photomask 19.

Embodiment 2

Figure 18:
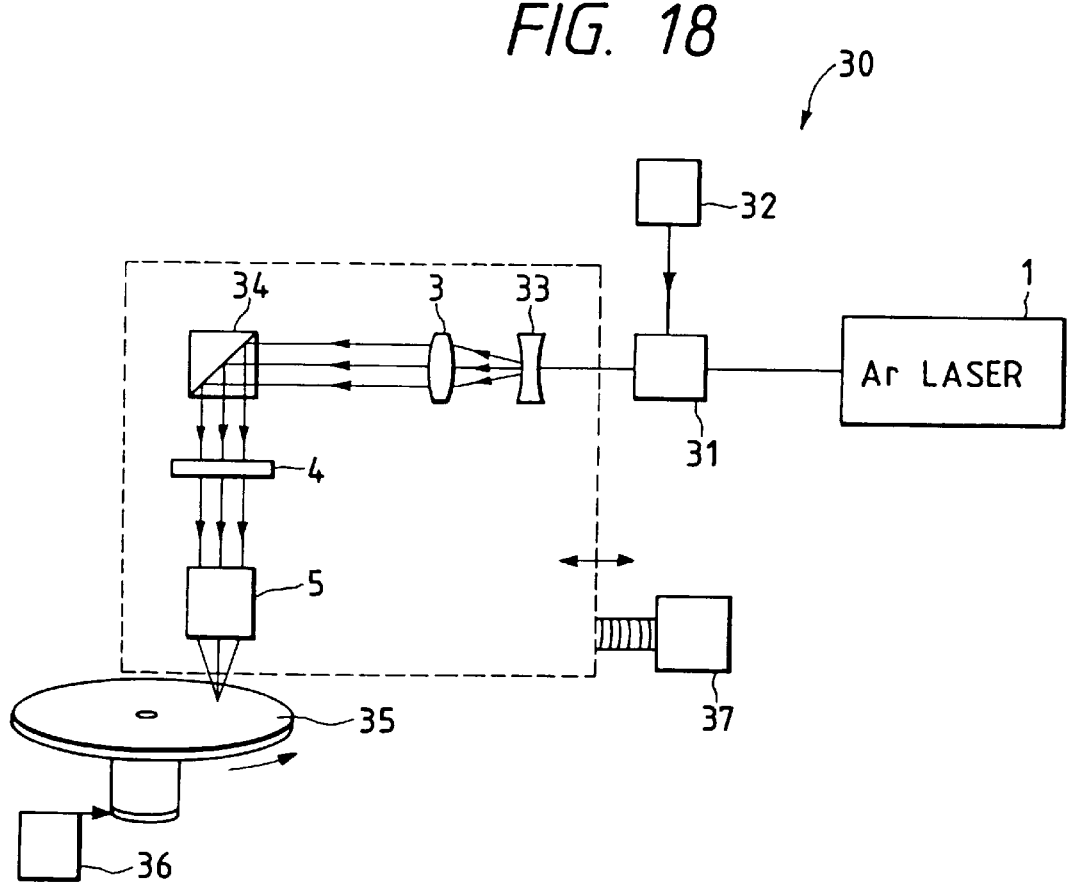
FIG. 18 is a diagram illustrating the whole structure of an optical disk device using the light beam-forming method of the present invention.

FIG. 18 illustrates an optical disk device 30 which utilizes the method of forming a light beam of the aforementioned Embodiment 1.

The optical disk device 30 is for writing data onto an optical disk according to the presence of a trace of spot beam irradiation on the optical disk.

An argon laser beam emitted from the source 1 of light passes through a light modulator 31 at which the beam is modulated by an electric signal from a signal source 32, expanded by a lens 33, transformed into a parallel beam through a condenser lens 3, and is reflected by a polarized beam splitter 34 in a direction perpendicular to the main surface of a glass disk 35 that is a mother disk for an optical disk.

The beam distribution shifter 4 described in the Embodiment 1 is disposed on the optical path between the polarized beam splitter 34 and the objective lens 5. The argon laser beam that has passed through the beam distribution shifter 4 is divided into two light fluxes $L_1$ and $L_2$ having opposite phases relative to each other, one ($L_1$) of them falling on the central portion of the objective lens 5 and the other one ($L_2$) falling on the peripheral portion thereof.

The two light fluxes $L_1$ and $L_2$ are combined together as they pass through the objective lens 5 to form, for example, a spot-like light beam which falls on the surface of the disk 35. As for the light beam, the initial two light fluxes $L_1$ and $L_2$ have phases opposite to each other, and the intensity of light flux $L_1$ of the central portion is greater than the intensity of light flux $L_2$ of the peripheral portion. Therefore, the central portion of the beam is prevented from spreading because of interference with the periphery.

The glass disk 35 that is the mother disk for the optical disk is coated with a photoresist on the surface thereof and is rotated at a constant speed, of for example, about 1800 rpm by a servo motor 36. Further, the light beam is deflected in the X- and Y-directions by a motor 37 provided in the optical system.

Figure 19:
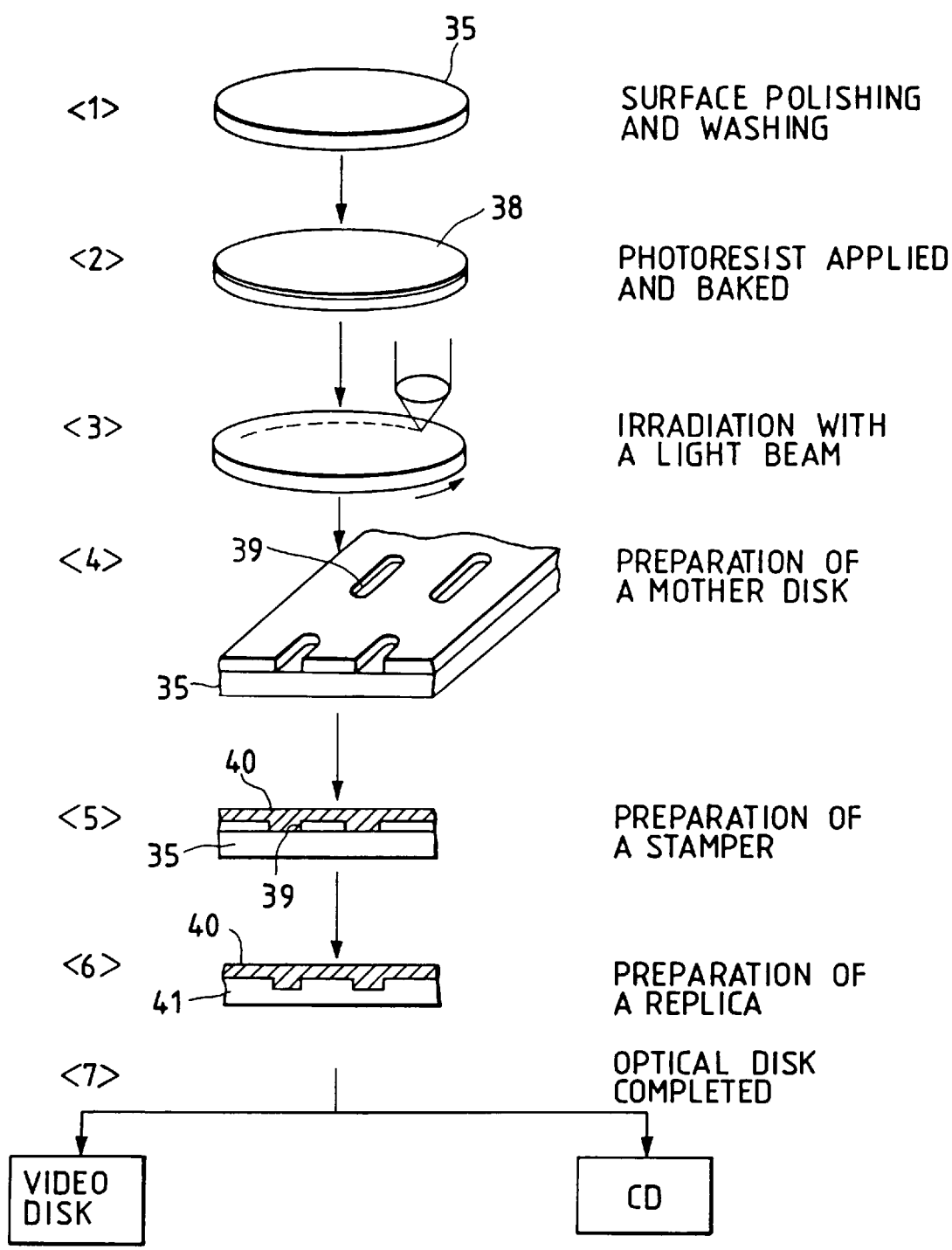
FIG. 19 is a flow diagram illustrating a method of manufacturing an optical disk for the optical disk device.

FIG. 19 is a diagram showing the manufacturing flow of fabricating the optical disk using the optical disk device 30.

To fabricate the optical disk using the optical disk device 30, first, a glass disk 35 that serves as the mother disk for the optical disk is prepared and its surface is polished and washed [1]. Then, the surface of the glass disk 35 is spin-coated with a three-layer photoresist 38 which consists of a photoresist (lower layer), a spin-on-glass (intermediate layer) and a photoresist (upper layer), and the glass disk is baked at a predetermined temperature [2].

Next, the glass disk 35 is positioned on the optical disk device 30 and is irradiated with the light beam at a predetermined portion on the surface thereof while being rotated at a predetermined speed in order to form a latent image on the photoresist 38 [3]. The photoresist 38 is then developed whereby traces of irradiation with the central portion of the light beam are left on the portions of the upper photoresist layer that has been irradiated with the light beam and slight traces of irradiation with the periphery of the light beam having a small intensity are left thereon.

Next, the intermediate layer of the spin-on-glass is etched using the upper layer of photoresist as a mask, and the photoresist of the lower layer is etched using the spin-on-glass as a mask to form fine pits 39 in the lower layer of photoresist that has been irradiated with the light beam, thereby preparing the mother disk of the optical disk [4].

The amount of light beam irradiation, developing conditions of the photoresist, and etching conditions are optimized to leave only the trace of irradiation with the central portion of the light beam on the lower layer of photoresist that has been irradiated with the light beam in order to form pits 39 that are finer than conventional ones even when the wavelength of the light and characteristics of the objective lens are the same as those of the prior art.

Next, the surface of the thus obtained mother disk is plated with nickel to prepare a stamper 40 that serves as a metal die for the optical disk [5], and then a synthetic resin is permitted to flow onto the stamper 40 to prepare a replica 41 of the optical disk [6]. A reflection film and a protection film are finally deposited on the surface of the replica 41 to complete the optical disk such as a video disk or a CD (compact disk) [7].

In the foregoing description, the surface of the glass disk coated with the three-layer photoresist is irradiated with the light beam. It is, however, also possible to deposit a thin metal film on the surface of the glass disk by, for example, sputtering and then apply one layer of photoresist thereon followed by irradiation with the light beam. In this case, the lower thin metal film is etched by using the photoresist as a mask to form pits.

In this case, the amount of light beam irradiation, developing conditions of the photoresist and etching conditions are optimized to leave only the trace of irradiation with the central portion of the light beam on the thin metal film that has been irradiated with the light beam in order to form pits that are finer than conventional ones even when the wavelength of the light and characteristics of the objective lens are the same as those of the prior art.

According to the optical disk device 30 of this embodiment as described above, the data recording density of the optical disk can be greatly increased.

The method of forming the light beam of the present invention can be adapted not only to the above optical disk device 30 but also to an optomagnetic disk device that records data onto an optomagnetic disk by using a light beam and a magnetic field in combination.

An optomagnetic disk device is one in which an optomagnetic recording material such as Tb—Fe, Tb—Fe—C, or Gd—Tb—Fe is deposited on a substrate and is magnetized in a predetermined direction, and the data is recorded by utilizing the phenomenon that when the substrate is irradiated with a light beam and is heated, the direction of magnetization of the irradiated portion is inverted by the surrounding magnetic field.

To read out the data, the intensity of light passing through a polarizing plate provided on the optical path of reflected light is detected by utilizing the Kerr effect in which when the recorded portion is irradiated with a light beam as a spot having weak linear deflection, the plane of polarization of the reflected light rotates due to the direction of magnetization.

The data recording density of the optomagnetic disk can therefore be greatly increased by irradiating the optomagnetic recording material with a fine light beam that is formed according to the present invention.

Embodiment 3

Figure 20:
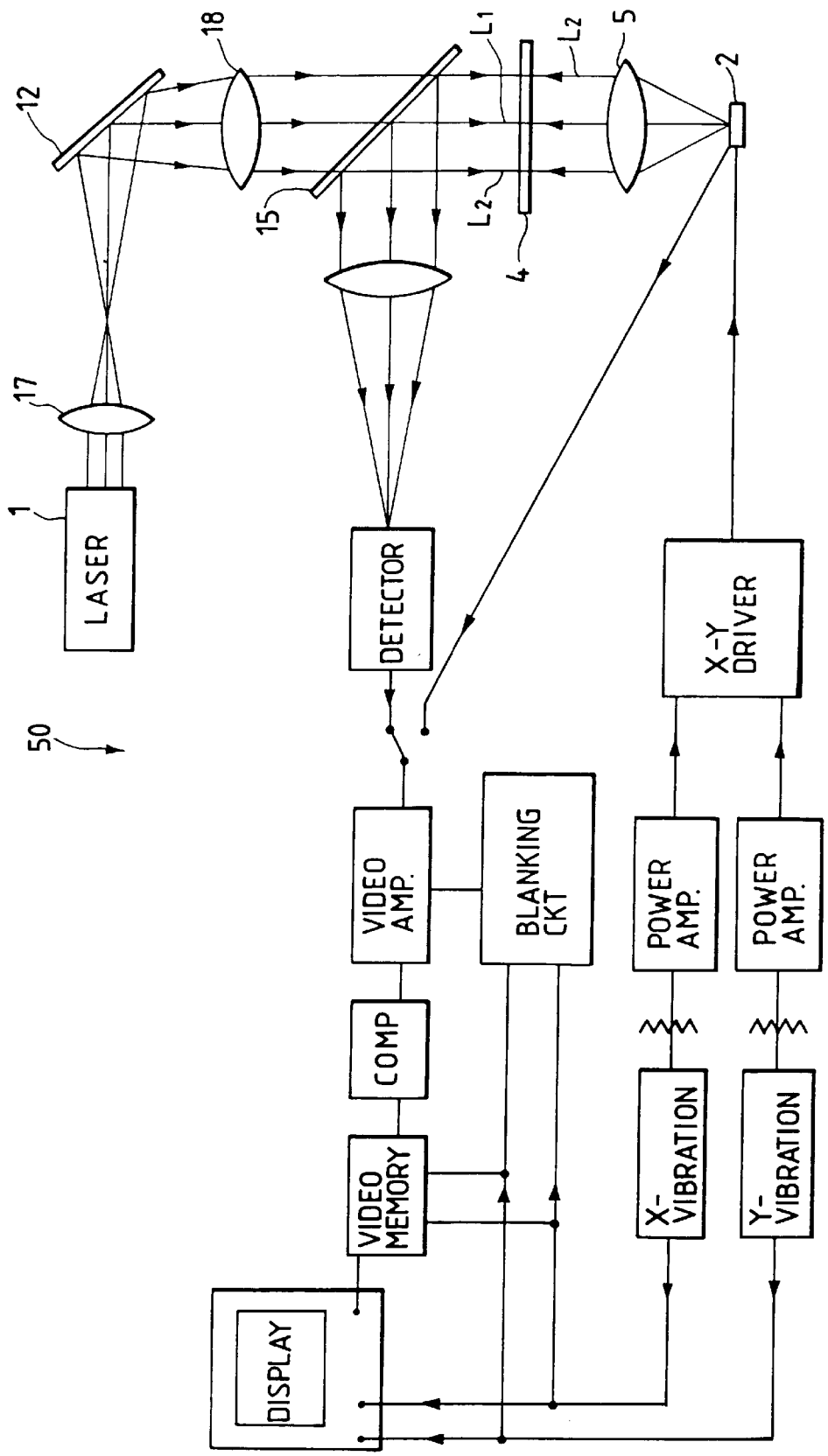
FIG. 20 is a diagram illustrating the whole structure of an optical microscope apparatus using the optical beam-forming method of the present invention.

FIG. 20 illustrates an optical microscope apparatus 50 which utilizes the method of forming a light beam of the present invention.

The optical microscope apparatus 50 is of a scanning type for observing the surface profile of a sample 2 or internal defects of the sample 2 by detecting light projected onto the sample 2 and reflected therefrom or by detecting a light-induced current in the sample.

The optical microscope apparatus 50 is equipped with an optical system of a confocal type. The sensor for detection may be an image sensor such as a CCD (charge coupled device) or a detector that detects a current excited by light in the sample 2 due to irradiation with a laser beam.

The laser beam emitted from a source 1 of light passes through a lens 17, is reflected by a mirror 12 in a direction perpendicular to the sample 2, is transformed into a parallel beam by a lens 18, and is focused by an objective lens 5 into, for example, a spot-like laser beam which falls on the surface of the sample 2.

A beam distribution shifter 4 constituted in the same manner as that of the aforementioned Embodiment 1 is disposed on an optical path that links the lens 18 to the objective lens 5. The laser beam that has passed through the beam distribution shifter 4 is divided into two light fluxes $L_1$ and $L_2$ having opposite phases relative to each other, one ($L_1$) of them falling on the central portion of the objective lens 5 and the other one ($L_2$) falling on the peripheral portion.

The beam distribution shifter 4 is disposed on the object image surface of the objective lens 5, and the sample 2 is disposed on the image-forming surface of the objective lens 5. Therefore, the projected image of the beam distribution shifter 4 forms an image as a fine light beam on the surface of the sample 2.

The laser beam falling on the surface of the sample 2 includes the initial light fluxes $L_1$ and $L_2$ that have opposite phases relative to each other, and the intensity of light flux $L_1$ falling on the central portion of the objective lens 5 is greater than the intensity of light flux $L_2$ falling on the peripheral portion. Therefore, the central portion of the laser beam is prevented from spreading because of the interference with the periphery.

Since the effect of the beam periphery is eliminated, the diameter of the laser beam falling on the surface of the sample 2 can be made substantially smaller than the limit value that is determined by the wavelength of the laser beam and characteristics of the objective lens 5. It is therefore made possible to greatly enhance the resolution of the optical microscope apparatus 50 even when the wavelength of the laser beam and characteristics of the objective lens 5 are the same as those of the prior art.

Embodiment 4

Figure 21:
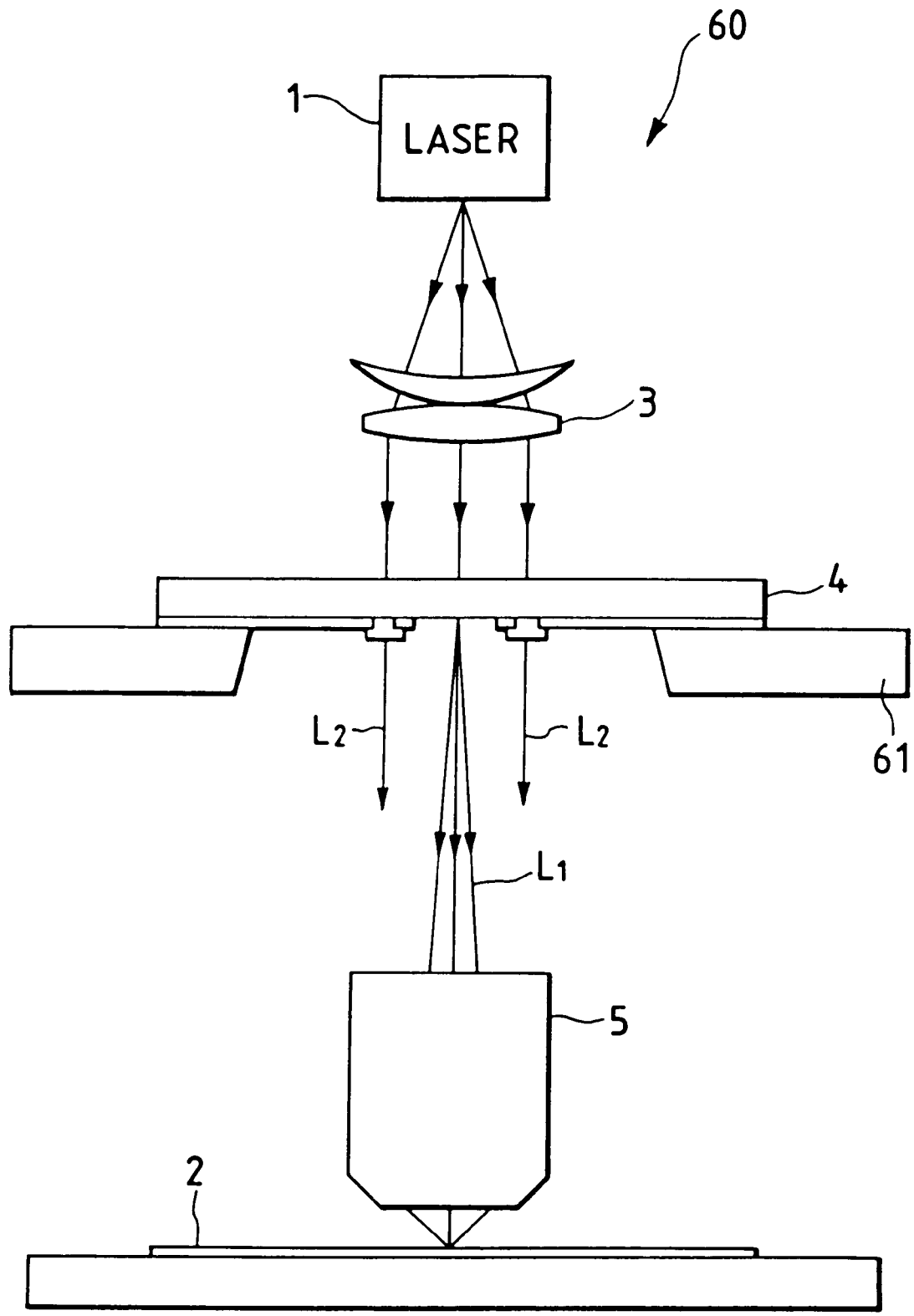
FIG. 21 is a diagram showing the structure of an optical system in a laser beam machining apparatus using the light beam-forming method of the present invention.

FIG. 21 shows an optical system of a laser beam machining apparatus 60 which utilizes the method of forming a light beam of the present invention.

The basic constitution of this optical system is the same as that of Embodiment 1. That is, a condenser lens 3, an aperture 61 equipped with a beam distribution shifter 4, and an objective lens 5 are arranged on an optical path that links a source 1 of light to a sample 2.

The source 1 of light is a source of a laser beam such as a YAG laser having a short wavelength, high output and improved stability. The condenser lens 3 transforms a laser beam emitted from the source 1 of light into a parallel laser beam which falls on the beam distribution shifter 4.

The beam distribution shifter 4 divides the parallel laser beam obtained through the condenser lens 3 into a light flux $L_1$ that falls on the central portion of the objective lens 5 and a light flux $L_2$ that falls on the peripheral portion, and renders their phases to be opposite to each other. The objective lens 5 combines the light fluxes $L_1$ and $L_2$ that have passed through the beam distribution shifter 4 to form a laser beam which falls on the surface of the sample 2.

The beam distribution shifter 4 mounted on an aperture 61 is arranged on the object image surface of the objective lens 5. That is, the objective lens forms the projected image of the beam distribution shifter 4 as a fine laser beam on the surface of the sample 2.

Though not shown, the beam distribution shifter 4 may be provided with a finely moving mechanism and an image processing mechanism such as pattern matching in order to improve the precision of alignment between the sample 2 and the laser beam.

Figure 22:
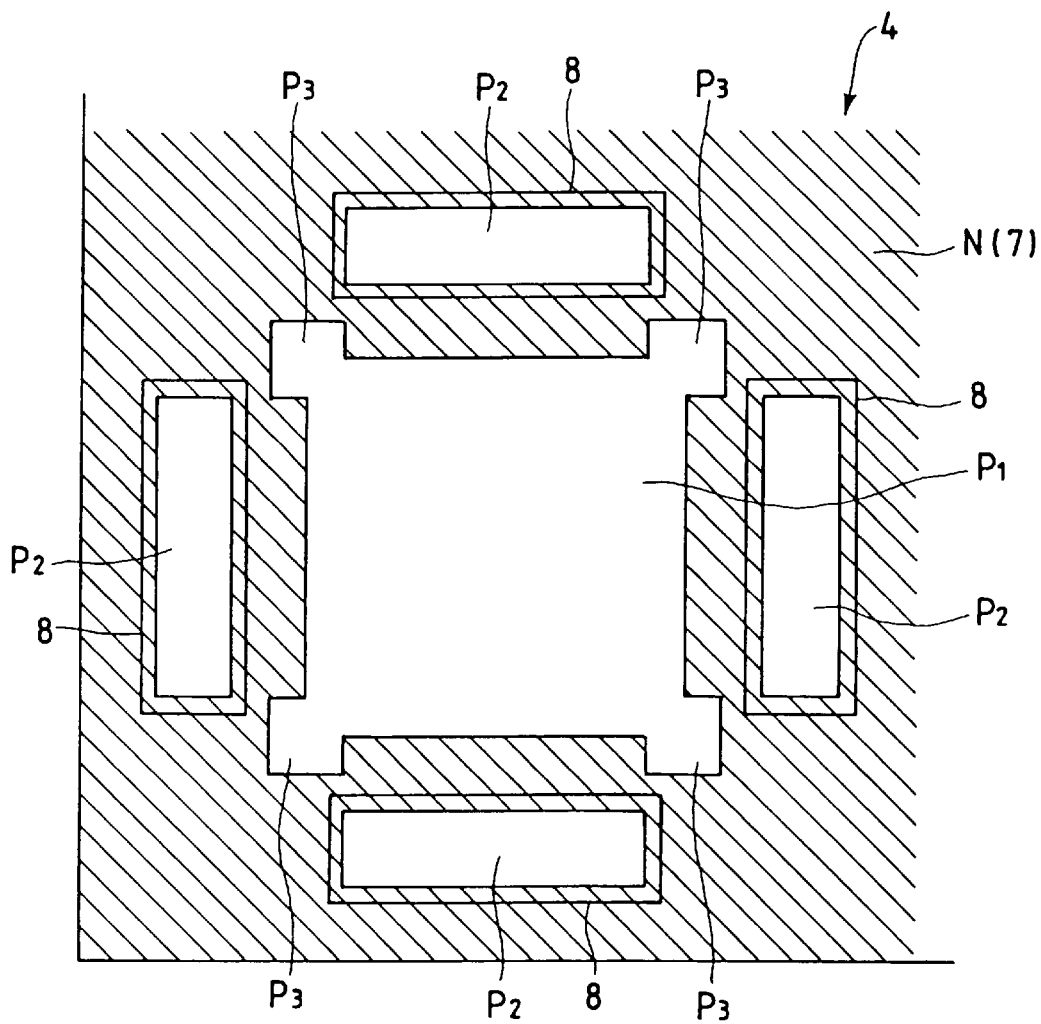
FIG. 22 is a plan view illustrating a beam distribution shifter provided in the laser beam machining apparatus.
Figure 23:
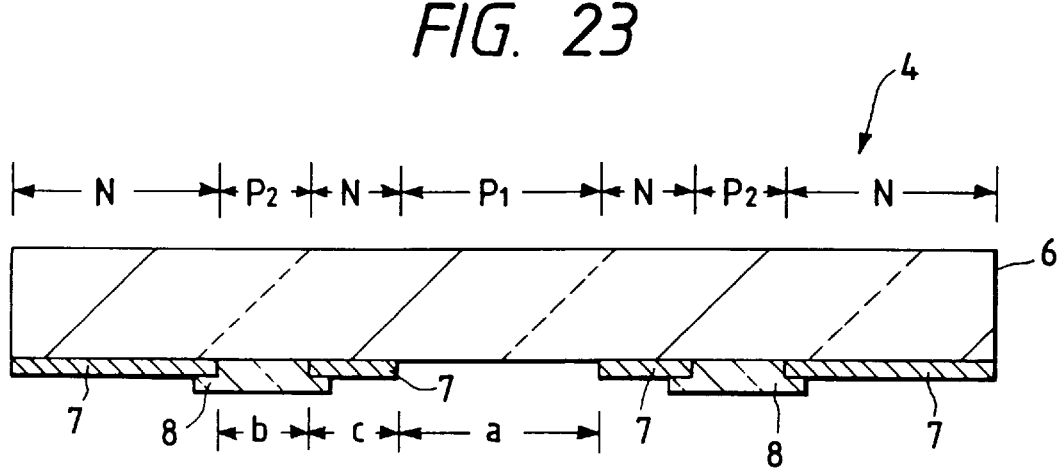
FIG. 23 is a sectional view showing the beam distribution shifter provided in the laser beam machining apparatus.

FIG. 22 is a plan view showing major portions of the beam distribution shifter 4 and FIG. 23 is a sectional view showing these major portions.

The beam distribution shifter 4 consists of a transparent glass substrate 6 on one side of which are provided light transmission regions $P_1$, $P_2$ and a light blocking region N. The light blocking region N is constituted by a light blocking film 7 such as of chromium deposited on one surface of the glass substrate 6.

The light transmission region $P_1$ is a large area disposed at the central portion of the glass substrate 6 and a plurality of light transmission regions $P_2$ are small areas arranged to surround the above region. A phase shifter 8 comprising a transparent thin film is formed on each of the light transmission regions $P_2$ having small areas.

In order to form a laser beam of a rectangular shape in this embodiment, the light transmission regions $P_1$, $P_2$ have rectangular patterns as shown in FIG. 22. The light flux $L_1$ having a large intensity that has passed through the light transmission region $P_1$ having the large area is permitted to fall on the central portion of the objective lens 5 and the light fluxes $L_2$ having a small intensity that have passed through light transmission regions $P_2$ having the small areas are permitted to fall on the peripheral portion of the objective lens 5.

The size (a) of the light transmission region $P_1$, the size (b) of the light transmission regions $P_2$ and the size (c) of the light blocking region N between them are selected to be, for example, a≈40 μm, b≦30 μm, and c≈20 μm. The magnification of the objective lens 5 is as great as about 100.

In addition to the fact that the light transmission region $P_1$ having the large area has a rectangular shape to form a beam of a rectangular shape, the beam distribution shifter 4 has additional small rectangular light transmission regions $P_3$ at corners of the rectangle in order to decrease the drop of light intensity at the corners of the rectangle.

Instead of the aforementioned method of providing the phase shifter 8 on the light transmission regions $P_2$ of the beam distribution shifter 4, it is also allowable to provide a groove in the light transmission regions $P_2$ in the glass substrate 6, so that the light fluxes $L_2$ passing through the grooves (light transmission regions $P_2$) and the light flux $L_1$ passing through the light transmission region $P_1$ will have opposite phases relative to each other, as in the same manner of the Embodiment 1.

The two light fluxes $L_1$, $L_2$ that have passed through the light transmission regions $P_1$, $P_2$ of the beam distribution shifter 4 have phases that are opposite relative to each other, the intensity of the light flux $L_1$ at the central portion being greater than the intensity of the light fluxes $L_2$ at the peripheral portions. Therefore, the laser beam falling on the sample 2 has a central portion that is prevented from spreading because of interference with the peripheral portion.

Therefore, by setting the size (b) of the light transmission regions $P_2$ of the beam distribution shifter 4 to be much smaller than the size (a) of the light transmission region $P_1$ to eliminate the effect of the beam periphery, the size of the laser beam falling on the surface of the sample 2 can be set to be substantially smaller than the limit value determined by the wavelength of the laser beam and characteristics of the objective lens 5.

The laser beam machining apparatus 60 of this embodiment can be adapted to, for example, remedying defects of a semiconductor memory.

Defect remedy of semiconductor memories is a technology wherein an auxiliary circuit (redundant circuit) is provided on an extra region of the semiconductor chip, and in case one of the regular circuits is defective, the defective circuit is replaced by the redundant circuit to remedy the defective chip.

The defective circuit and the redundant circuit are usually switched over by melt-cutting (opening the circuit) a programming element (called a link) constituted by polycrystalline silicon or the like using a pulse-like laser beam. As will be readily apparent to one of ordinary skill in the art, melt-cutting the programming element or link creates an open circuit. The open circuit replaces the defective circuit with the redundant circuit.

Figure 24:
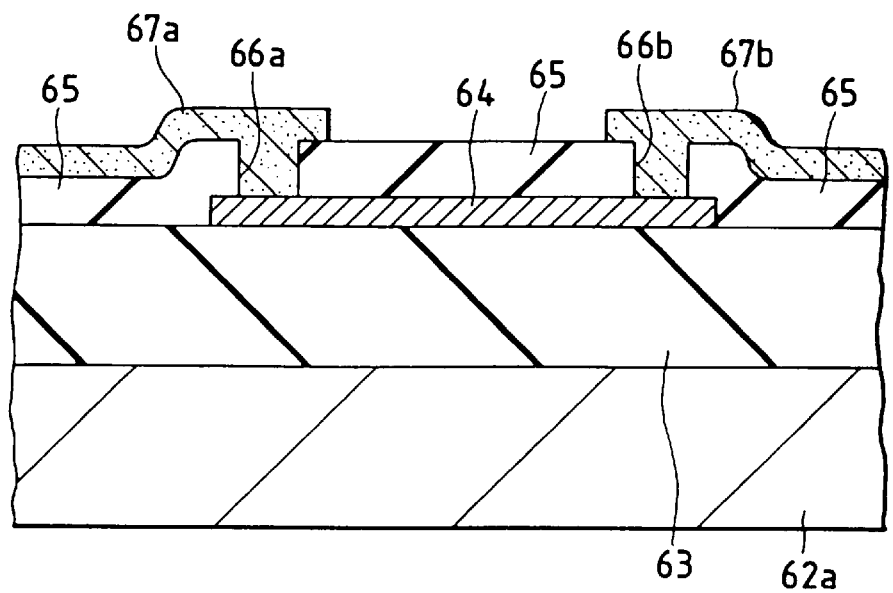
FIG. 24 is a sectional view illustrating major portions of a semiconductor chip to explain a defect remedy method for the semiconductor memory by using the laser beam machining apparatus.

FIG. 24 is a sectional view showing major portions of a semiconductor chip 62a.

An insulating film 63 made of silicon oxide for element isolation is formed on the main surface of the semiconductor chip 62a made of a single silicon crystal. On the insulating film 63 is formed a link 64 for switching over the defective circuit and the redundant circuit that are not shown.

The link 64 is connected to aluminum wiring 67a and 67b via through holes 66a and 66b formed in an interlayer insulating film 65 made of PSG (phosphosilicate glass) or a like material.

The material of the link 64 is polycrystalline silicon, or a polycide obtained by depositing polycrystalline silicon and a high-melting metal silicide ($WSi_x$, $MoSi_x$, etc.) in layers. Further, the link 64 is about 2 μm in width and about 10 μm in length.

The size of the link 64 is several times as great as a minimum pattern size (0.4 μm or smaller) of ultra-large scale integrated semiconductor circuit devices (64-megabit DRAM, etc.) that have been developed in recent years. This is due to the fact that with an existing laser beam machining apparatus, it is allowed to form patterns of a minimum of only about 2 μm.

With the laser beam machining apparatus 60 of this embodiment, on the other hand, it is possible to form a laser beam having a diameter smaller than a limit value that is determined by the wavelength of the laser beam and characteristics of the objective lens, enabling the size of the link 64 to be reduced to a fraction of the conventional size. It is further possible to reduce a variation in the distribution of beam intensities in the direction of the height of semiconductor chip 62a, and hence to reduce the limitation on the interlayer insulating film 65 deposited on the link 64.

Figure 25:
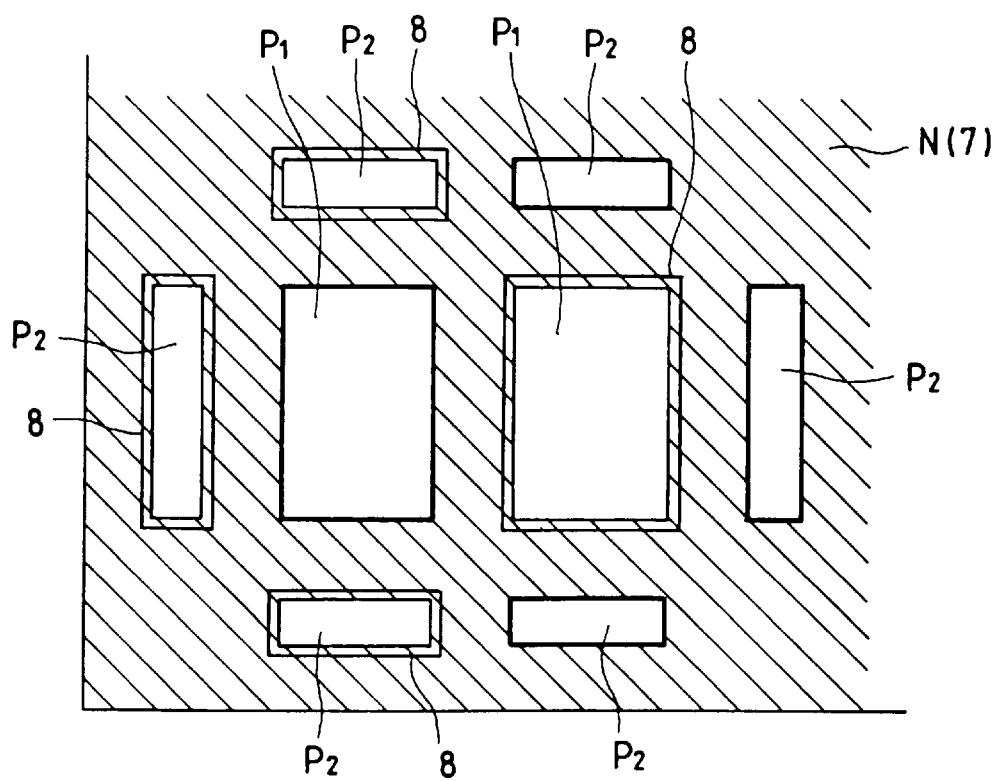
FIG. 25 is a plan view illustrating another structure of the beam distribution shifter.
Figure 26:
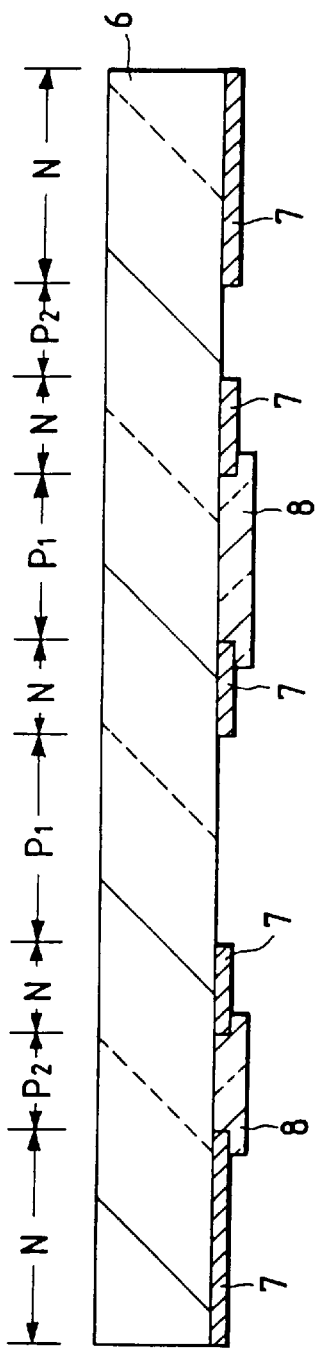
FIG. 26 is a sectional view showing the structure of the beam distribution shifter in FIG. 25.

Though the foregoing description has dealt with the case of forming a single laser beam, it is also possible to form a plurality of laser beams by using a beam distribution shifter 4 for forming multiple beams as shown in FIGS. 25 and 26.

As shown in FIGS. 25 and 26, the beam distribution shifter 4 for forming multiple beams has a pair of light transmission regions $P_1$, $P_1$ having large areas arranged at the central portion of the glass substrate 6 and a plurality of light transmission regions $P_2$ having small areas so arranged as to surround them.

The phase shifter 8 is formed on one of the pair of light transmission regions $P_1$ and $P_1$. The phase shifter 8 is further formed on the light transmission regions $P_2$ that surround the other light transmission region $P_1$ on which phase shifter 8 is not formed.

The light beams $L_1$ and $L_1$ having large intensities that have passed through the light transmission regions $P_1$, $P_1$ having large areas fall on the central portion of the objective lens 5, and the light beams $L_2$ of small intensities that have passed through the light transmission regions $P_2$ having small areas fall on the peripheral portion of the objective lens 5.

When the beam distribution shifter 4 is irradiated with the laser beam, the light flux $L_1$ that has passed through the light transmission region $P_1$ on which the phase shifter 8 is formed and the light fluxes $L_2$ that have passed through the light transmission regions $P_2$ on which the phase shifter 8 is not formed surrounding the above region $P_1$ have phases opposite to each other, and the light flux $L_1$ has an intensity that is stronger than the intensity of the light fluxes $L_2$.

Furthermore, the light flux $L_1$ that has passed through the other light transmission region $P_1$ on which the phase shifter 8 is not formed and the light fluxes $L_2$ that have passed through the light transmission regions $P_2$ on which the phase shifter 8 is formed surrounding the above region $P_1$ have phases opposite to each other, and the light flux $L_1$ has an intensity that is stronger than the intensity of the light fluxes $L_2$.

The two light fluxes $L_1$ and $L_1$ that have passed through the two light transmission regions $P_1$, $P_1$ have phases opposite to each other, and further have equal intensities.

Figure 27:
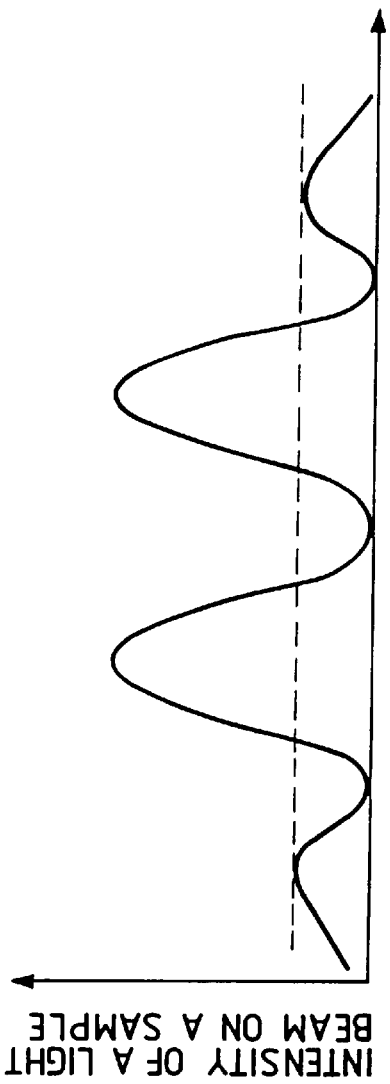
FIG. 27 is a diagram showing the intensity of a light beam on a sample.

If the areas of the light transmission regions $P_2$ of the beam distribution shifter 4 are set to be much smaller than the areas of the light transmission regions $P_1$ to eliminate the effect of the beam periphery, then two fine laser beams whose peripheries are suppressed from spreading and having an improved boundary contrast as shown in FIG. 27 are formed on the sample 2.

Moveover, the sizes and spacing of these two laser beams become substantially smaller than limit values determined by the wavelength of the laser beam and characteristics of the objective lens 5.

The beam distribution shifter 4 shown in FIGS. 25 and 26 are constituted so as to form two laser beams. However, it is further possible to form many laser beams having sizes and spacings substantially smaller than limit values determined by the wavelength of the laser beam and characteristics of the objective lens 5 by arranging many light transmission regions having large areas at the central portion of the glass substrate 6, arranging many light transmission regions having small areas to surround the above areas, and forming a phase shifter on predetermined ones of the light transmission regions.

By adapting multiple laser beams to remedying the defect of a semiconductor memory, it is possible to melt-cut a plurality of links simultaneously, contributing to increasing the throughput of the melt-cutting operation.

Moreover, since the size and spacing of the links can be decreased, the area of the redundant circuit can be reduced too.

Embodiment 5

Figure 28:
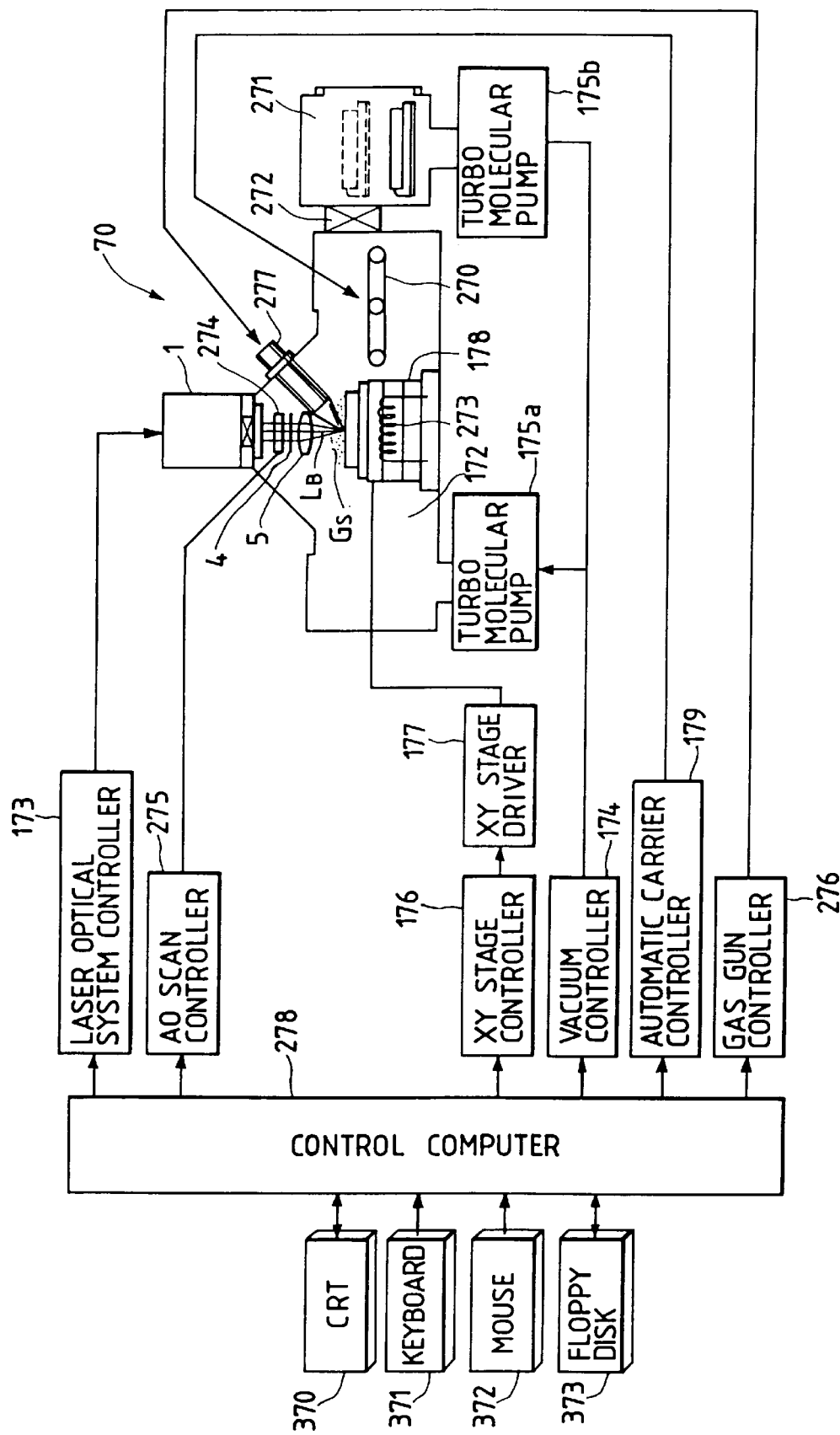
FIG. 28 is a diagram illustrating the entire structure of a laser CVD apparatus using the light beam-forming method of the present invention.

FIG. 28 illustrates a laser CVD apparatus 70 which utilizes the method of forming a light beam according to the present invention.

The laser CVD apparatus 70 comprises a processing system and a control system, the processing system having a processing chamber 172 equipped with a source 1 of a laser beam at the upper portion of FIG. 28. The source 1 of the laser beam has a laser output of, for example, 200 mW and continuously emits an argon laser beam of high output which is controlled by a laser optical system controller 173 provided outside the chamber 172.

The processing chamber 172 is evacuated to establish a predetermined vacuum condition (e.g., about 10 Pa) via a turbo molecular pump 175a which is controlled by a vacuum controller 174. At the center of the processing chamber 172 is installed an XY stage 178 that is driven in a horizontal direction by an XY stage controller 176 and an XY stage driver 177 outside the chamber 172.

A sample 2 such as a semiconductor wafer is carried onto the XY stage 178 through a shutter mechanism 272 from a preliminary chamber 271 on one side of the processing chamber 172 via an automatic carrier mechanism 270 that is controlled by an automatic carrier controller 179.

The preliminary chamber 271 is evacuated to establish a vacuum condition by means of a turbo molecular pump 175b controlled by the vacuum controller 174 independently of the processing chamber 172. Moreover, the XY stage 178 contains a heating means 273 such as a heater in order to heat the surface of the sample 2 to a desired temperature.

A beam deflecting/focusing optical system comprising a beam deflector 274, a beam distribution shifter 4 and an objective lens 5 is provided in the optical path of a laser beam $L_B$ that falls on the XY stage 178 from the source 1 of a laser beam at the upper portion of the processing chamber 172.

In this embodiment, for example, an AO modulator (acousto-optic modulator) is used as the beam deflector 274 which is controlled by an AO scan controller 275 outside the chamber 172.

The beam distribution shifter 4 is constituted in the same manner as that of the aforementioned Embodiment 1. That is, the laser beam $L_B$ emitted from the source 1 of a laser beam passes through the beam distribution shifter 4 where the beam is divided into two light fluxes $L_1$ and $L_2$ having opposite phases, one ($L_1$) of them falling on the central portion of the objective lens 5 and the other one ($L_2$) falling on the peripheral portion.

The beam distribution shifter 4 is disposed on the object image surface of the objective lens 5 and the sample 2 is disposed on the image-forming surface of the objective lens 5. Therefore, the projected image of the beam distribution shifter 4 is formed as a fine laser beam $L_B$ on the surface of the sample 2. The laser beam $L_B$ is permitted to fall on any position on the main surface of the sample 2 for a predetermined period of time by means of the beam deflecting/focusing optical system.

The laser beam $L_B$ falling on the surface of the sample 2 is such that initial light fluxes $L_1$ and $L_2$ have phases opposite to each other, the light flux $L_1$ falling on the central portion of the objective lens 5 having an intensity greater than that of the light flux $L_2$ falling on the peripheral portion. Therefore, the laser beam $L_B$ has a central portion which is prevented from spreading because of the interference with the periphery.

Even in this case, the effect of the beam periphery is eliminated, so that the diameter of the laser beam $L_B$ falling on the surface of the sample 2 becomes substantially smaller than a limit value that is determined by the wavelength of the laser beam and characteristics of the objective lens 5.

A gas gun (reaction gas feeding means) 277 controlled by a gas gun controller 276 is disposed at an upper side position of the XY stage 178 on which the sample 2 is placed. The gas gun 277 feeds a reaction gas Gs containing a metal compound such as molybdenum carbonyl ($Mo(CO)_6$) onto the surface of the sample 2 on the XY stage 178.

The above gas gun controller 276 is controlled by a control computer 278 having a large-capacity storage unit and a CPU. The control computer 278 stores information on the position of the sample 2 irradiated with the laser beam $L_B$ and graphic information related to the spot diameter of laser beam $L_B$, which are suitably selected by a control program and are transferred to the above-mentioned controllers as required.

The position coordinate of the sample 2 is detected by scanning a positioning mark on the surface of the sample 2 using the laser beam $L_B$ measuring the position of the XY stage 178 using a laser. Moreover, the height of the sample 2 is detected by irradiating the surface of the sample 2 with light from an oblique direction and by detecting the reflected light thereof.

The above laser CVD apparatus 70 can be adapted to connecting, for example, semiconductor chips together and connecting wiring in a semiconductor chip.

Figure 29:
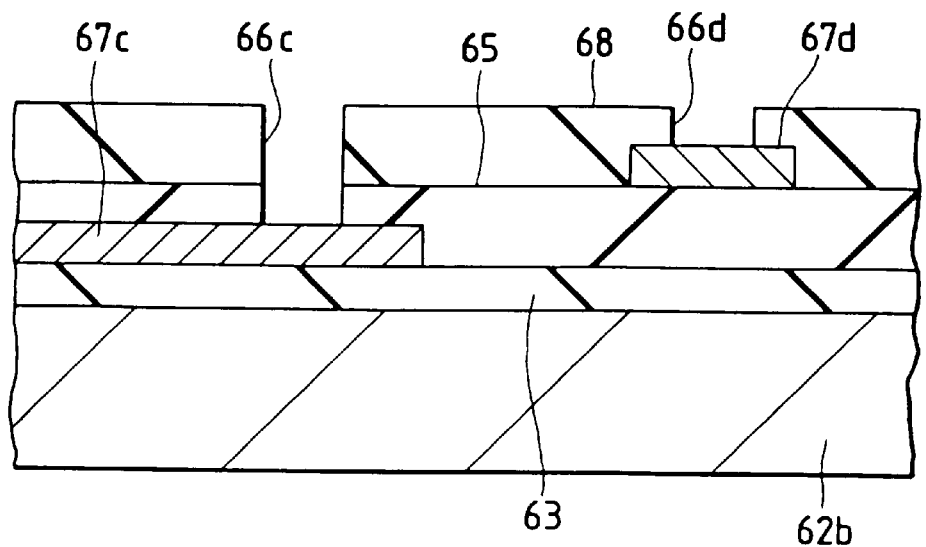
FIG. 29 is a sectional view of major portions illustrating a method of wiring of a semiconductor chip using the laser CVD apparatus.

FIG. 29 is a sectional view showing major portions of the semiconductor chip 62b.

An insulating film 63 of silicon oxide is formed on the main surface of the semiconductor chip 62b made up of a single silicon crystal, and an aluminum wiring 67c of a first layer is formed on the insulating film 63. Further, an aluminum wiring 67d of a second layer is formed on an interlayer insulating film 65 of PSG or the like.

A passivation film 68 of silicon nitride or the like is formed on the surface of the semiconductor chip 62b. In the passivation film 68 are formed a through hole 66c that reaches the aluminum wiring 67c of the first layer and a through hole 66d that reaches the aluminum wiring 67d of the second layer.

To form the through holes 66c and 66d, predetermined regions of an electron beam resist applied onto the passivation film 68 are exposed to an electron beam, the electron beam resist is developed to form a resist mask, and the passivation film 68 and interlayer insulating film 65 are etched using the resist mask.

To electrically connect the aluminum wiring 67c and 67d of the semiconductor chip 62b together, the semiconductor wafer is first carried into the processing chamber 172 of the laser CVD apparatus 70 shown in FIG. 28 and is placed on the XY stage 178.

The position of the semiconductor wafer is determined by scanning a positioning mark formed on the semiconductor chip 62b using the laser beam $L_B$, and measuring the position of the XY stage 178 using a laser. Further, the height of the semiconductor wafer is detected by irradiating the surface of wafer with light from an oblique direction and detecting the reflected light thereof.

After the position is determined, the turbo molecular pump 175a is operated under control of the vacuum controller 174, the inside of the processing chamber 172 is evacuated to about 10 Pa, and then the gas gun 277 is operated so that the surface of the semiconductor wafer (semiconductor chip 62b) if covered with an atmosphere of a reaction gas Gs containing $MO(CO)_6$.

Next, the source 1 of the laser beam is turned on by a signal from the laser optical system controller 173, and the surface of aluminum wiring 67c of the first layer exposed at the bottom of the through hole 66c of semiconductor chip 62b is irradiated with the laser beam $L_B$.

Figure 30:
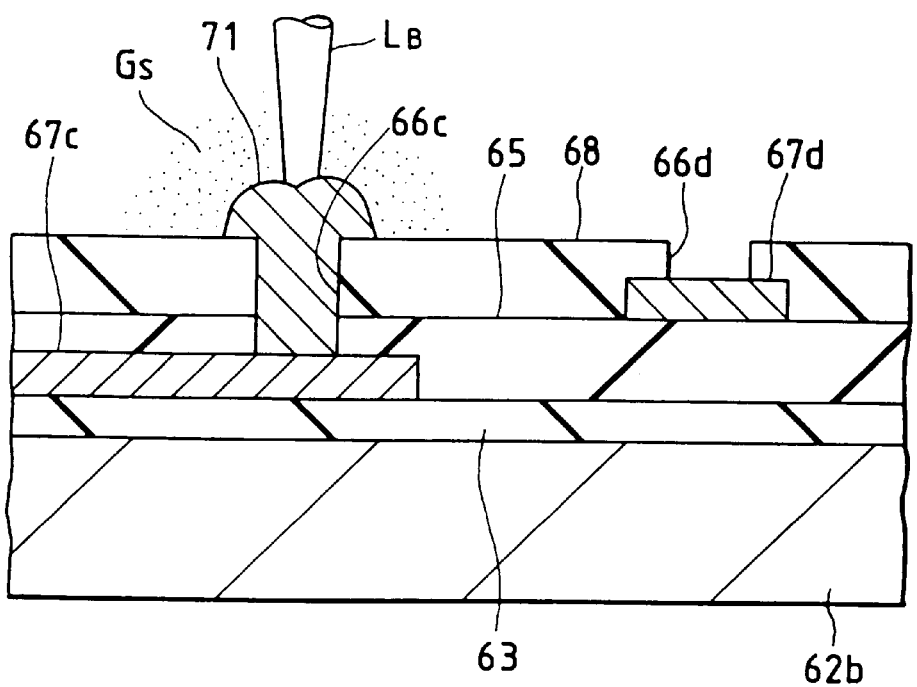
FIG. 30 is a sectional view of major portions illustrating the method of wiring of the semiconductor chip using the laser CVD apparatus.

Then, $Mo(CO)_6$ is decomposed by the energy of the laser beam $L_B$ and molybdenum precipitates on the surface of the aluminum wiring 67c as shown in FIG. 30. The molybdenum layer 71 gradually grows as the irradiation with laser beam $L_B$ is continued, and reaches the top of the through hole 66c.

Figure 31:
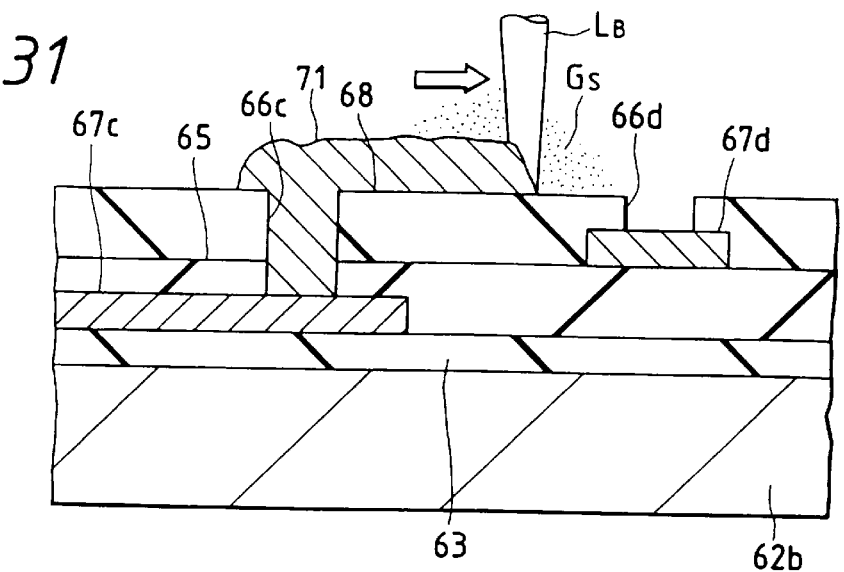
FIG. 31 is a sectional view of major portions illustrating the method of wiring of the semiconductor chip using the laser CVD apparatus.

Then, the XY stage 178 is moved in a horizontal direction and the laser beam $L_B$ moves toward the through hole 66d, so that the Mo layer 71 is precipitated on the surface of the passivation film 68 along the trace of the laser beam $L_B$ as shown in FIG. 31.

The XY stage 178 is moved while the positioning mark of the semiconductor chip 62b is being measured in reference to a connection data file stored in the control computer 278.

Figure 32:
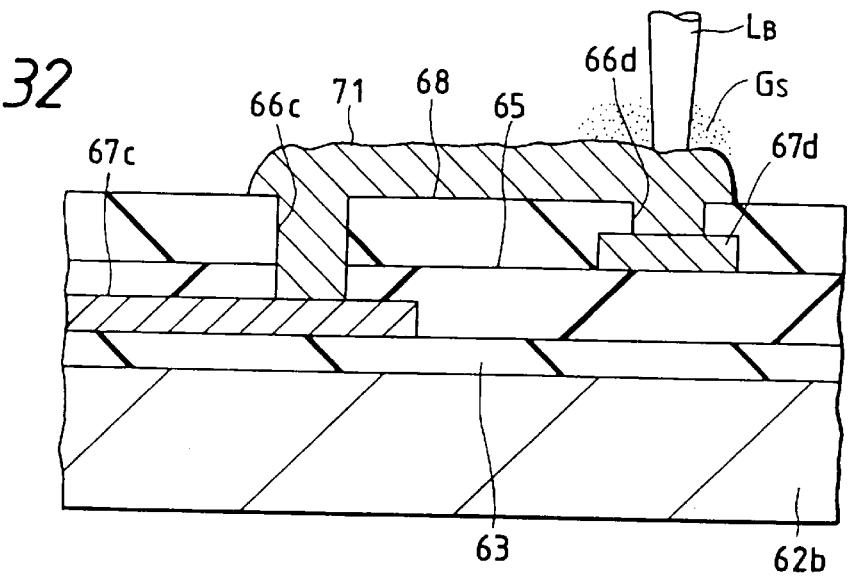
FIG. 32 is a sectional view of major portions illustrating the method of wiring of the semiconductor chip using the laser CVD apparatus.

Then, the laser beam $L_B$ moves to the through hole 66d, and the surface of the aluminum wiring 67d of the second layer exposed at the bottom thereof is irradiated with the laser beam $L_B$. Molybdenum then precipitates on the surface of aluminum wiring 67d, and the aluminum wiring 67c and 67d are electrically connected together via a wiring comprising molybdenum layer 71 as shown in FIG. 32.

After the aluminum wiring 67c and 67d are electrically connected together, the XY stage 178 is heated at about 300° C. to anneal the molybdenum layer 71 which constitutes the wiring for connection in order to decrease its resistance. Finally, the surface of the semiconductor chip 62b is coated with a passivation film that is not shown, and then the step of connecting the wiring is completed.

By using the laser CVD apparatus 70 of this embodiment, the laser beam can reach deeply into the through holes 66c and 66d, making it possible to connect the semiconductor elements using fine wiring.

Though the foregoing description relates to the case of connecting wiring within the semiconductor chip, the laser CVD apparatus 70 of this embodiment can be adapted to interconnection of wiring between the semiconductor chips and wiring between semiconductor wafers.

Embodiment 6

Figure 33:
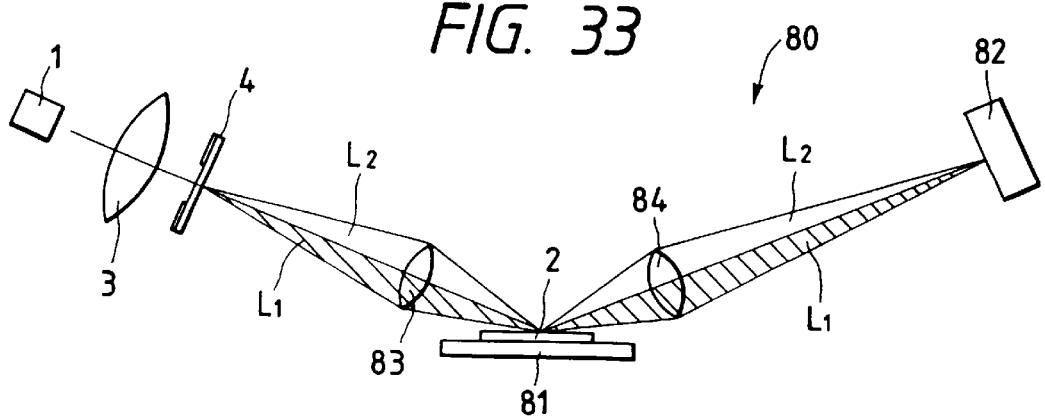
FIG. 33 is a diagram illustrating the structure of an optical system of a height-measuring apparatus using the light beam-forming method of the present invention.

FIG. 33 shows an optical system of a height-measuring apparatus 80 utilizing the method of forming a light beam of the present invention.

The sample 2 is placed on a sample plate 81 which is an XY table that is movable in a horizontal plane. The sample 2 is a semiconductor wafer made of, for example, a single silicon crystal.

The source 1 of light is disposed at an upper side position of the sample plate 81, and the surface of the sample 2 is irradiated with the light beam maintaining a predetermined oblique angle. The source 1 of light is, for example, a helium-neon laser.

An optical position sensor 82 comprising, for example, a CCD (charge coupled device) is disposed at a position corresponding to the source 1 of light with the sample 2 interposed therebetween in order to detect the position of the light path of the laser beam reflected by the surface of the sample 2.

The condenser lens 3, beam distribution shifter 4 and projection lens 83 are disposed on the optical path of the laser beam incident on the sample 2 from the source 1 of light. The beam distribution shifter 4 is disposed on the object image plane of the projection lens 83 and the sample 2 is disposed on the image-forming plane of the projection lens 83.

A light-receiving lens 84 is disposed on the optical path of the laser beam reflected from the sample 2 to the optical position sensor 82. The condenser lens 3, beam distribution shifter 4, projection lens 83 and light-receiving lens 84 are arranged such that the incident light path and the reflected light path of the laser beam are in the same plane.

Figure 34:
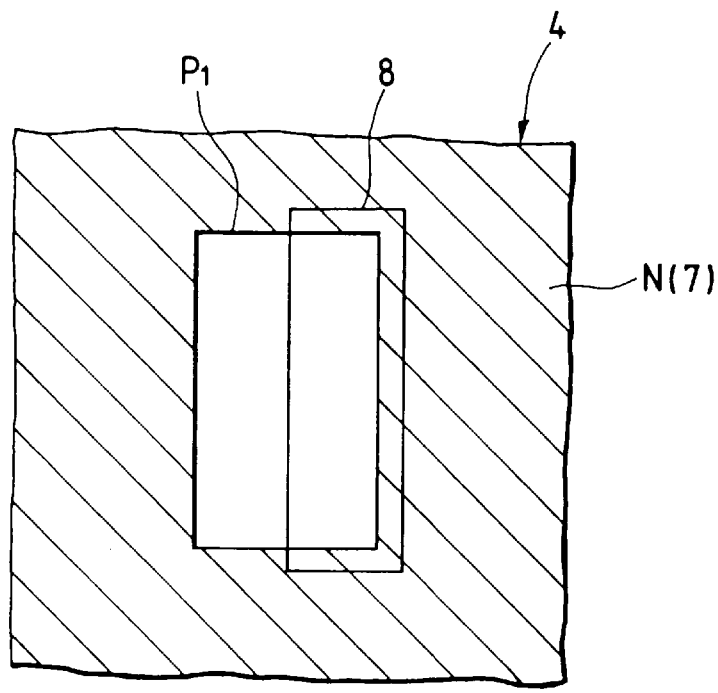
FIG. 34 is a plan view showing the structure of a beam distribution shifter provided in the height-measuring apparatus.
Figure 35:
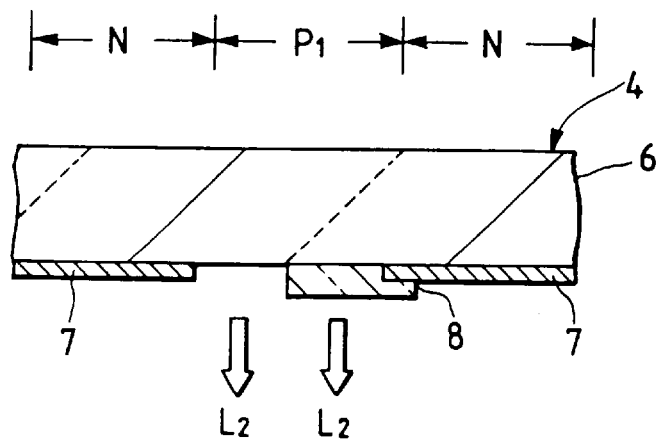
FIG. 35 is a sectional view showing the structure of the beam distribution shifter provided in the height-measuring apparatus.

FIG. 34 is a plan view showing major portions of the beam distribution shifter 4 and FIG. 35 is a sectional view which shows these major portions.

The beam distribution shifter 4 has a rectangular light transmission region $P_1$ surrounded by a light interruption region N on one surface of a transparent glass substrate 6. The light interruption region N is constituted by a light interruption film 7 such as chromium.

The phase shifter 8 comprising a thin transparent film such as spin-on-glass is formed on a portion of the light transmission region $P_1$. The phase shifter 8 is disposed so as to occupy nearly half of the whole area of the light transmission region $P_1$.

With the phase shifter 8 being thus provided, the laser beam that has passed through the light transmission region $P_1$ of the beam distribution shifter 4 is divided into two light fluxes $L_1$ and $L_2$ having phases opposite to each other. Moreover, the light flux $L_1$ that has passed through the region without the phase shifter 8 has an intensity that is nearly equal to the intensity of the light flux $L_2$ that has passed through the region with the phase shifter 8.

To render the phases of the two light fluxes $L_1$ and $L_2$ to be opposite to each other, the thickness (d) of the thin film material constituting the phase shifter 8 is set to substantially satisfy the relationship:

$$d=\lambda/2(n-1)$$

where n denotes the refractive index of the thin film material, and k denotes the wavelength of the laser beam.

When n=1.5 and $\lambda$=633 nm (He—Ne laser), for instance, d is set to be about 633 nm.

Figure 36:
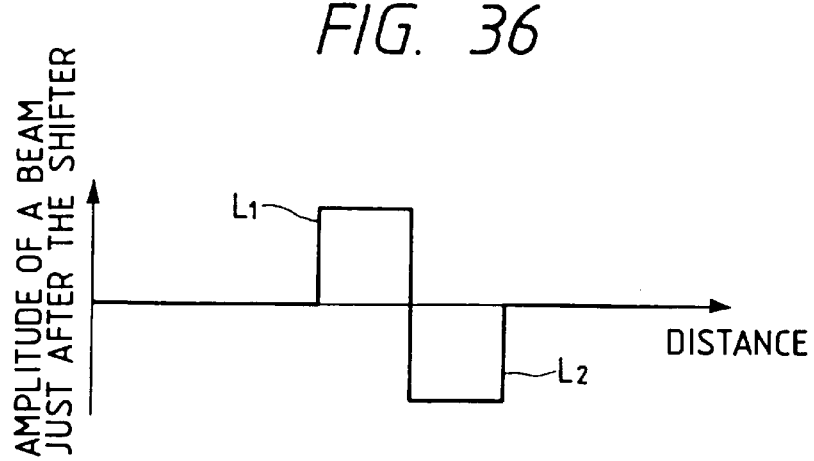
FIG. 36 is a diagram showing the amplitude of a light beam just after having passed through the beam distribution shifter.
Figure 37:
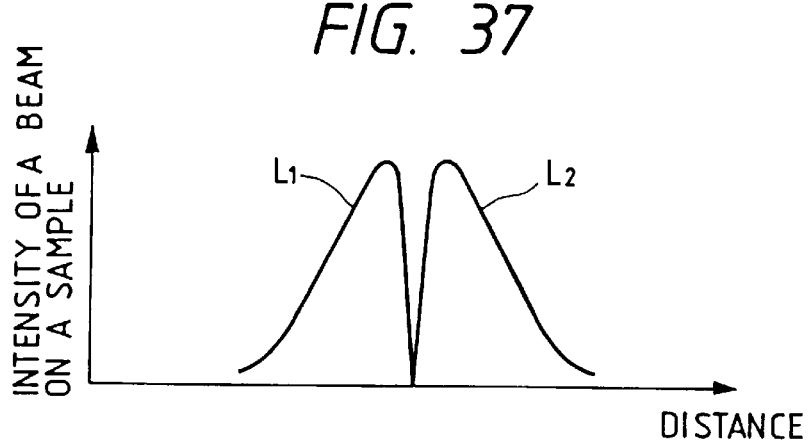
FIG. 37 is a diagram showing the intensity of a light beam on a sample.

As shown in FIG. 36, the two light fluxes $L_1$ and $L_2$ have phases opposite to each other and have edges which are in contact with each other at the boundary therebetween. Therefore, if the two fluxes $L_1$ and $L_2$ are focused via the projection lens 83 so as to fall on the sample 2, the two light fluxes $L_1$ and $L_2$ interfere with each other and are weakened at the boundary as shown in FIG. 37. Therefore, the contrast exhibited at the boundary is improved, and two very close and fine laser beams are obtained.

That is, by irradiating the sample 2 with two light beams $L_1$ and $L_2$ that have phases opposite to each other and have edges which are in contact with each other at the boundary therebetween, it is possible to form laser beams having diameters smaller than an optical limit value determined by the wavelength of the laser beam and the numerical aperture of the projection lens 83.

Figure 38:
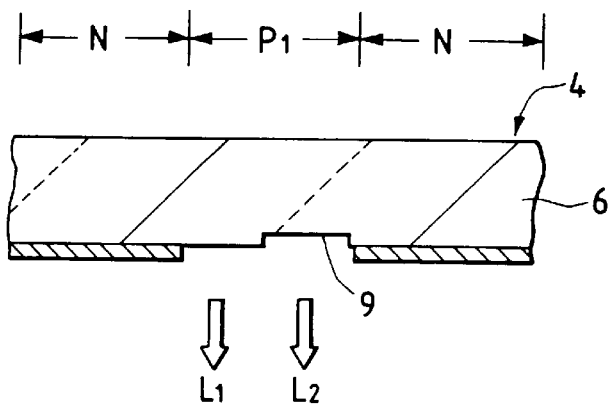
FIG. 38 is a sectional view showing another structure of the beam distribution shifter.

It is also possible in the same manner as in the aforementioned Embodiment 1 to form a groove 9 in the light transmission region $P_1$ of the glass substrate 6 as shown in FIG. 38 instead of the above-mentioned means which provides the phase shifter 8 on the light transmission region $P_1$ in order that the light flux $L_2$ passing through the groove 9 and the light flux $L_1$ passing through the remaining light transmission region $P_1$ will have phases opposite to each other.

The two light fluxes $L_1$ and $L_2$ incident on the surface of the sample 2 at a predetermined oblique angle are reflected while maintaining their mutual positional relationship, pass through light paths reflecting the heights of reflecting portions of the sample 2, and are incident on the optical position sensor 82 via the light-receiving lens 84.

Therefore, the optical position sensor 82 detects peak intensity positions of the light fluxes $L_1$, $L_2$ shown in FIG. 37 in the up-and-down direction and further detects a region having a very low intensity at an intermediate position between the above positions.

By detecting average values of the positions of the peak intensities of the light fluxes $L_1$ and $L_2$ or by detecting the position of a region having a very low intensity that exists between the above positions, it is possible to measure the height of the reflecting portions of the sample 2 with a precision higher than when the reflected light of a single laser beam is detected.

Figure 39:
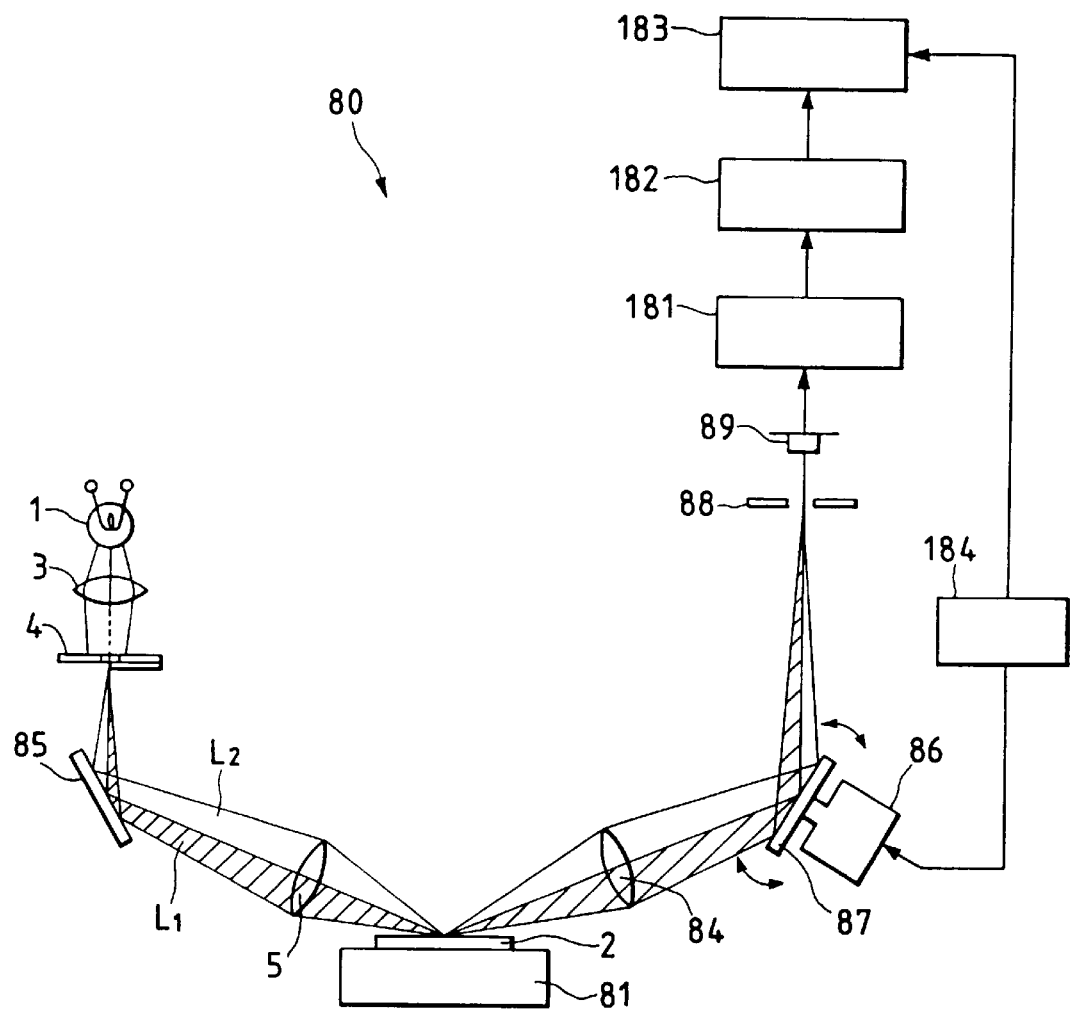
FIG. 39 is a diagram illustrating the structure of the optical system in the height-measuring apparatus of another embodiment of the present invention.

FIG. 39 illustrates another optical system of the height-measuring apparatus 80 of this embodiment.

A condenser lens 3, beam distribution shifter 4, mirror 85 and objective lens 5 are arranged on an optical path of a laser beam incident on a sample 2 from a source 1 of light.

The beam distribution shifter 4 is disposed on the object image plane of the objective lens 5 and the sample 2 is disposed on the image-forming plane of the objective lens 5. The beam distribution shifter 4 is constituted in the same manner as the one shown in FIGS. 34 and 35.

The laser beam emitted from the source 1 of light passes through the beam distribution shifter 4 where it is divided into two light fluxes $L_1$ and $L_2$ that have phases opposite to each other and have edges which are in contact with each other. The two light fluxes $L_1$ and $L_2$ are reflected by the mirror 85 and are focused by the objective lens 5 so as to be incident on the surface of the sample 2 from an oblique direction.

The light fluxes $L_1$ and $L_2$ reflected by the surface of the sample 2 are incident on a photodetector 89 via a light-receiving lens 84, an oscillating mirror 87 driven by a drive mechanism 86, and an aperture 88.

The photodetector 89 is connected to a detecting circuit 183 via an amplifier 181 and an A/D converter 182. The detecting circuit 183 receives as reference signals an oscillation frequency of the oscillating mirror 87 from an oscillator 184 that oscillates the oscillating mirror 87, and effects a known synchronous detection operation for the position detection signals of light fluxes $L_1$, $L_2$ obtained from the photodetector 89 whose detection level changes periodically due to the oscillation of the oscillating mirror 87.

Using the height-measuring apparatus 80 equipped with the above-mentioned optical system, it is possible to measure the height of the sample with a precision higher than a theoretical limitation determined by the wavelength and the like when a single laser beam is used owing to synergistic effects of the improved precision in detecting the reflecting positions when two light fluxes $L_1$ and $L_2$ are projected and the improved precision in detecting the reflecting positions by the synchronous detection using oscillating mirror 87.

Figure 40:
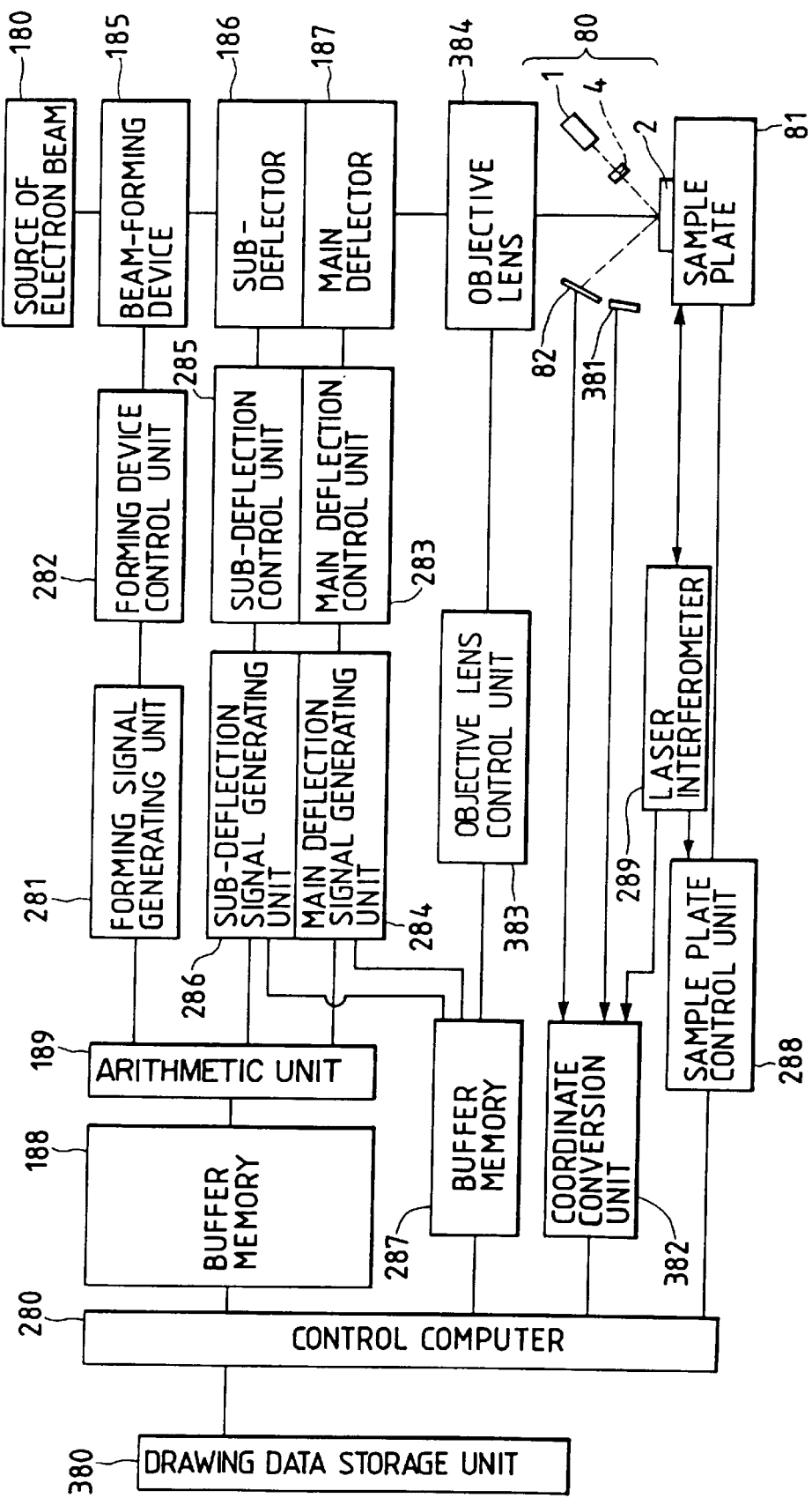
FIG. 40 is a diagram illustrating the whole structure of the height-measuring apparatus.

FIG. 40 illustrates the whole constitution of the height-measuring apparatus 80.

The height-measuring apparatus 80 constitutes a portion of an electron beam drawing apparatus used in, for example, a step of manufacturing semiconductor integrated circuit devices.

A lens barrel that is not shown is provided just over the sample plate 81 on which the sample 2 is placed, and a source 180 of an electron beam is disposed on the top of the lens barrel. A beam forming device 185, a sub-deflector 186, a main deflector 187 and an objective lens 384 are arranged on an optical path that links the source 180 of an electron beam to the sample 2. The sample 2 is a semiconductor wafer which is spin-coated on the surface thereof with electron beam resist.

A control computer 280 that controls the whole apparatus is provided with a drawing data storage unit 380 of a large memory capacity to store drawing data such as integrated circuit patterns to be formed onto the semiconductor wafer. The drawing data necessary for the actual drawing operation is transferred to buffer memory 188 and is processed by an arithmetic unit 189.

The arithmetic unit 189 controls beam-forming device 185 via a forming signal generating unit 281 and forming device control unit 282 in order to control the shape of a photoelectron plane of the electron beam to have a desired shape. The main deflector 187 is controlled by the arithmetic unit 189 via a main deflection control unit 283 and a main deflection signal generating unit 284, and determines the axis of the electron beam irradiation region of the semiconductor wafer.

The sub-deflector 186 is controlled by the arithmetic unit 189 via a sub-deflection control unit 285 and a sub-deflection signal generating unit 286, and controls the position of electron beam irradiation along the axis determined by the main deflector 187. That is, the position of electron beam irradiation for the semiconductor wafer is controlled by adding the amounts of deflection of the main deflector 187 and the sub-deflector 186.

The sub-deflection signal generating unit 286 and the main deflection signal generating unit 284 are connected to the control computer 280 via a buffer memory 287, and effect various corrections for the geometrical pattern data according to the drawing data processed by the arithmetic unit 189 in order to control the sub-deflector 186 and the main deflector 187.

A sample plate 81 on which a semiconductor wafer is placed is controlled by the control computer 280 via a sample plate control unit 288 which operates to move the sample plate 81 to a position specified by the control computer on the basis of measured values from a laser interferometer 289 that precisely measures the amount of displacement of the sample plate 81.

An electron detector 381 is disposed near the side of the sample plate 81 to detect secondary electrons produced when a positioning mark on the semiconductor wafer is irradiated with an electron beam in synchronism with the scanning with the electron beam and to specify the position of the above mark.

The position data of the positioning mark is converted by a coordinate conversion unit 382 into values in a predetermined reference coordinate system and is input to the control computer 280 to control the whole operation, and is further input to the buffer memory 287 to control the correction of the main deflector 187 and the sub-deflector 186.

The height-measuring apparatus 80 of this embodiment is disposed near the sample plate 81, and the source 1 of light is disposed at a position to project a He—Ne laser beam to the surface of the sample 2 at a predetermined oblique angle.

The laser beam emitted from the source 1 of light passes through the beam distribution shifter 4 where it is divided into two light fluxes $L_1$ and $L_2$ having phases opposite to each other and edges which are in contact with each other, and then falls on a desired portion of the sample 2.

In this case, the light fluxes $L_1$, $L_2$ reflected from the surface of the sample 2 are detected by an optical position sensor 82 so that the height of the sample 2 at the irradiated portion can be precisely measured. For the purpose of convenience of illustration, the projection lens 83 and the light-receiving lens 84 shown in FIG. 33 are not shown here.

The thus detected height data of the portion of the semiconductor wafer irradiated with the electron beam is converted via the coordinate conversion unit 382 into data in a predetermined reference coordinate system, and is stored in the buffer memory 287. By making reference to the height data, the control computer 280 and an objective lens control unit 383 operate so that the electron beam passing through the objective lens 384 may be focused on the semiconductor wafer.

Next, described below is a method of drawing a pattern by using the above-mentioned electron beam drawing apparatus. First, drawing data of a predetermined pattern is transferred to the buffer memory 188. Then, as the drawing position on the semiconductor wafer is determined on the optical axis of the electron optical system, the positioning mark on the semiconductor wafer is scanned with the electron beam and the laser beam, and the coordinate data and height data at the drawing position of the semiconductor wafer are stored in the buffer memory 287 via the coordinate conversion unit 382.

In this case, since the electron beam drawing apparatus of this embodiment uses the light fluxes $L_1$ and $L_2$ as the laser beam, the peak intensity positions to be detected are less blurred compared with the case where a single laser beam is used, and the height data can be detected with a high precision.

Then, the drawing position is determined for the electron optical system on the basis of the aforementioned coordinate data, and the focal position of the objective lens 384 is set with respect to the semiconductor wafer on the basis of the height data of the drawing position.

Thereafter, the arithmetic unit 189 calculates control signals related to the shape of the electron beam and the amount of deflection on the basis of the drawing data stored in the buffer memory 188, and controls the beam-forming device 185 via the forming device control unit 282, controls the main deflector 187 and the sub-deflector 186 via the main deflection control unit 283 and sub-deflection control unit 285, and controls the objective lens 384 via the objective lens control unit 383.

In carrying out these control operations, the correction data and like data stored in advance in the buffer memory 287 are selectively read out as required according to the pattern position and height of the surface of the semiconductor wafer and are supplied to the main deflection control unit 283, sub-deflection control unit 285 and objective lens control unit 383.

In the electron beam drawing apparatus as described above, the semiconductor wafer is irradiated with light fluxes $L_1$, $L_2$ from the height-measuring apparatus 80, and the height is measured by measuring the light path of the reflected light with a precision higher than that when a single laser beam is used.

From the measurement result, the focusing operation of the objective lens 384 is controlled and the detected position of the positioning mark on the semiconductor wafer is corrected, enabling the pattern to be drawn with a higher precision.

Figure 41:
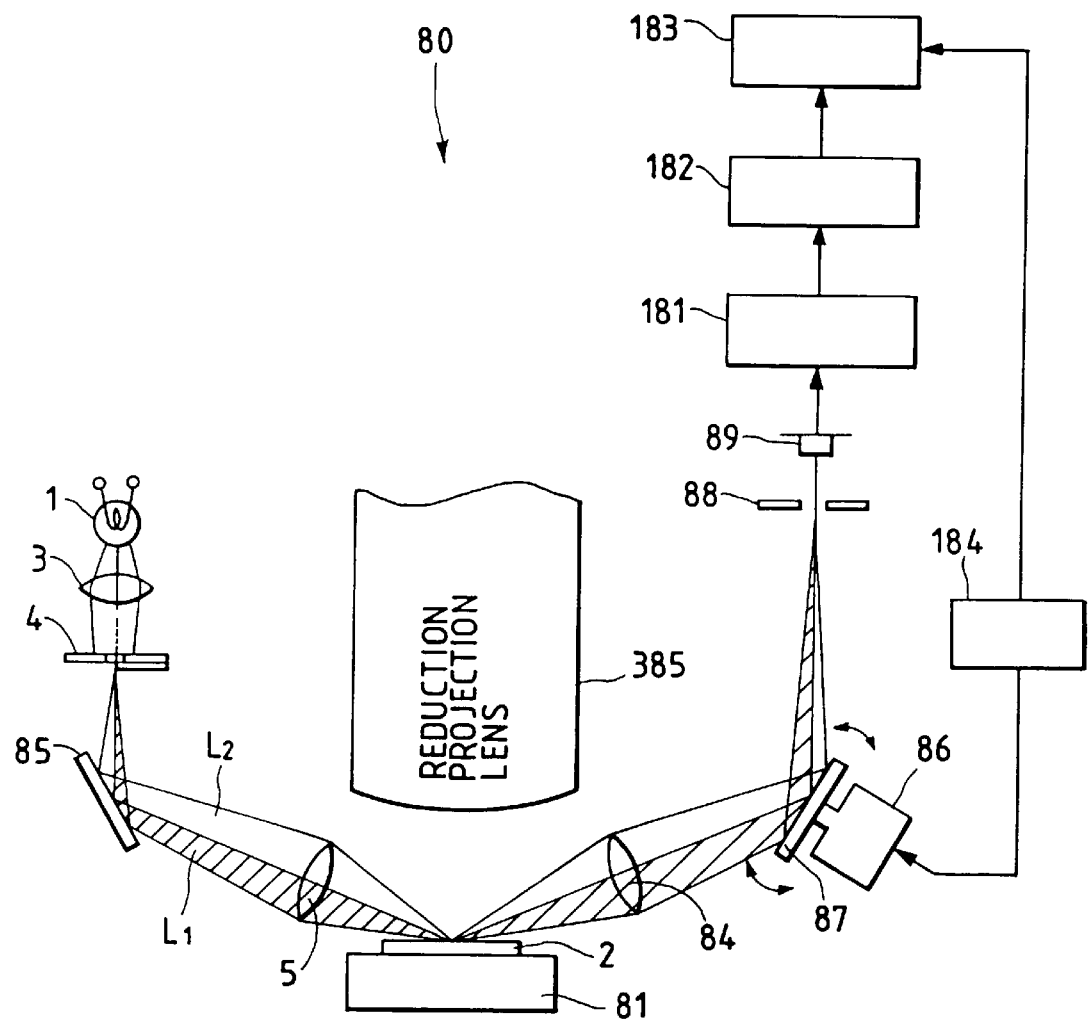
FIG. 41 is a diagram illustrating the structure of the optical system in the height-measuring apparatus of a further embodiment of the present invention.

FIG. 41 shows another optical system of the height-measuring apparatus 80 of this embodiment.

The height-measuring apparatus 80 equipped with this optical system constitutes a portion of the light exposure apparatus employed in the process of manufacturing, for example, semiconductor integrated circuit devices.

Over the sample plate 81 is disposed a reduction projection lens 385 that permits the sample (semiconductor wafer) 2 placed on the sample plate 81 to be irradiated with light that has transmitted through the mother plate such as a reticle that is not shown.

The height measurement for focusing the reduction projection lens 385 on the semiconductor wafer is made by irradiating the semiconductor wafer with light fluxes $L_1$, $L_2$ from the measuring apparatus 80.

Using the above-mentioned light exposure apparatus, the semiconductor wafer is irradiated with the light fluxes $L_1$ and $L_2$ formed by the height-measuring apparatus 80 to measure the height by measuring the light path of the reflected light with a precision higher than that when a single laser beam is used.

This makes it possible to carry out the focusing operation of the reduction projection lens 385 with respect to the semiconductor wafer with a high precision, and hence to improve dimensional precision of the integrated circuit pattern that is transferred onto the semiconductor wafer.

In the foregoing description, the height-measuring apparatus 80 of the embodiment is adapted to the electron beam drawing apparatus and the light exposure apparatus. The invention, however, is in no way limited thereto only. For instance, the height-measuring apparatus 80 of this embodiment can be employed in machining and inspecting the surface of a sample where the precision of detecting the height of the sample surface tends to be deteriorated due to steps and unevenness in the surface of the sample in order to improve the precision of detecting the height.

Embodiment 7

Figure 42:
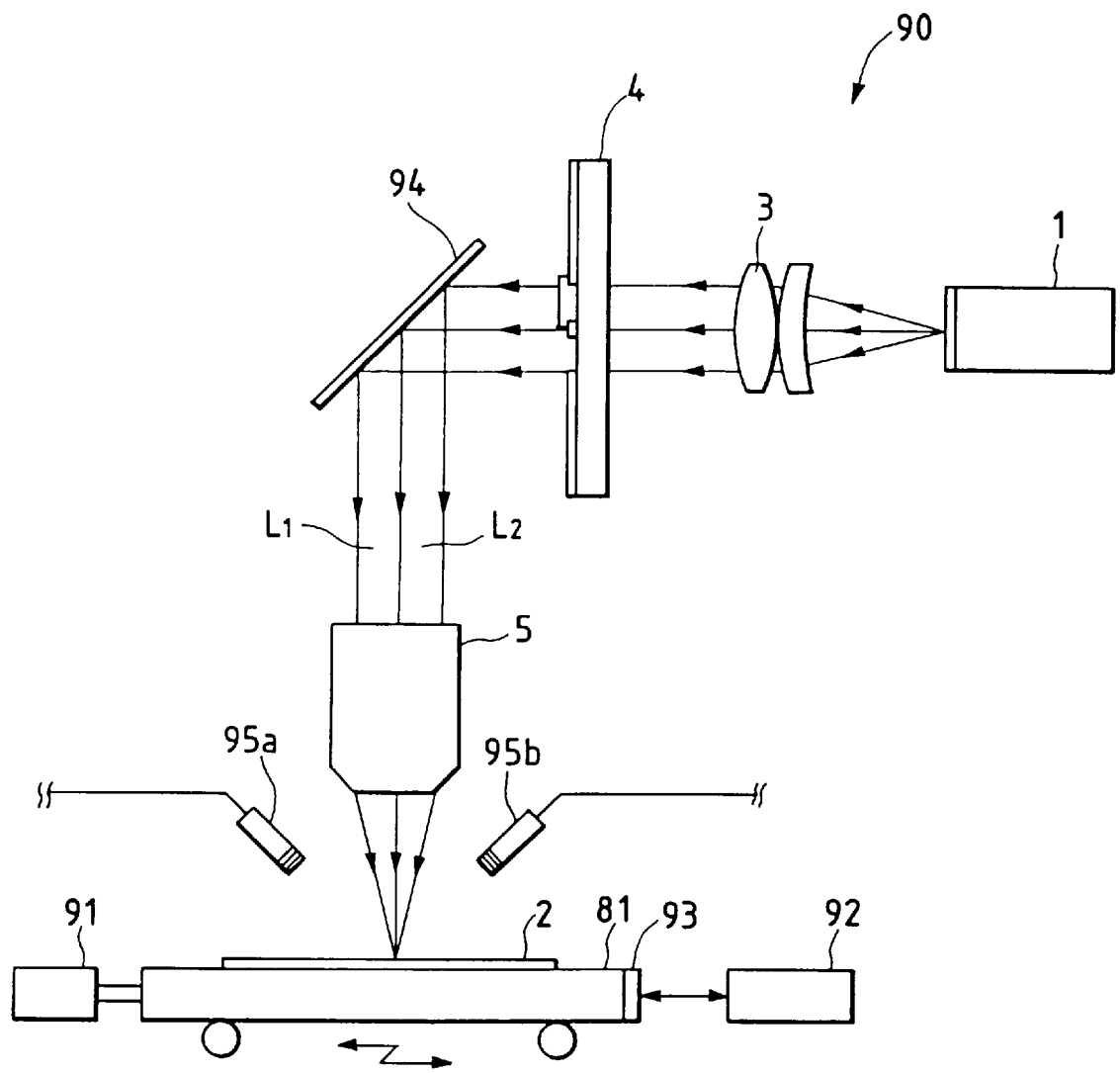
FIG. 42 is a diagram illustrating the structure of an optical system in a size-measuring apparatus using the light beam-forming method of the present invention.

FIG. 42 shows an optical system of a size-measuring apparatus 90 utilizing the method of forming a light beam of the present invention.

The sample 2 is placed on the sample plate 81 which consists of an XY table movable in a horizontal plane. The sample plate 81 is allowed to move a desired distance in the horizontal direction by being actuated by a drive unit 91 such as a pulse motor connected to an end thereof. The sample 2 here is a photomask for transferring an integrated circuit pattern onto a semiconductor wafer.

A laser interferometer 92 is provided near the sample plate 81, and a laser beam of a predetermined wavelength is projected therefrom onto a laser interference mirror 93 attached to the end of the sample plate 81, and darkness and brightness of interference waves produced between the reflected light and the light reflected by a fixed mirror in the laser interferometer 92 are measured in order to highly precisely measure the moving amount of the sample plate 81.

The source 1 of light is provided over the sample plate 81, and, for example, a He—Ne laser beam of a wavelength of 0.633 μm emitted from the source 1 of light falls on the sample 2 via a collimator lens 3, beam distribution shifter 4, mirror 94 and objective lens 5.

The beam distribution shifter 4 is disposed on the object image plane of the objective lens 5 and the sample 2 is disposed on the image-forming plane of the objective lens 5.

That is, the laser beam emitted from the source 1 of light is transformed into a parallel beam through the collimator lens 3 and falls on the beam distribution shifter 4 where it is divided into two light fluxes $L_1$ and $L_2$ having phases opposite to each other, which are then focused through the objective lens 5 to fall on a predetermined position on the sample 2.

A pair of detectors 95a and 95b consisting of light sensors are arranged near the upper surface of the sample plate 81 to detect light scattered by the edges of a pattern formed on the sample 2.

Figure 43:
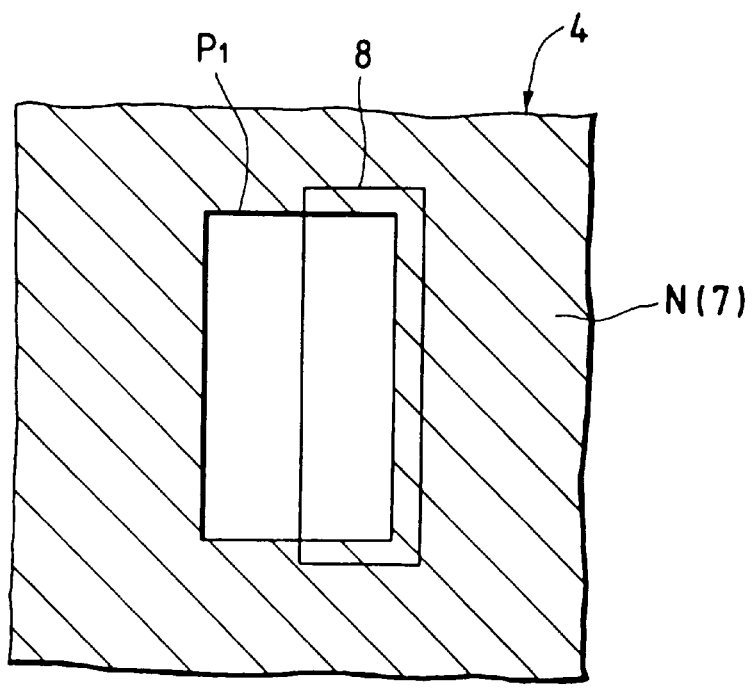
FIG. 43 is a plan view illustrating the structure of a beam distribution shifter provided in the size-measuring apparatus.
Figure 44:
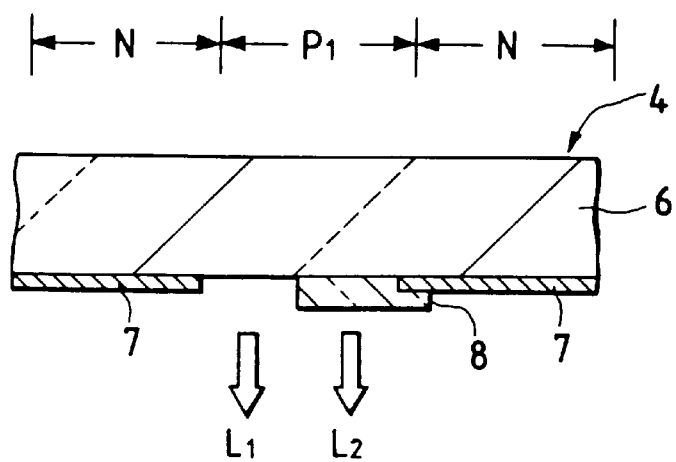
FIG. 44 is a sectional view illustrating the structure of the beam distribution shifter provided in the size-measuring apparatus.

FIG. 43 is a plan view showing the major portions of the beam distribution shifter 4, and FIG. 44 is a sectional view showing these major portions.

The beam distribution shifter 4 has a light transmission region $P_1$ and a light blocking region N formed on one surface of a transparent glass substrate 6. The light blocking region N is constituted by a light blocking film 7 made of chromium.

A phase shifter 8 made up of a thin transparent film such as spin-on-glass is formed on a portion of the light transmission region $P_1$. The phase shifter 8 occupies about a half of the whole area of the light transmission region $P_1$.

With the phase shifter 8 provided as described above, the laser beam that has passed through the light transmission region $P_1$ of the beam distribution shifter 4 is divided into two light fluxes $L_1$ and $L_2$ having phases opposite to each other. Moreover, the light flux $L_1$ that has passed through the region without the phase shifter 8 has an intensity which is nearly the same as the intensity of the light flux $L_2$ that has passed through the region having the phase shifter 8.

Figure 45:
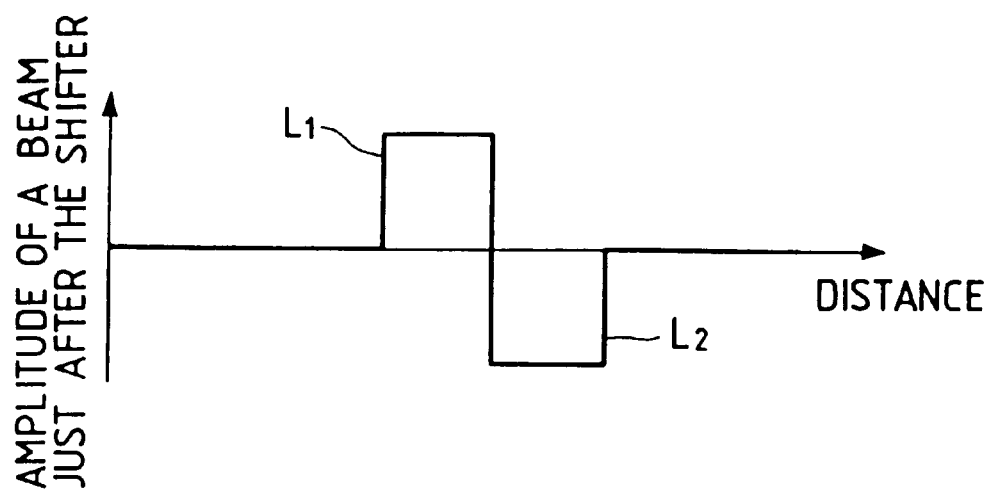
FIG. 45 is a diagram showing the amplitude of a light beam just after having passed through the beam distribution shifter.
Figure 46:
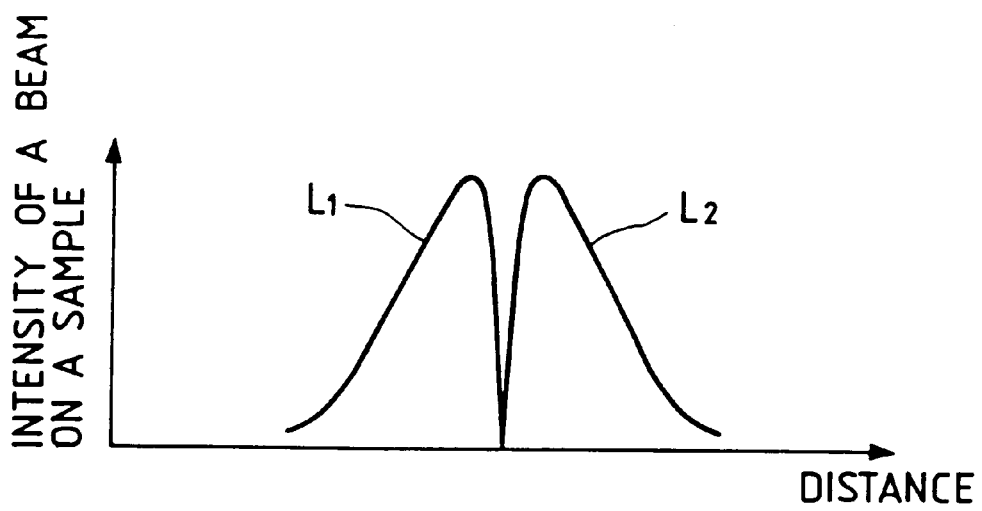
FIG. 46 is a diagram showing the intensity of the light beam on a sample.

Referring to FIG. 45, the above two light fluxes $L_1$ and $L_2$ have phases opposite to each other and have edges which are in contact with each other at the boundary therebetween. Therefore, if the two light fluxes $L_1$ and $L_2$ are focused through the objective lens 5 and allowed to fall on the sample 2, the two light fluxes $L_1$ and $L_2$ interfere with each other and are weakened at the boundary as shown in FIG. 46. Therefore, an increased contrast is exhibited at the boundary and two fine laser beams close to each other are obtained.

That is, by irradiating the sample 2 with two light fluxes $L_1$ and $L_2$ having phases opposite to each other and having edges which are in contact with each other at the boundary, it is possible to form a laser beam having a diameter smaller than an optical limit value determined by the wavelength of the laser beam and the numerical aperture of the objective lens 5.

It is also possible to form a groove in a portion of the light transmission region $P_1$ of the glass substrate 6 instead of employing the above-mentioned means of employing the phase shifter 8 for the light transmission region $P_1$, so that the light flux $L_2$ passing through the groove and the light flux $L_1$ passing through the remaining light transmission region $P_1$ have phases that are opposite to each other, in the same manner as that of the Embodiment 1.

Figure 47:
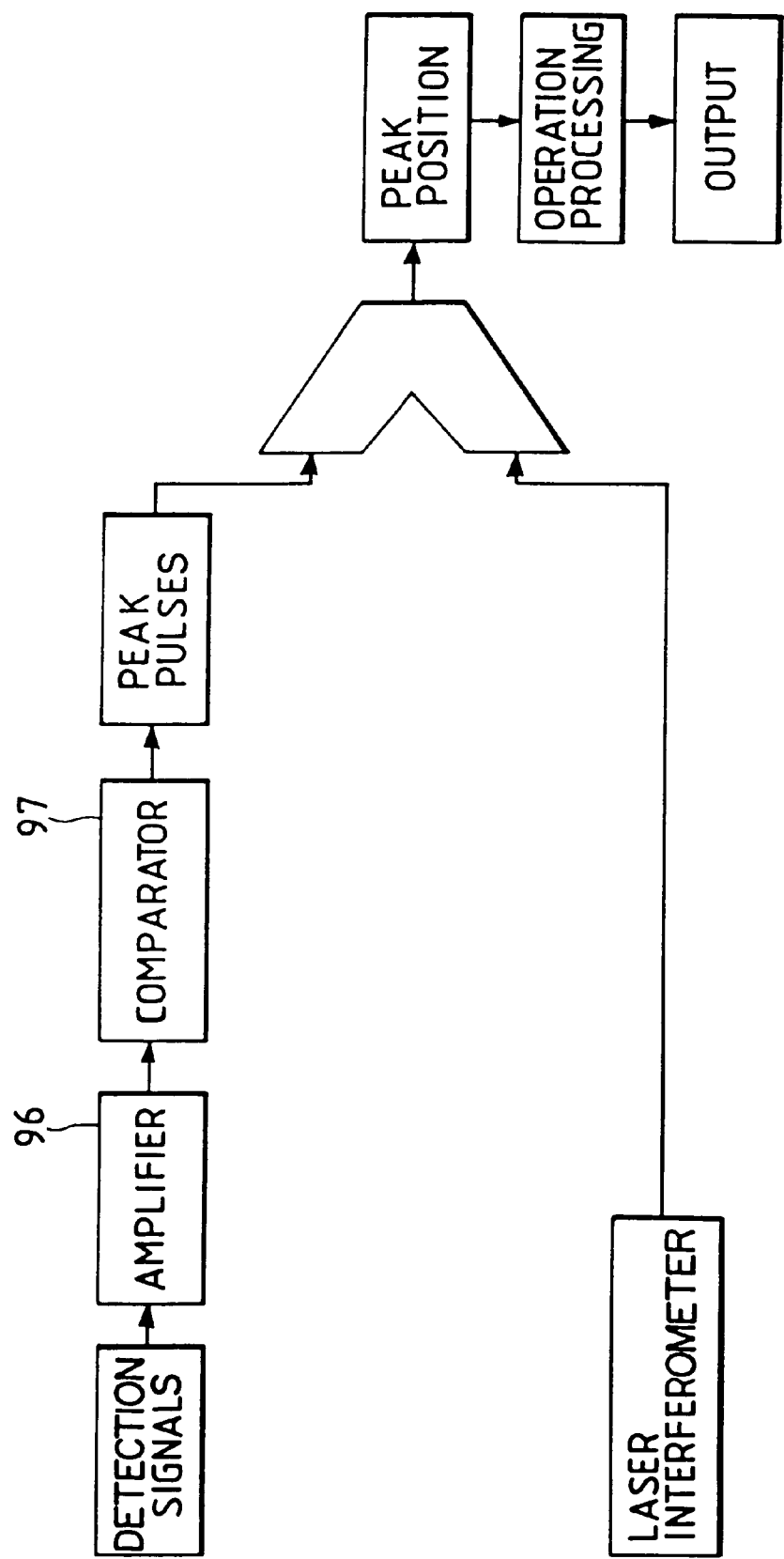
FIG. 47 is a diagram illustrating a size-measuring method using the size-measuring apparatus.

The method of measuring size using the thus obtained two fluxes $L_1$ and $L_2$ will now be described in conjunction with FIGS. 42, 47 and 48.

First, the laser beam emitted from the source 1 of light is divided into two light fluxes $L_1$ and $L_2$ via the beam distribution shifter 4 which are then focused through the objective lens 5 and allowed to fall on the sample 2. The sample plate 81 is then moved in a horizontal direction to scan the sample plate 81 relative to the fluxes $L_1$ and $L_2$ in the direction of measuring size. In this case, the two light fluxes $L_1$ and $L_2$ are scanned such that their traces are superposed.

Figure 48:
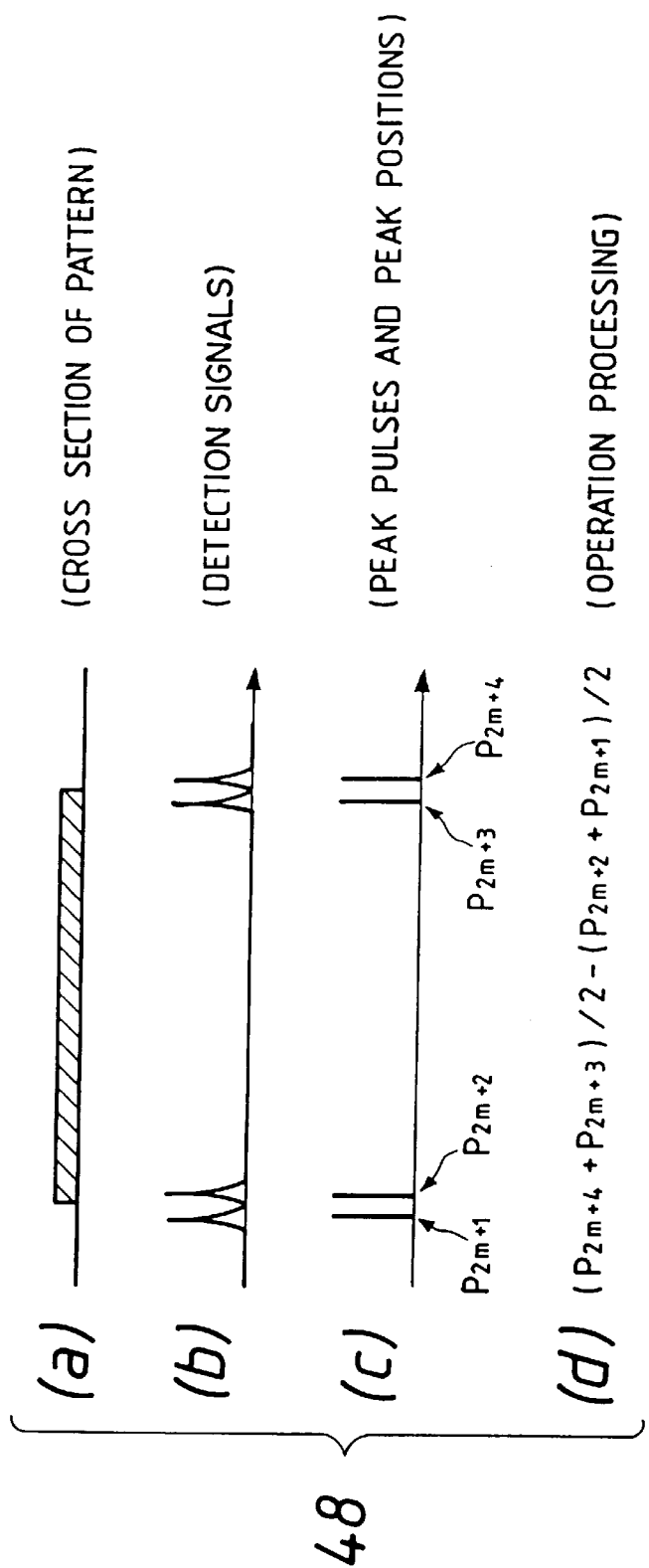
FIG. 48 is a diagram illustrating the size-measuring method using the size-measuring apparatus.

As the light fluxes $L_1$ and $L_2$ fall on the edges of the pattern formed on the sample 2 (see (a) of FIG. 48), the light is scattered by the steps of the edges. Detection signals of scattered light detected by the pair of detectors 95a and 95b provided near the upper surface of the sample plate 81 are amplified through an amplifier 96 and are sent to a comparator 97.

The positions of the two light fluxes $L_1$ and $L_2$ are very close to each other, and the signals detected by the detectors 95a and 95b exhibit a pattern having two peak intensity values at positions which are very close to each other as shown in (b) of FIG. 48.

The comparator 97 separates noise from the detection signals of scattered light and forms peak pulses consisting of a pair of peak pulses which are very close to each other as shown in (c) of FIG. 48, i.e., a peak pulse that stems from the first light flux $L_1$ and a peak pulse that stems from the second light flux $L_2$.

Next, the position coordinates of the peak pulses are derived from the moving amount of the sample plate 81 measured by the laser interferometer 92, and the position coordinate of the peak pulse obtained from the first light flux $L_1$ and the position coordinate of the peak pulse obtained from the second light flux $L_2$ are averaged through arithmetic processing to calculate correct positions of the edges, and then the size of the pattern is calculated from the edge positions as shown in (d) of FIG. 48.

According to the size-measuring method of this embodiment as described above, it is possible to improve the precision of measuring the size of a fine pattern by using two light fluxes $L_1$ and $L_2$ with a diameter smaller than an optical limit value that is determined by the wavelength of the laser beam and the numerical aperture of the objective lens 5.

In the foregoing description, the size is measured by detecting light scattered by the edges of the pattern. It is, however, also possible to measure the size by detecting light reflected by the photomask and finding a position at which the change in the reflection factor becomes a maximum. This system is effective in measuring the size of a pattern which has such a small step at an edge that it is difficult to detect the scattered light.

In the above description, use is made of the beam distribution shifter having a phase shifter provided in the light path of a laser beam in order to form two laser beams which have phases opposite to each other and which are close to each other. It is, however, also possible to divide a single laser beam into two beams having different optical paths, to provide a phase shifter on the optical path of one beam to invert the phase thereof, and then to combine the two beams together.

In scanning the laser beam, it is possible to further improve the precision of measuring the size by slightly vibrating the beam in the direction of measuring the size and detecting the scattered light or reflected light in synchronism with the slight vibration.

The foregoing description deals with the case where the embodiment is adapted to measuring the size of an integrated circuit pattern formed on a photomask. The method of measuring size of the embodiment, however, is in no way only limited thereto but can be widely adapted to measuring the sizes of fine patterns such as an integrated circuit pattern formed on a semiconductor wafer and a wiring pattern formed on a wiring board.

Embodiment 8

Figure 49:
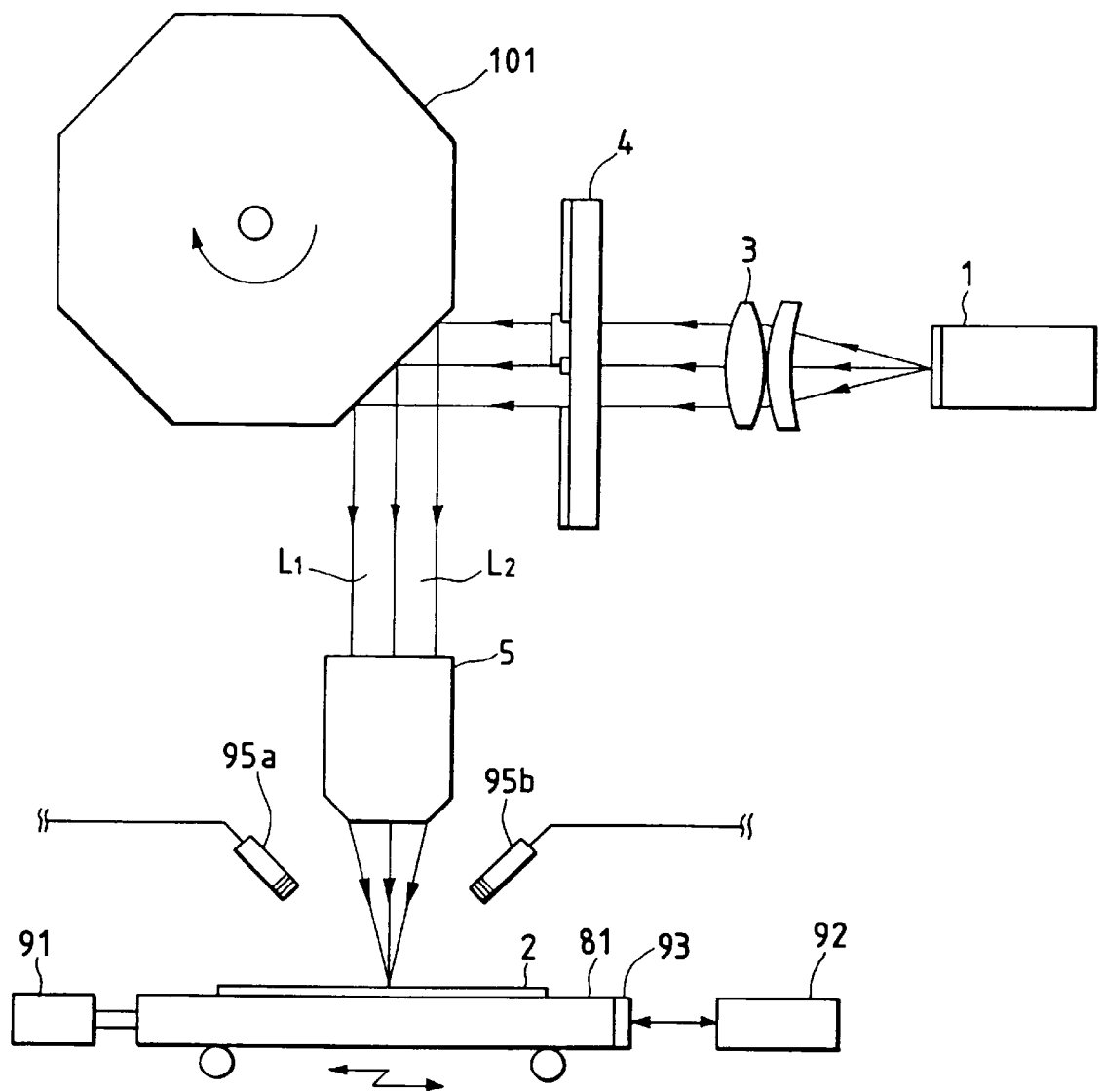
FIG. 49 is a diagram illustrating the structure of an optical system in an appearance inspection apparatus using the light beam-forming method of the present invention.

FIG. 49 illustrates an optical system of an appearance inspection apparatus 100 which utilizes the method of forming a light beam of the present invention.

The sample 2 is placed on a sample plate 81 comprising an XY table or the like that is movable in a horizontal plane. The sample plate 81 is movable a desired distance in a horizontal direction by being actuated by a drive unit 91 which is made up of a pulse motor or the like connected to one end thereof. The sample 2 may be a semiconductor wafer or a photomask for transferring an integrated circuit pattern onto a semiconductor wafer.

A laser interferometer 92 is provided near the sample plate 81, and a laser beam of a predetermined wavelength is projected therefrom onto a laser interference mirror 93 attached to an end of the sample plate 81, and the darkness and brightness of interference waves produced between the reflected light and the light reflected by a fixed mirror in the laser interferometer 92 are measured in order to highly precisely measure the moving amount of the sample plate 81.

The source 1 of light is provided obliquely above the sample plate 81, and, for example, a He—He laser beam of a wavelength of 0.633 μm emitted from the source 1 of light falls on the sample 2 via a collimator lens 3, beam distribution shifter 4, polygonal mirror 101, and objective lens 5.

The beam distribution shifter 4 is disposed on the object image plane of the objective lens 5 and the sample 2 is disposed on the image-forming plane of the objective lens 5.

That is, the laser beam emitted from the source 1 of light is transformed into a parallel beam through the collimator lens 3 and falls on the beam distribution shifter 4 where the beam is divided into two light fluxes $L_1$ and $L_2$ having phases opposite to each other which are then focused through the objective lens 5 and allowed to fall on a predetermined position on the sample 2.

The light fluxes $L_1$, $L_2$ falling on the sample 2 are deflected in a predetermined direction in response to rotation of polygonal mirror 101. The scanning is limited in an axial direction. By moving the sample plate 81 in a direction perpendicular to the above direction, therefore, the whole surface of the sample 2 can be scanned with the light fluxes $L_1$ and $L_2$.

A pair of detectors 95a and 95b consisting of light sensors are arranged near the upper surface of the sample plate 81 to detect light scattered by the edges of the pattern formed on the sample 2.

Figure 50:
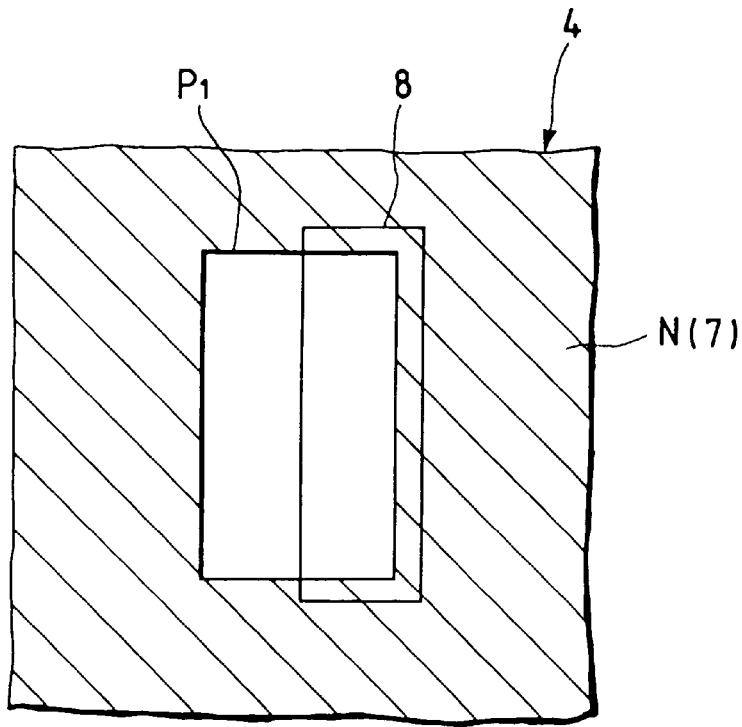
FIG. 50 is a plan view showing the structure of a beam distribution shifter provided in the appearance inspection apparatus.
Figure 51:
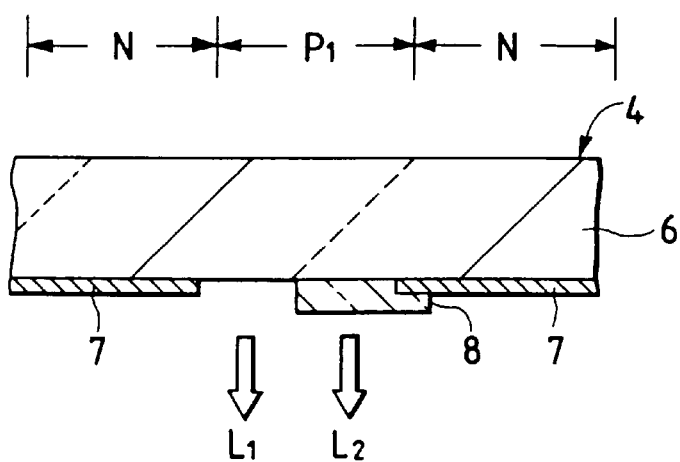
FIG. 51 is a sectional view showing the structure of the beam distribution shifter provided in the appearance inspection apparatus.

FIG. 50 is a plan view showing major portions of the beam distribution shifter 4, and FIG. 51 is a sectional view showing these major portions.

The beam distribution shifter 4 has a light transmission region $P_1$ and a light blocking region N formed on one surface of a transparent glass substrate 6. The light blocking region N is constituted by a light blocking film 7 composed of chromium.

A phase shifter 8 consisting of a thin transparent film such as spin-on-glass is formed on a portion of the light transmission region $P_1$. The phase shifter 8 occupies about a half of the whole area of the light transmission region $P_1$.

With the phase shifter 8 provided as described above, the laser beam that has passed through the light transmission region $P_1$ of the beam distribution shifter 4 is divided into two light fluxes $L_1$ and $L_2$ having phases opposite to each other. Moreover, the light flux $L_1$ that has passed through the region without the phase shifter 8 has an intensity which is nearly the same as the intensity of the light flux $L_2$ that has passed through the region having the phase shifter 8.

The above two light fluxes $L_1$ and $L_2$ have phases that are opposite to each other and have edges which are in contact with each other at the boundary therebetween. Therefore, if the two light fluxes $L_1$ and $L_2$ are focused through the objective lens 5 and allowed to fall on the sample 2, the two light fluxes $L_1$ and $L_2$ interfere with each other and are weakened at the boundary. Therefore, an increased contrast is exhibited at the boundary and two fine laser beams close to each other are obtained.

That is, by irradiating the sample 2 with two light fluxes $L_1$ and $L_2$ having phases opposite to each other and having edges which are in contact with each other at the boundary, it is possible to form a laser beam having a diameter smaller than an optical limit value determined by the wavelength of the laser beam and the numerical aperture of the objective lens 5.

The method of inspecting appearance using the thus obtained two light fluxes $L_1$ and $L_2$ will now be described in conjunction with FIGS. 49, 52 and 53.

First, the laser beam emitted from the source 1 of light is divided into two light fluxes $L_1$ and $L_2$ via the beam distribution shifter 4 which are then focused through the objective lens 5 and made to fall on the sample 2. The polygonal mirror 101 is then rotated to deflect the light fluxes $L_1$ and $L_2$ in a predetermined direction. In this case, the two light fluxes $L_1$ and $L_2$ are deflected so that their traces are superposed.

Figure 52:
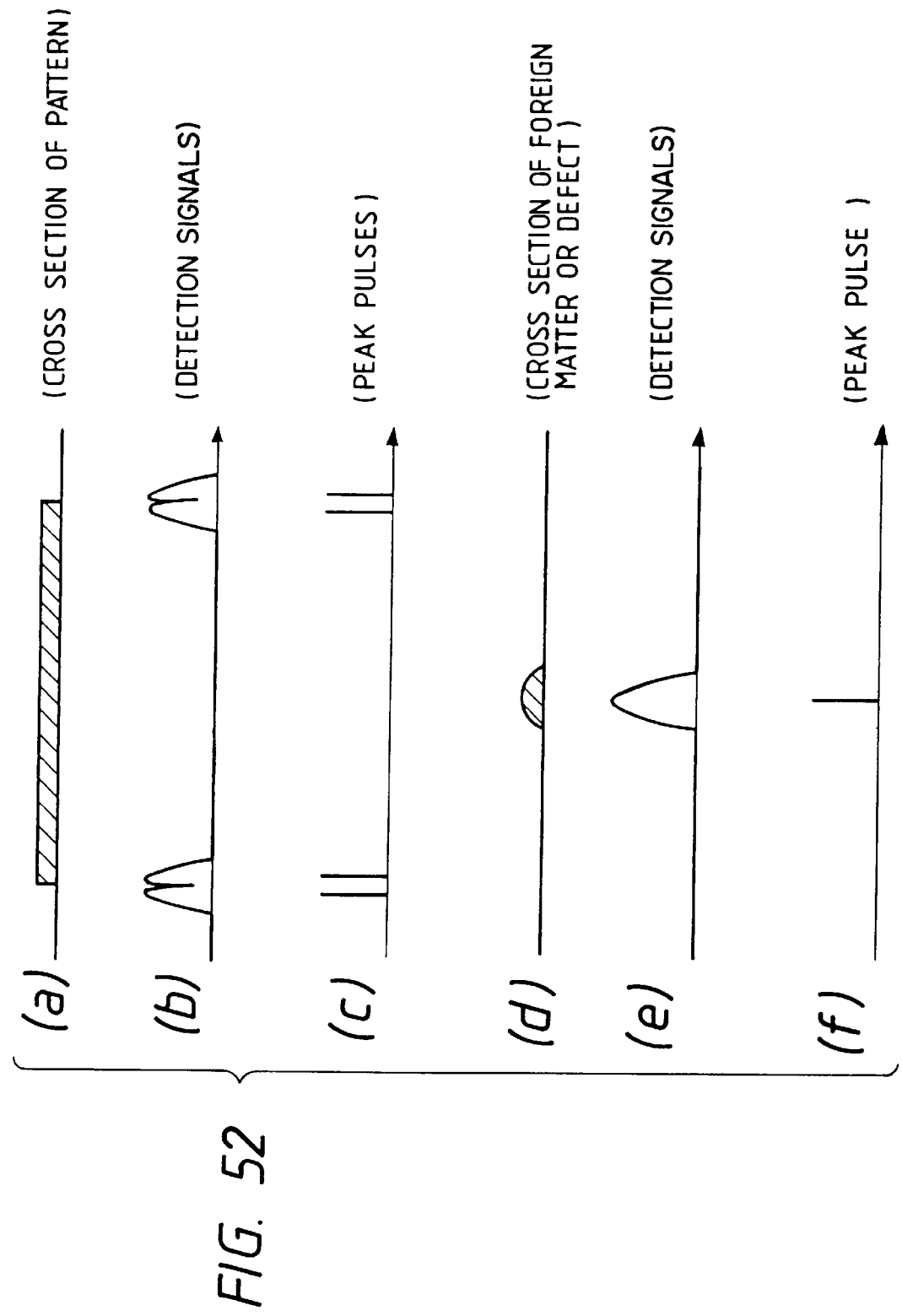
FIG. 52 is a diagram illustrating an appearance inspection method using the appearance inspection apparatus.
Figure 53:
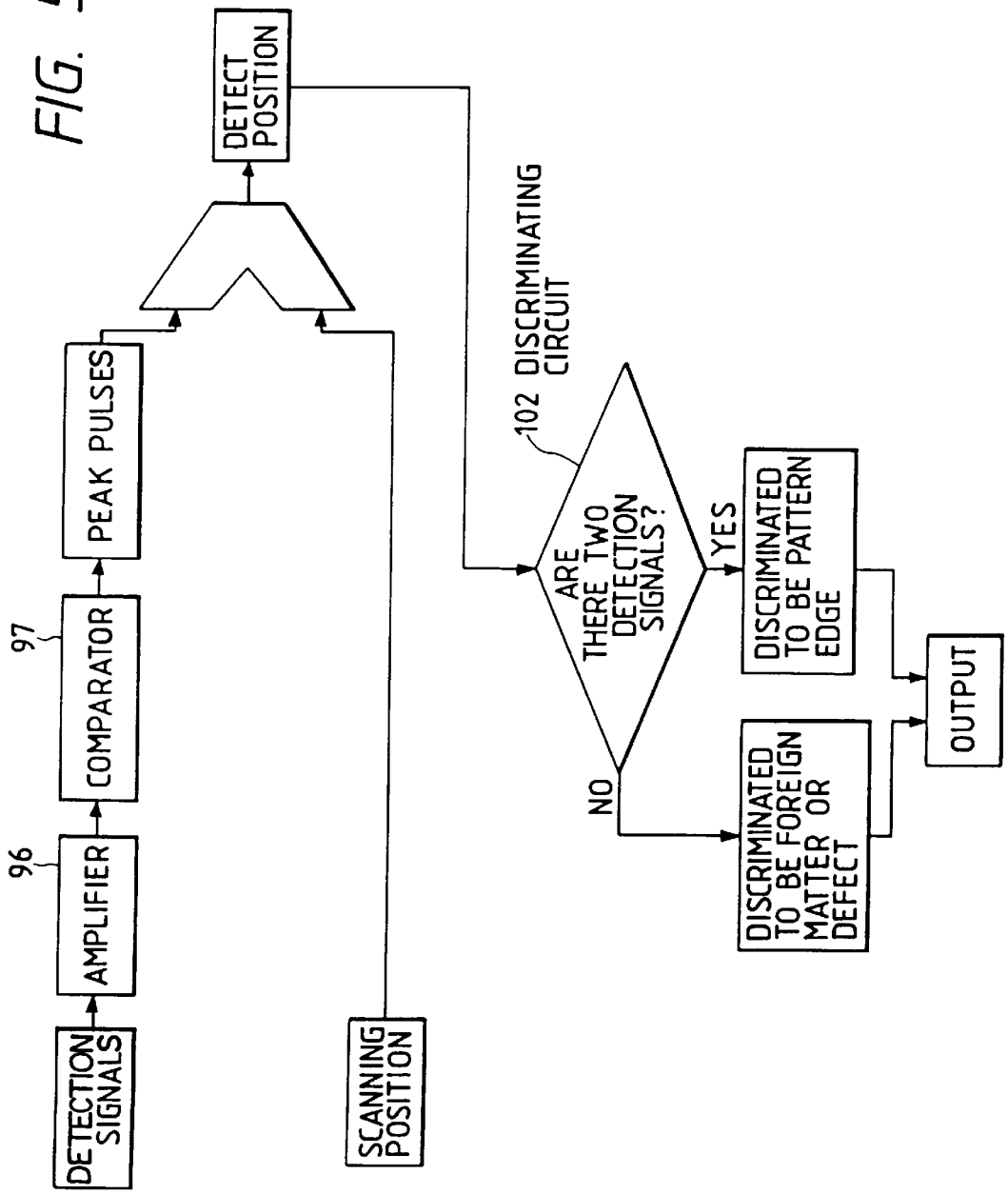
FIG. 53 is a diagram illustrating the appearance inspection method using the appearance inspection apparatus.

As the light fluxes $L_1$ and $L_1$ fall on the edges of the pattern formed on the sample 2 (see (a) of FIG. 52), the light is scattered by the steps of the edges. Detection signals of scattered light detected by the pair of detectors 95a and 95b provided near the upper surface of the sample plate 81 are amplified through an amplifier 96 and are sent to a comparator 97.

The positions of the light fluxes $L_1$ and $L_2$ are very close to each other, and the signals detected by the detectors 95a and 95b exhibit a pattern having two peak intensity values at positions which are very close to each other as shown in (b) of FIG. 52.

The detection signals are amplified by the amplifier 96 and only those signals having intensities greater than a predetermined value are output from the comparator 97. Then, there appear two peak pulses close to each other at places corresponding to the edges of the pattern as shown in (c) of FIG. 52.

The light is similarly scattered as the light fluxes $L_1$ and $L_2$ fall on foreign matter or a defect on the sample 2 (see (d)

of FIG. 52). In this case, however, the light is scattered by nearly the whole surface of the foreign matter or defect, and signals detected by the detectors 95*a* and 95*b* form a pattern in which a peak value of a signal from the light flux $L_1$ is superposed on a peak value of a signal from the light flux $L_2$ as shown in (e) of FIG. 52.

The detection signals are amplified by the amplifier 96 and only those signals having intensities greater than a predetermined level are output from the comparator 97, thereby obtaining a single peak pulse at a place corresponding to the position of the foreign matter or defect as shown in (f) of FIG. 52.

Next, detection positions of the peak pulses are found from the peak pulses, rotational amount of the polygonal mirror 101 and moving amount of the sample plate 81. When the number of peak pulses detected at a predetermined position is judged to be one by a discriminating circuit 102, it is determined that an edge of the pattern exists at the above predetermined position, and when the number of peak pulses is judged to be two, it is determined that foreign matter or a defect exists at the above predetermined position.

By the method of inspecting appearance of this embodiment as described above, it is possible to improve a precision of inspecting appearance of a fine pattern by using two light fluxes $L_1$ and $L_2$ having a diameter smaller than an optical limit value determined by the wavelength of the laser beam and the numerical aperture of the objective lens 5.

Figure 54:
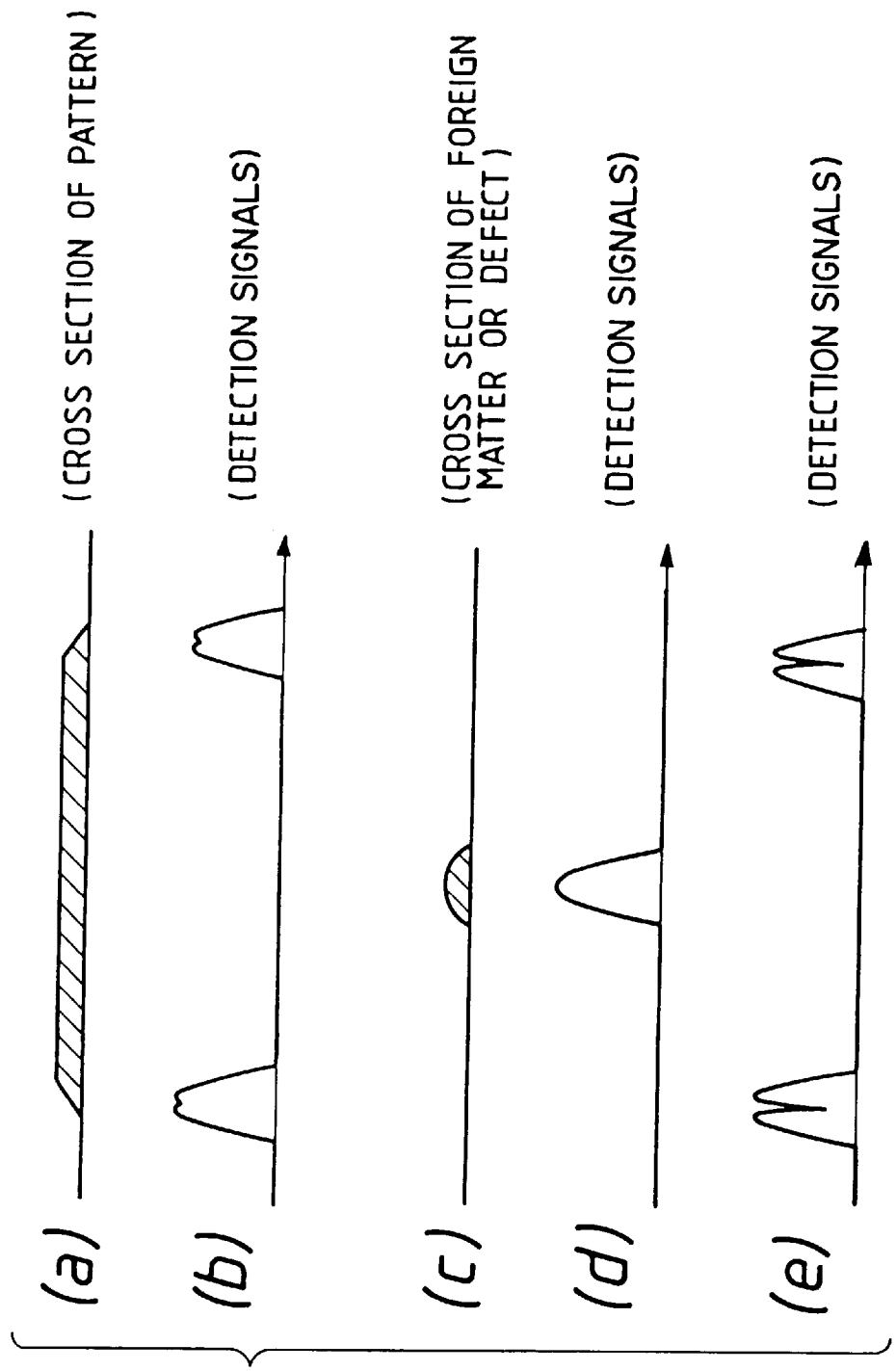
FIG. 54 is a diagram illustrating another appearance inspection method.

In the case of an integrated circuit pattern formed on the semiconductor wafer, however, the edges of the pattern may often be gently slanted as shown in (a) of FIG. 54.

As the light fluxes $L_1$ and $L_2$ fall on such edges, the light is scattered by the whole surface that is slanted, and the signals detected by the detectors 95*a* and 95*b* form a pattern in which a peak intensity value of a signal from the light flux $L_1$ is nearly superposed on a peak intensity value of a signal from the light flux $L_2$ as shown in (b) of FIG. 54.

When the detection signals are amplified by the amplifier 96 and if only those signals having intensities greater than a predetermined level are output from the comparator 97, there is obtained substantially only one peak pulse which cannot be easily distinguished from a peak pulse as shown in (d) of FIG. 54 that is obtained from foreign matter or a defect as shown in (c) of FIG. 54.

Figure 55:
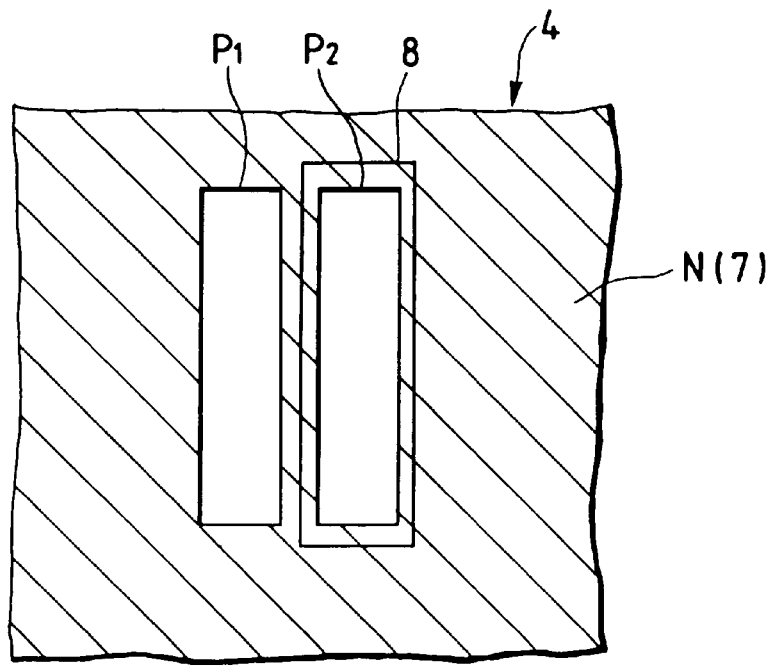
FIG. 55 is a plan view showing another structure of the beam distribution shifter in the appearance inspection apparatus.
Figure 56:
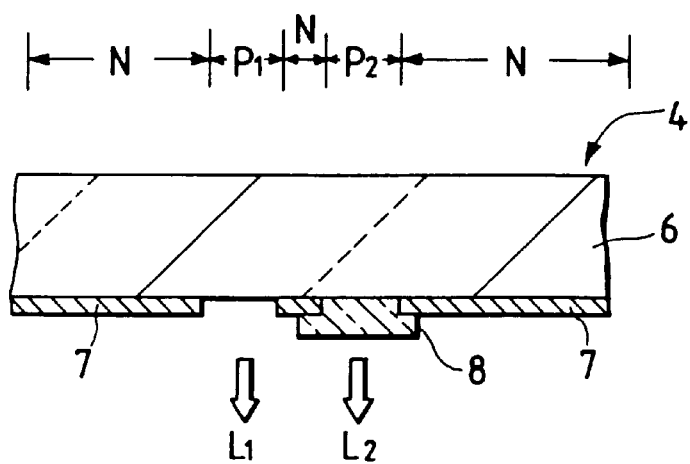
FIG. 56 is a sectional view showing the structure of the beam distribution shifter in FIG. 55.

In such a case, therefore, the appearance is detected using the beam distribution shifter 4 as shown in FIGS. 55 and 56. The beam distribution shifter 4 has a phase shifter 8 having a thin transparent film such as spin-on-glass formed on one of a pair of light transmission regions $P_1$ and $P_2$ sandwiching a light blocking region N of a predetermined width therebetween.

Figure 57:
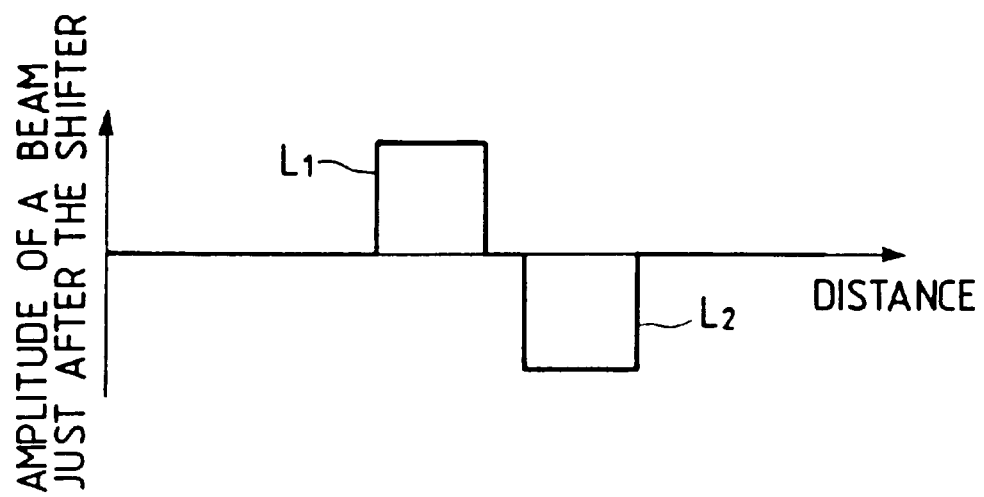
FIG. 57 is a diagram showing the amplitude of a light beam just after having passed through the beam distribution shifter.

Referring to FIG. 57, the two light fluxes $L_1$, $L_2$ that have passed through the light transmission regions $P_1$, $P_2$ and the phase shifter 8 have phases opposite to each other and are slightly separated from each other.

Figure 58:
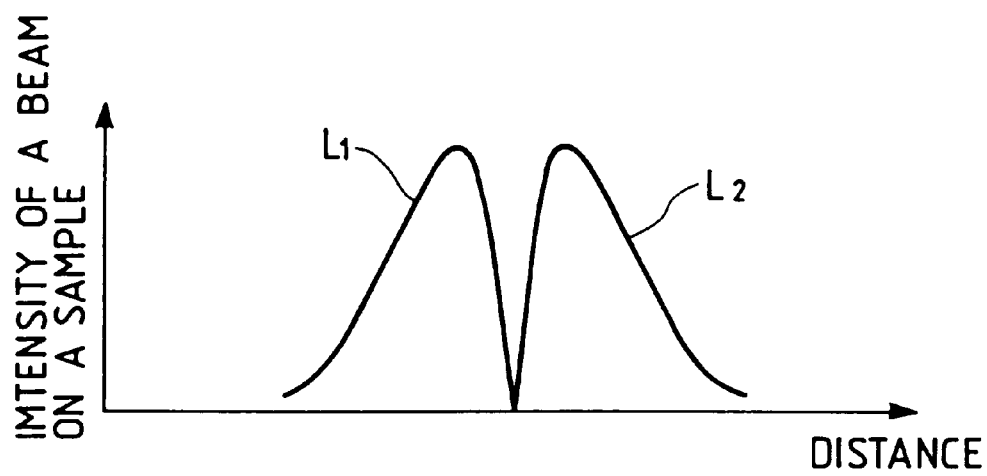
FIG. 58 is a diagram showing the intensity of a light beam on a sample.
Figure 59:
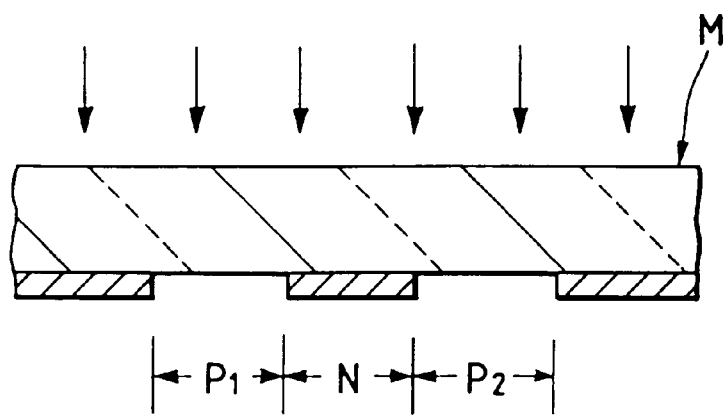
FIG. 59 is a sectional view showing major portions of a photomask.
Figure 60:
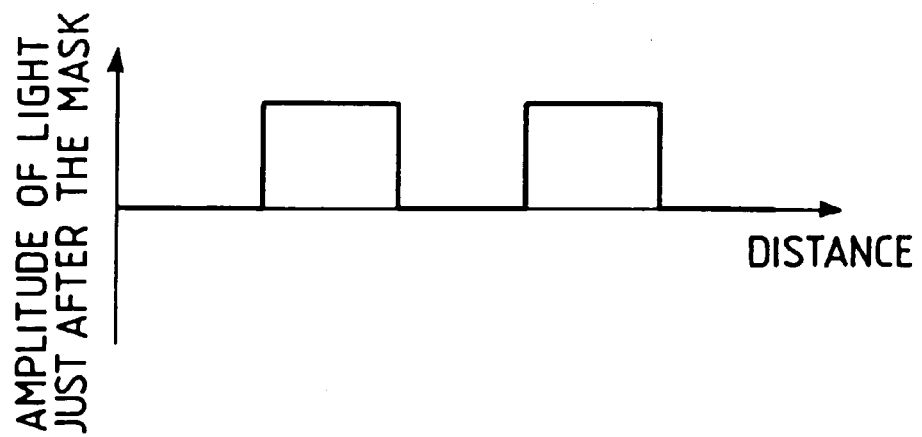
FIG. 60 is a diagram showing the amplitude of light just after having passed through the photomask.
Figure 61:
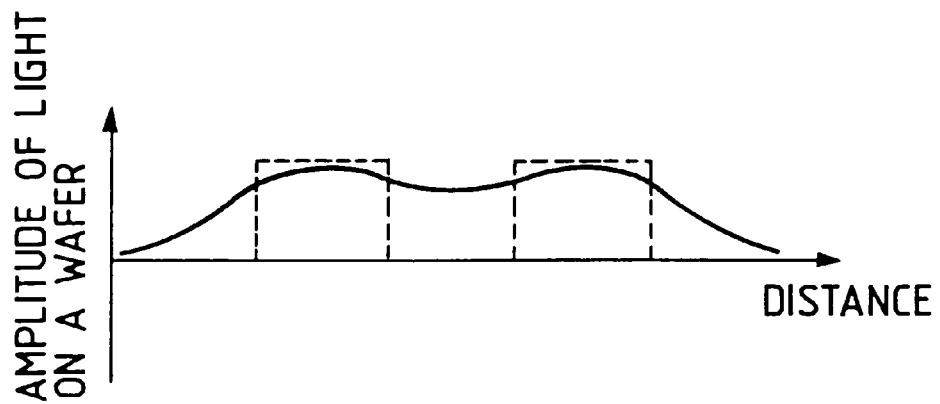
FIG. 61 is a diagram showing the amplitude of light on a semiconductor wafer.
Figure 62:
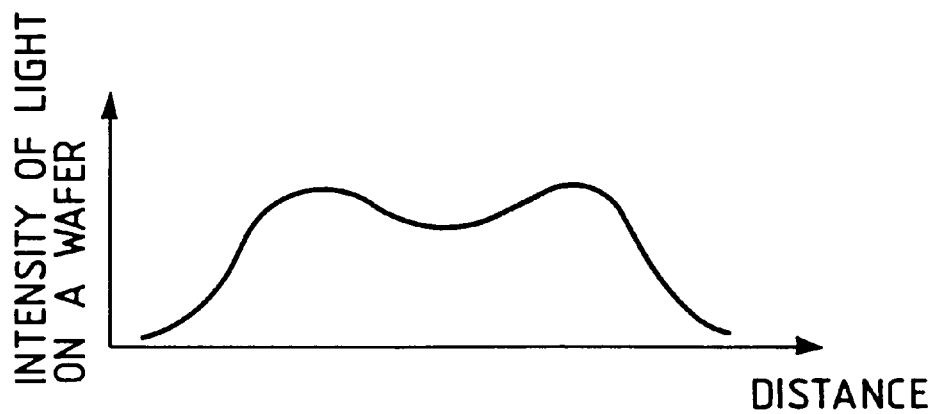
FIG. 62 is a diagram showing the intensity of light on the semiconductor wafer.
Figure 63:
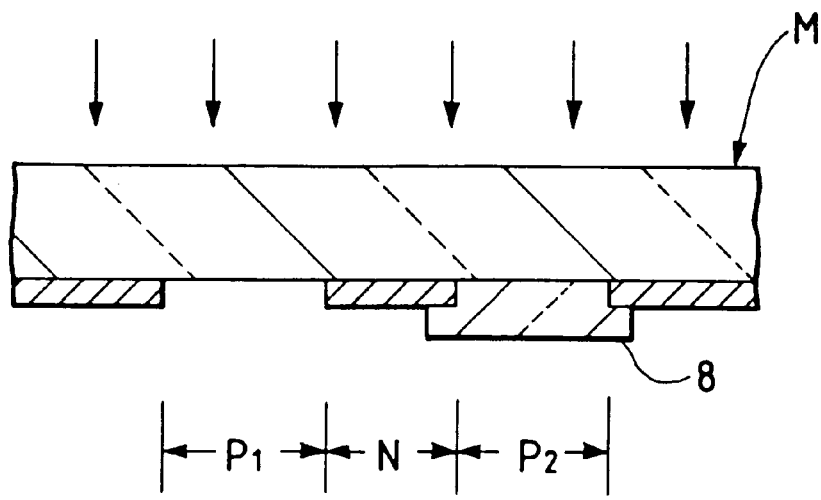
FIG. 63 is a sectional view showing major portions of a phase-shifting photomask.
Figure 64:
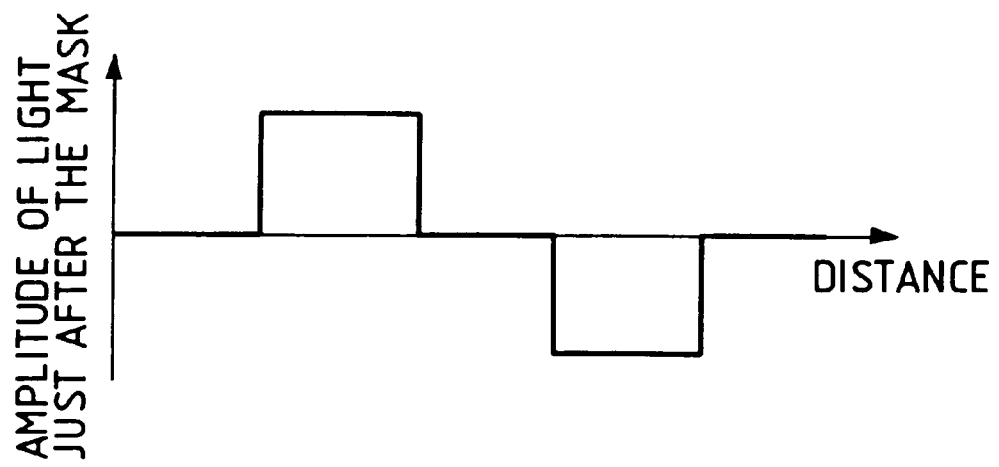
FIG. 64 is a diagram showing the amplitude of light just after having passed through the phase-shifting photomask.
Figure 65:
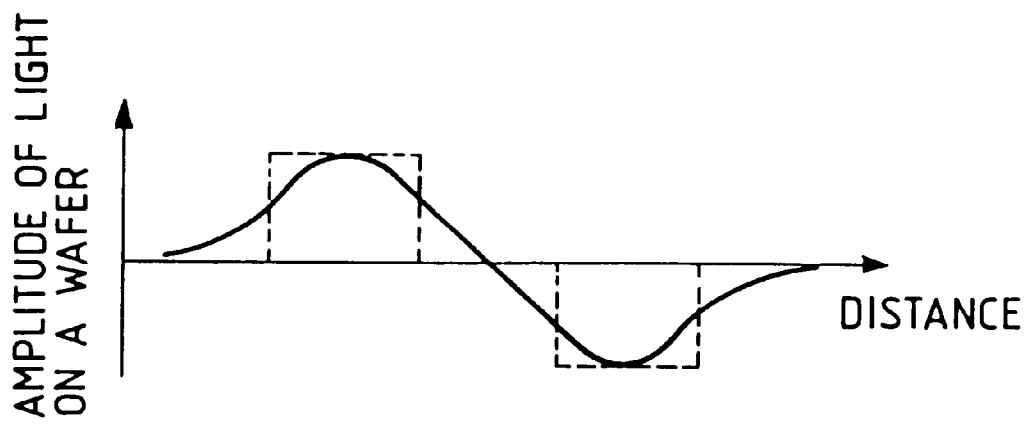
FIG. 65 is a diagram showing the amplitude of light on a semiconductor water.
Figure 66:
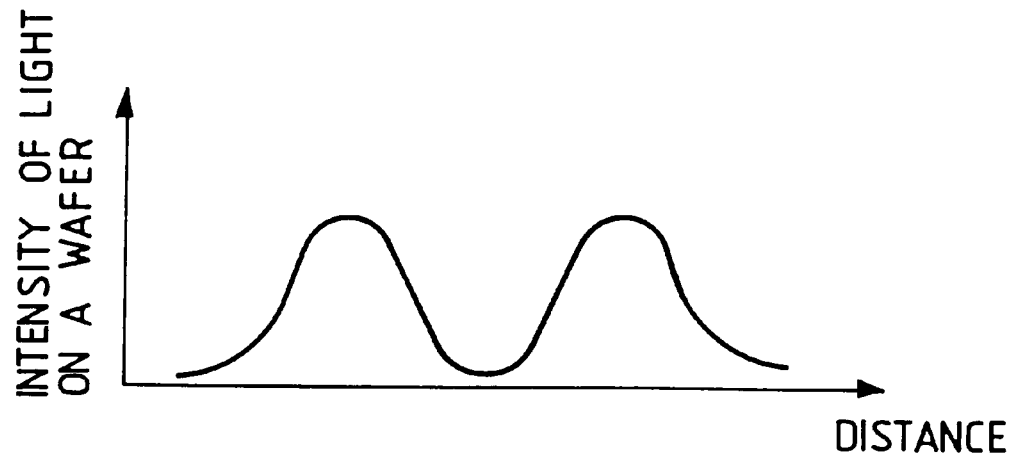
FIG. 66 is a diagram showing the intensity of light on the semiconductor wafer.

Therefore, if the two light fluxes $L_1$ and $L_2$ are focused through the objective lens 5 and made to fall on the sample 2, there are obtained two fine light fluxes $L_1$ and $L_2$ slightly separated from each other is shown in FIG. 58. The interval between the light fluxes $L_1$ and $L_2$ can be arbitrarily selected by changing the width of the light blocking region N between the pair of light transmission regions $P_1$ and $P_2$.

It is also possible to change the interval between the light fluxes $L_1$ and $L_2$ by changing the wavelength of the laser beam instead of employing the above-mentioned technique of changing the width of the light blocking region N between the light transmission regions $P_1$ and $P_2$. In this case, the interval between the light fluxes $L_1$ and $L_2$ can be decreased by decreasing the wavelength of the laser beam.

When the light fluxes $L_1$ and $L_2$ that have passed through the beam distribution shifter 4 fall on the slanted edges, the light is scattered by the whole slanted surface. However, since the light fluxes $L_1$ and $L_2$ are separated from each other, the signals detected by the detectors 95*a* and 95*b* form a pattern having two peak intensity values at two positions close to each other as shown in (e) of FIG. 54.

Therefore, the peak pulses obtained from the edges of the pattern can be easily distinguished from a single peak pulse that is obtained from foreign matter or a defect. According to this method, however, the interval between the light fluxes $L_1$ and $L_2$ is large, making it difficult to detect fine foreign matter or a fine defect.

In the foregoing description, it was mentioned how to detect the light scattered by the edges of a pattern or by the surface of foreign matter or a defect. The embodiment, however, can further be adapted to a method of inspecting appearance by detecting the light reflected by the surface of a sample or by detecting the light that has transmitted through a sample and by finding a position at which a change of reflection factor or transmission factor is the greatest. These systems are effective particularly in inspecting the appearance of samples having patterns for which it is difficult to detect the scattered light because of small steps at the edges.

In the foregoing description, two laser beams having phases opposite to each other and which are close to each other are formed by disposing the beam distribution shifter having a phase shifter on the optical path of the laser beam. However, it is also possible to divide a single laser beam into two beams having different optical paths, to dispose a beam distribution shifter in the optical path of one beam to invert the phase of the laser beam, and to combine the two beams together.

In the foregoing description, the laser beam is deflected by rotating the polygonal mirror 101. It is, however, also possible to deflect the laser beam using an AO (acousto-optic effect) element which periodically changes the refractive index of a glass body by applying a vibration thereto using, for example, a piezoelectric element.

In deflecting the laser beam, it is possible to further improve the precision for inspecting the appearance by slightly vibrating the beam in the scanning direction, and detecting the scattered light or reflected light in synchronism with the slight vibration.

The foregoing description deals with the case where the embodiment is adapted to inspecting the appearance of an integrated circuit pattern formed on a photomask or on a semiconductor wafer. The embodiment, however, is in no way only limited thereto but can be widely adapted to inspecting the appearance of a wiring board on which, for example, a fine wiring pattern is formed.

In the foregoing is concretely described the invention accomplished by the present inventors by way of various embodiments. The invention, however, is in no way limited to the aforementioned embodiments only but can be varied in a variety of other ways without departing from the gist thereof.

Through the foregoing embodiments the method of forming fine light fluxes chiefly by changing the phase of part of the light fluxes on the object plane is described. The invention, however, is not necessarily only limited thereto.

That is, fine light fluxes may be formed by placing a filter means which blocks or weakens the diffracted light of 0-th order on the pupil plane of the projection optical system or on a Fourier-transformed plane for the object plane thereof, or by further placing a bifocal filter thereon.

It is further allowable to place a filter or an opening on the aperture surface of the illumination system to permit the passage of a ring belt only in place of the above means (so-called ring belt illumination).

Briefly described below are the effects obtained by representative examples of the invention disclosed in this application.

(1) By the method of forming a light beam of the present invention in which the light emitted from the source of light is divided into two light fluxes using the beam distribution shifter so that they may have phases opposite to each other, and the two light fluxes are focused through the objective lens and allowed to fall as a light beam on the surface of the sample, it is possible to form a fine light beam overcoming the limitation due to the wavelength of the light emitted from the source of light and characteristics of the objective lens.

(2) By the method of forming a light beam of the present invention, pits finer than conventional ones can be formed in the mother disk of optical disks and optomagnetic disks, contributing to greatly increasing the data recording density of the optical disks or optomagnetic disks.

(3) By the method of forming a light beam of the present invention, the surface of the sample can be irradiated with a laser beam which is finer than a conventional one, enabling the resolution of the optical microscope apparatus to be greatly enhanced.

(4) By the method of forming a light beam of the present invention, the surface of the semiconductor wafer can be irradiated with a laser beam which is finer than a conventional one. This makes it possible to decrease the size of links used for replacing a defective circuit with a redundant circuit in the technology of remedying defects of semiconductor memories, enabling the memory LSIs to be fabricated in small sizes.

By the method of forming a light beam of the present invention, furthermore, the surface of the semiconductor wafer can be irradiated with many laser beams having diameters and distances therebetween smaller than those of conventional ones. It is therefore possible to simultaneously melt-cut a plurality of links formed on a semiconductor wafer, and hence to improve throughput in the operation of melt-cutting the links.

Moreover, since the size of links and distances therebetween can be decreased, the memory LSIs can be fabricated in small sizes.

(5) By the method of forming a light beam of the present invention, the inside of through holes formed in the surface of the semiconductor chip can be irradiated with a laser beam deeper than conventionally. Therefore, the semiconductor chips and the semiconductor wafers can be connected together via fine wiring, enabling the LSIs to be fabricated in a small size and in a large scale integrated form.

(6) By the method of forming a light beam of the present invention, two fine laser beams can be formed which are very close to each other. The surface of the sample is irradiated with these two fine laser beams from an oblique direction, the reflected beams thereof are detected to find the average value of respective peak intensity positions of the two laser beams or to find a position of a region having a very small intensity that exists between them in order to measure the height of the surface of the sample with a precision higher than that when the reflected light of a single laser beam is detected.

When the invention is adapted to, for example, an election beam drawing apparatus, therefore, it is possible to correctly control the focusing operation of the objective lens or to correctly detect the position of a positioning mark on the semiconductor wafer, and hence to draw a pattern more precisely.

When the invention is adapted to, for example, a light exposure apparatus, furthermore, the focusing operation of the reduction projection lens for the semiconductor wafer can be carried out highly precisely contributing to improving the dimensional precision of the integrated circuit pattern that is transferred onto the semiconductor wafer.

(7) By the method of forming a light beam of the present invention, it is possible to enhance the precision of measuring the size of a fine pattern formed on the surface of a sample.

(8) By the method of forming a light beam of the present invention, it is possible to enhance the precision of inspecting the appearance of a sample on which a fine pattern is formed.

What is claimed is:

1. A method of observing a sample comprising the steps of:

emitting light from a light source;

dividing the light emitted from the light source into a first light flux and a second light flux, a phase of the second light flux being the same as a phase of the first light flux;

inverting the phase of the second light flux such that the second light flux having the inverted phase has a phase opposite to the phase of the first light flux;

focusing the first light flux and the second light flux having the inverted phase on a surface of the sample with an objective lens to form at least one focused light beam on the surface of the sample; and observing the sample using the at least one focused light beam;

wherein destructive interference between the first light flux and the second light flux having the inverted phase occurs in the at least one focused light beam, thereby reducing a size of each of the at least one focused light beam on the surface of the sample relative to a size each of the at least one focused light beam would have on the surface of the sample if the destructive interference did not occur.

2. A method according to claim 1, wherein the first light flux has a first intensity and is incident on a central portion of the objective lens;

wherein the second light flux having the inverted phase has a second intensity smaller than the first intensity and is incident on a peripheral portion of the objective lens;

wherein one focused light beam is formed in the focusing step; and wherein destructive interference between the first light flux and the second light flux having the inverted phase occurs in the one focused light beam, thereby reducing a size of the one focused light beam on the surface of the sample relative to a size the one focused light beam would have on the surface of the sample if the destructive interference did not occur.

3. A method according to claim 2, wherein the objective lens is part of a confocal optical system of a scanning optical microscope.

4. A method according to claim 1, wherein the first light flux has a first intensity and the second light flux having the inverted phase has a second intensity substantially equal to the first intensity;

wherein an edge of the first light flux and an edge of the second light flux are in contact with each other at a boundary between the first light flux and the second light flux;

wherein two focused light beams are formed in the focusing step; and wherein destructive interference between the first light flux and the second light flux having the inverted phase occurs in the two focused light beams, thereby reducing a size of each of the two focused light beams on the surface of the sample and a spacing between the two focused light beams on the surface of the sample relative to a size each of the two focused light beams would have on the surface of the sample and a spacing between the two focused light beams that would exist on the surface of the sample if the destructive interference did not occur.

5. A method according to claim 1, wherein the first light flux has a first intensity and the second light flux having the inverted phase has a second intensity substantially equal to the first intensity;

wherein an edge of the first light flux and an edge of the second light flux are separated from each other by a gap at a boundary between the first light flux and the second light flux;

wherein two focused light beams are formed in the focusing step; and wherein destructive interference between the first light flux and the second light flux having the inverted phase occurs in the two focused light beams, thereby reducing a size of each of the two focused light beams on the surface of the sample and a spacing between the two focused light beams on the surface of the sample relative to a size each of the two focused light beams would have on the surface of the sample and a spacing between the two focused light beams that would exist on the surface of the sample if the destructive interference did not occur.

6. A method according to claim 1, wherein one focused light beam is formed in the focusing step; and wherein the observing step includes observing a profile of the surface of the sample by performing the following steps:

irradiating the surface of the sample with the one focused light beam;

producing relative movement between the one focused light beam and the sample to cause the one focused light beam to be scanned across the surface of the sample;

detecting light from the one focused light beam reflected from the surface of the sample as the one focused light beam is scanned across the surface of the sample; and observing the profile of the surface of the sample based on the detected reflected light.

7. A method according to claim 1, wherein one focused light beam is formed in the focusing step; and wherein the observing step includes observing internal defects of the sample by performing the following steps:

irradiating the surface of the sample with the one focused light beam;

producing relative movement between the one focused light beam and the sample to cause the one focused light beam to be scanned across the surface of the sample;

detecting a light-induced current in the sample as the one focused light beam is scanned across the surface of the sample; and detecting the internal defects in the sample based on the detected light-induced current.

8. A method according to claim 1, wherein two focused light beams are formed in the focusing step; and wherein the observing step includes measuring a height of the surface of the sample by performing the following steps:

irradiating the surface of the sample with the two focused light beams such that the two focused light beams are incident on the surface of the sample at an oblique angle with respect to the surface of the sample and are thereafter reflected from the surface of the sample, the two focused light beams being spaced apart from each other on the surface of the sample;

detecting positions of peak intensities of the two reflected focused light beams or a position of a low intensity region between the peak intensities; and measuring the height of the surface of the sample based on an average of the detected positions of the peak intensities or based on the detected position of the low intensity region.

9. A method according to claim 1, wherein two focused light beams are formed in the focusing step;

wherein there is a pattern on the surface of the sample; and wherein the observing step includes measuring a size of the pattern on the surface of the sample by performing the following steps:

irradiating the surface of the sample with the two focused light beams such that the two focused light beams are spaced apart from each other on the surface of the sample;

producing relative movement between the two focused light beams and the sample to cause the two focused light beams to be deflected across the pattern in a direction in which the size of the pattern is to be measured such that resulting traces of the two focused light beams on the surface of the sample are superposed upon each other;

detecting light from the two focused light beams scattered or reflected by the pattern as the two focused light beams are deflected across the pattern; and measuring the size of the pattern based on the detected scattered or reflected light.

10. A method according to claim 1, wherein two focused light beams are formed in the focusing step;

wherein there is a pattern on the surface of the sample; and wherein the observing step includes inspecting an appearance of the surface of the sample by performing the following steps:

irradiating the surface of the sample with the two focused light beams such that the two focused light beams are spaced apart from each other on the surface of the sample;

producing relative movement between the two focused light beams and the sample to cause the two focused light beams to be deflected across a predetermined position on the surface of the sample such that resulting traces of the two focused light beams on the surface of the sample are superposed upon each other;

detecting light from the two focused light beams scattered or reflected by the surface of the sample at the predetermined position as the two focused light beams are deflected across the predetermined position;

detecting a number of peaks having an intensity greater than a predetermined level in the detected scattered or reflected light;

if the detected number of peaks is two, determining that an edge of the pattern is present at the predetermined position; and if the detected number of peaks is one, determining that foreign matter or a defect is present at the predetermined position.

11. A method according to claim 10, wherein edges of the pattern are substantially perpendicular to the surface of the sample; and wherein an edge of the first light flux and an edge of the second light flux are in contact with each other at a boundary between the first light flux and the second light flux.

12. A method according to claim 10, wherein edges of the pattern are slanted at an angle with respect to the surface of the sample; and wherein an edge of the first light flux and an edge of the second light flux are separated from each other by a gap at a boundary between the first light flux and the second light flux, the gap being determined based on the angle at which the edges of the pattern are slanted.

13. A method of observing a semiconductor wafer or an optical mask comprising the steps of:

emitting a light flux from a light source;

passing the light flux through a beam distribution shifter which divides the light flux into a first light flux having a first phase and a second light flux having a second phase which is inverted with respect to the first phase; and focusing the first light flux and the second light flux onto a sampling plane of a semiconductor wafer or an optical mask to be observed with an optical system to form one focused light spot on the sampling plane such that a size of the one focused light spot on the sampling plane is reduced due to destructive interference between the first light flux and the second light flux relative to a size the one focused light spot would have on the sampling plane absent the destructive interference between the first light flux and the second light flux.

14. A method according to claim 13, wherein the light source is a laser light source.

15. A method according to claim 14, further comprising the step of performing relative scanning between the one focused light spot and a region of the sampling plane.

16. A method according to claim 15, wherein the beam distribution shifter is disposed on a conjugate plane of the sampling plane with respect to the optical system.

17. A method according to claim 16, further comprising the steps of:

gathering a reflected light flux from the one focused light spot with the optical system;

passing the gathered reflected light flux through the beam distribution shifter which divides the gathered reflected light flux into a first reflected light flux having a first phase and a second reflected light flux having a second phase which is inverted with respect to the first phase; and focusing the first reflected light flux and the second reflected light flux onto a detecting surface of a photodetector with the optical system.

18. A method according to claim 17, wherein the optical system is confocal with respect to the detecting surface and the sampling plane.

19. A method of observing a semiconductor wafer or an optical mask comprising the steps of:

emitting a light flux from a light source;

dividing the light flux into a first light flux and a second light flux each having a first phase;

inverting the first phase of the second light flux such that the second light flux has a second phase which is inverted with respect to the first phase of the first light flux;

focusing the first light flux and the second light flux onto a sampling plane of a semiconductor wafer or an optical mask to be observed with an optical system to form one focused light spot on the sampling plane such that a size of the one focused light spot on the sampling plane is reduced due to destructive interference between the first light flux and the second light flux relative to a size the one focused light spot would have on the sampling plane absent the destructive interference between the first light flux and the second light flux;

gathering a post-incidence light flux resulting from incidence of the one focused light spot on the sampling plane with the optical system; and focusing the gathered post-incidence light flux onto a detecting surface of a photodetector with the optical system.

20. A method according to claim 19, wherein the optical system is confocal with respect to the detecting surface and the sampling plane.

21. A method according to claim 20, wherein the light source is a laser light source.

22. A method according to claim 21, further comprising the step of performing relative scanning between the one focused light spot and a region of the sampling plane.

* * * * *